(12) United States Patent
Seed et al.

(10) Patent No.: US 9,045,523 B2
(45) Date of Patent: Jun. 2, 2015

(54) COMPOUNDS

(75) Inventors: Michael Peter Seed, London (GB);
Michael Burnet, Tubingen (DE); Hans Hurgen Gutke, Tubingen (DE)

(73) Assignees: PHAROS PHARMACEUTICALS INC., Rancho Palos Verdes, CA (US);
DIOSAMINE DEVELOPMENT CORPORATION, Berkeley Heights, NJ (US)

( * ) Notice: Subject to any disclaimer, the term of this patent is extended or adjusted under 35 U.S.C. 154(b) by 1504 days.

(21) Appl. No.: 12/596,068

(22) PCT Filed: Nov. 14, 2007

(86) PCT No.: PCT/EP2007/062355
§ 371 (c)(1),
(2), (4) Date: Nov. 5, 2010

(87) PCT Pub. No.: WO2008/059003
PCT Pub. Date: May 22, 2008

(65) Prior Publication Data
US 2011/0044901 A1    Feb. 24, 2011

(30) Foreign Application Priority Data

Nov. 14, 2006   (GB) .................................. 0622688.0
Jun. 11, 2007   (GB) .................................. 0711138.8

(51) Int. Cl.
| | |
|---|---|
| A01N 43/04 | (2006.01) |
| A61K 31/70 | (2006.01) |
| C07K 9/00 | (2006.01) |
| C07H 13/04 | (2006.01) |
| C07H 15/04 | (2006.01) |

(52) U.S. Cl.
CPC ................ *C07K 9/005* (2013.01); *C07H 13/04* (2013.01); *C07H 15/04* (2013.01)

(58) Field of Classification Search
None
See application file for complete search history.

(56) References Cited

U.S. PATENT DOCUMENTS

| | | | |
|---|---|---|---|
| 2,808,404 A | 10/1957 | Erickson | |
| 5,008,247 A | 4/1991 | Meinetsberger | |
| 5,202,311 A | 4/1993 | Folkman et al. | |
| 5,631,245 A | 5/1997 | Drube | |
| 5,783,568 A * | 7/1998 | Schlessinger et al. | 514/53 |
| 5,874,411 A | 2/1999 | Srivastava | |
| 6,433,012 B1 | 8/2002 | Tuse et al. | |
| 6,608,032 B1 | 8/2003 | Enoki et al. | |

FOREIGN PATENT DOCUMENTS

| | | |
|---|---|---|
| ES | 0551865 | 2/1986 |
| WO | WO 89/05646 | 6/1989 |
| WO | WO 95/34313 | 12/1995 |
| WO | WO 96/35700 | 11/1996 |
| WO | WO 97/18222 | 5/1997 |
| WO | WO 98/37902 | 3/1998 |
| WO | WO 2005/061523 | 7/2005 |

OTHER PUBLICATIONS

Bergwerff et al. Eur. J. Biochem. (1995), vol. 228, pp. 1009-1019.*
Ronca et al., "Anti-Inflammatory Activity of Chondroitin Sulfate", *Osteoarthritis and Cartilage*, Bailliere Tindall, London, GB, vol. 6 (Suppl. A.), May 1998, pp. 14-21, XP022221988, ISSN: 1063-4584.
PCT/EP2007/062355 International Search Report.
Bolton, et al., "Inhibition of antigen-induced arthritis by diglucosylamine, an immunomodulator identified from spleen", Inflamm. Res., Supplement 2, 2005, p. s-121.
Forsten, et al., "A Simple Assay for Evaluating Inhibitors of Proteoglycan-Ligand Binding", Ann. Biomed. Eng. 28(1), 2000, pp. 119-127.
Lees, et al., "Anti-rheumatic activity and cytokine synthesis inhibition by the oliosulphated disaccharide sucrose octasulphate.", 8th Jenner Glycobiology and Medicine Syposium, Oct. 21-23, 2007.
Olsen, et al., "Modulation of Influenza in Mice by Transfer Factory Therapy", J. Reticuloendothel Soc., 1978, vol. 24(5), pp. 53-62.
Seed, et al., "Antirheumatic/TNF Action by Free & Polysulphated Diglucopyranosylamine", Inflamm. Res. Supplement 3, 2007, pp. S-371-S372.
Shriver, et al., "Glycomics: A Pathway to a Class of New and Improved Therapeutics", Genomics and Proteomics, Nature Reviews, vol. 3, Oct. 2004, pp. 863-873.
Zhou, et al., "Identification and Dynamics of a Heparin-Binding Site in Hepatocyte Growth Factor", Biochemistry, 38 (45), 1999, pp. 14793-14802.
Anagnostou et al., "Crystallographic studies on two bioisosteric analogues . . . glycogen phosphorylase",Bioorg. Med. Chem., 2006, 14, pp. 181-189.
Arunkumar et al., "Oligomerization of acidic fibroblast growth factor is not a prerequisite for its cell proliferation activity", Protein Sci. 11(5) (2002), 1050-61.
Babczinski, "Plant cell cultures as a model for the biochemistry of crop selectivity", Pestic Sci, 1999, 55, pp. 671-674.
Bogoevska et al., "CEACAM1, an adhesion molecule of human granulocytes . . . via Lewis x residues", Glycobiology, vol. 16, No. 3 (2006) pp. 197-209.
Brigl, et al., "Uber Derivate der 1-Aminoglucose", Hoppe-Seyler's Z. Physiol. Chem. 180 (1929) 38-63.
Bruyn et al.,"1 H-N.m.r. study of L-rhamnose, methyl . . . deuterium oxide", Carbohydrate Research, 1976, 47, pp. 158-163.

(Continued)

*Primary Examiner* — Patrick Lewis
(74) *Attorney, Agent, or Firm* — Norton Rose Fulbright US LLP; Scott D. Rothenberger

(57) ABSTRACT

The present invention is directed to sulphated compounds comprising at least one glycosidic amine group, and polysaccharide, oligosaccharide, peptide and protein derivatives comprising such compounds, and mixtures thereof. The present invention is also directed to methods of synthesizing such compounds. Such compounds may bind to a range of proteins, find application in methods of modifying, or testing for a modification in the level of a cytokine in vivo, ex vivo or in vitro, and find application in the treatment and/or prevention of inflammation, an inflammatory disorder, a proliferative disorder, an immune disorder, an angiogenesis-dependent disorder, a sensitivity disorder, an adverse endocrine reaction, a degenerative disorder, wound healing, depression, and other diseases and disorders.

19 Claims, 13 Drawing Sheets

(56) References Cited

OTHER PUBLICATIONS

Cahalon et al., "Heparin disaccharides inhibit tumor necrosis . . . arrest immune inflammation in rodents", Int'l Immunology, 1997, 9(10), pp. 1517-1522.
Chhabra et al., "Recent Progress in the Design of Selectin Inhibitors", Mini Rev Med Chem, 3 (2003) 679-687.
Chower et al, "Disaccharides Derived From Heparin or Heparan Sulfate Regulate IL-8 and IL-1B Secretion by Intestinal Epithelial Cells", Gastroenterology, 2001, 120, pp. 449-459.
Dawes et al., "Human Vascular Endothelial Cells . . . Novel Route", Thrombosis and Haemostasis, 1992, 67(4), pp. 468-472.
Forsten et al., "A simple assay for evaluating inhibitors of proteoglycan-ligand binding", Ann. Biomed. Eng. 28(1) (2000), 119-27 Abstract Only.
Gama et al., "Sulfation patterns . . . and activity", Nature Chemical Biology, 2006, vol. 2(9), pp. 467-473.
Gil-Fernandez et al., "Antiviral Activity . . . in cell culture", Antiviral Research, 1987, vol. 8, pp. 299-310.
Hadjiloi et al., "Binding of oxalyl derivatives . . . ", Bioorg. Med. Chem., 2006, article in press copy.
Hecht, et al., "Heparin-disaccharide affects . . . signalling", J. of Leukocyte Biology, 2004, vol. 75, pp. 1139-1146.
Hershkoviz, et al., "Disaccharides generated from . . . matrix", Immunology, 2000, 99, pp. 87-93.
Hiebert et al., "Tissue Distribution . . . to rats", Pharm. Res., 2002, vol. 19(6), pp. 838-844.
Hung et al. "Molecular cloning . . . factor receptor", Biochem. Biophys. Res. Comm., 2004, vol. 317, pp. 253-258.
Innis et al., "Crystal Structures . . . of Follistatin", J. Biol. Chem., 2003, vol. 278(41), pp. 39969-39977.
Isbell et al., "Mutarotation, Hydrolysis . . . Glycosylamines", Glycosylamines, 1958, pp. 1309-1319.
Johnson et al., "Interface with Heparin Binding . . . System", J. of Immunology, 2004, 173, pp. 5776-5785.
Kajikawa et al., "Cellobiose Transport by Mixed Ruminal Bacteria from a Cow", App Environ Microbiol., 1999, 65(6), 2565-2569.
Kavlekar et al., "5-Thio-d-glycopyranosylamines . . . and molecular modelling", Tetrahedron: Asymmetry, 2005, 16, pp. 1035-1046.
Koch, "Experrilncntelle Untersuchungen . . . andere Pilze", Arch. klin. exp. Derm., 1957, Bd. 205, S1-21.
Kogelberg et al., "Binding of Sucrose Octasulphate . . . Observed by NMR Spectroscopy", ChemBioChem, 2002, vol. 3, pp. 1072-1077.
Kolarova et al., "Inhibitory effect of digluccosylamines . . . ", Carbohydrate Research, 273 (1995), pp. 109-114.
Lagrelius et al, "Cytokine detection by multiplex . . . " Cytokine, 2006, 33, pp. 156-165.
Lider et al., "A disaccharide that inhibits . . . ", Immunology, 1995, vol. 92, pp. 5037-5041.
Linek et al., "A structure of glycosylamines . . . ", Carbohydrate Research, 1993, 247, pp. 329-335.
Linek et al., "Glycosylamines III., Preparation . . . ", Chem. Papers, 1993, 47(4), pp. 247-250.
Lowe, "Glycosylation . . . structure and function", Immunological Reviews, 2002, vol. 186, pp. 19-36.
Magnani, "The discovery, biology . . . ", Arch. Biochem. Biophys., 2004, vol. 426, pp. 122-131.
Mizuguchi, et al., "Chondroitin proteogylcans . . . " Nature, 2003, 423, pp. 443-448.
Natl Toxicol Program Tech. Rep. Ser., 2004, 512, 7-289.
O'Harte et al., "Glycated Cholecystokinin-8 . . . ", Diabetes, 1998, vol. 47, pp. 1619-1624.
Ohki et al., Pestic Sci, 1999, 55, pp. 674-675.
Olson, et al., "Passive Transfer of Delayed-Type . . . ", Clin Immunol Immunopathol. (1981)1:19-34.
Presta et al., "Fibroblast growth . . . ", Cytokine & Growth Factor Reviews, 2005, 16, pp. 159-178.
Proudfoot et al., "Strategies for chemokine antagonists as therapeutics" Seminars in Immunology, 2003, 15, pp. 57-65.
Rinnbauer et al., "Epitope mapping of sialyl" . . . Glycobiology, 2003, vol. 13(6), pp. 435-443.
Roberts et al., "Safe Anti-Inflammatory Therapy . . . ", XXI Annual Meeting of the ACVO, Oct. 11-14, 1990, Scottsdale, AZ.
Romano, "Selectin Antagonists", Treat. Respir. Med. 4(2) (2005) 85-94.
Seed, 7th World Congress on Inflammation, 2005, poster and abstract.
Shaw et al., "The X-Ray Structure of RANTES . . . ", Structure, 12, 2004, pp. 2081-2089.
Sugahara, K. et al., "Recent advances in the structural biology of chohdroitin . . . ", Curr. Opin. Structural Biol. 2003, 13, 612-620.
Tully, S., "A Chondroitin Sulfate Small Molecule . . . ", J. Am. Chem. Soc. 2004, 126, 7736-7737.
Varki et al., "Siglecs—the major subfamily of I-Type lectins", Glycobiology, 2006, vol. 16(1), pp. 1 R-27R).
Venkatachalam et al., "Protein Chemistry and Structure", J. Biol. Chem., 1998, vol. 273(30), 19311-19320.
Vetter et al., "A Versatile Solid-Phase Synthesis of N-Linked Glycopeptides", Angew. Chem. Int. Ed. Engl., 1995, 34(1), pp. 60-63.
Vetter et al., "Stratagies for the synthesis and . . . ", Biconjugate Chem. 1995, vol. 6(3), pp. 316-318.
Vetter et al., "Stratagies for the synthesis and", Biconjugate Chem. 1995, vol. 6(3), p. 319 only.
Waitz, et al., "Comparative Activity of Sisomicin . . . " Antimicrob Agents Chemother., 1972, 6:431-7.
Walsh et al., "Heparin and heparin sulphate . . . ", Clinical Sci. 1991, 81, pp. 341-346.
Yan et al., "Synthesis of a lipid conjugate . . . ", Bioconjugate Chemistry, 2005, vol. 16, pp. 90-96.
Yeh et al., "Structural Basis for Activiation . . . ", Mol. Cell. Biology, 2002, vol. 22(20), pp. 7184-7192.
Yonghao et al., "Potential Inhibitors of Chemokine Function . . . ", J. Am. Soc. Mass Spectrometry, 17, (2006), pp. 524-535.
Yonghao et al., "Glycobiology and Extracellular Matrices", J. Biol. Chem., 280(37), 2005, pp. 32200-32208.
Zittermann et al., "Identification and dynamics of a heparin-binding . . . ", Ame. J. of Pathology, 2006, vol. 168(3), pp. 835-846.
Zhou et al., "Basic Fibroblast Growth Factor . . . ", Biochemistry, 38(45) (1999), 14793-802. Abstract Only.
Erickson, "Sulfated 1-alkylurea 3-glycosides" CAPLUS 1958:13512.
Koch, "Experimental investigations of the influence of new sulfonamides on dermatophytes and other fungi", CAPLUS 1958:94051.
Gil-Fernandez, et al., "Antiviral activity of uridine 5'-diphosphate glucose analogs against some enveloped viruses in cell culture", CAPLUS 1988:179598.
Fernandez-Resa, et al., "Process for the preparation of 5'-0-(glycosylureidosulfonyl)uridine derivatives with potential antiviral activity", CAPLUS 1988:493539.
Vetter , et al., "A versatile solid-phase synthesis of N-linked glycopeptides", CAPLUS 1995:329599.
Vetter, et al., "Strategies for the Synthesis and Screening of Glycoconjugates. 1. A Library of Glycosylamines", CAPLUS 1995:568710.
Schlessinger, et al., "Methods for treating cancer and other cell proliferative diseases", CAPLUS 1996:137695.
Srivastava, et al., "Preparation of oligosaccharide glycosides having mammalian immunosuppressive and tolerogenic properties", CAPLUS 1997:436104.
Nagy, et al., "Inhibition of cell-cell binding by glycoliposomal lipid assemblies", CAPLUS 1998:608530.
O'harte, et al., "Glycated cholecystokinin-8 has an enhanced satiating activity and is protected against enzymic degradation", CAPLUS 1998:630442.
Srivastava, et al., "Preparation of oligosaccharide glycosides antiinflammatory agents having mammalian immunosuppressive and tolerogenic properties", CAPLUS 1999:136759.
Babczinski, "Plant cell cultures as a model for the biochemistry of crop selectivity", CAPLUS 1999:401516.
Yan, et al., "Synthesis of a Lipid Conjugate of S03Lea and Its Enhancement on Liposomal Binding to Activated Platelets", CAPLUS 2004:1153529.

(56) References Cited

OTHER PUBLICATIONS

Don et al., "Preparation of glycosaminoglycan (GAG) mimetics as anti-angiogenic, anti-metastatic, anti-inflammatory, anticoagulant, antithrombotic, and antimicrobial agents", CAPLUS 2005:588998.

Evans, "Inflammatory Bowel Disease", Gastrointestinal disorders, Ch. 11, 2000, pp. 163-178.

Linek et al., "Structure and Rearrangement Reactions of Some Diglycosylamines", Carbohydrate Chemistry, 1987, vol. 164, pp. 195-205.

Merck & Co., Inc., "N4-β-D-Glucosylsulfanilamide", The Merck Index, 2006, 1 page.

Vetter et al., "Strategies for the Synthesis and Screening of Glycoconjugates. 2. Covalent Immobilization for Flow Cytometry", Biconjugate Chem. 1995, vol. 6(3), pp. 319-322.

* cited by examiner

COMPOUNDS

CROSS-REFERENCE TO RELATED APPLICATION(s)

This application is a Section 371 National Stage Application of International No. PCT/EP2007/062355, filed 14 Nov. 2007 and published as WO 2008/059003 A1 on 22 May 2008, which claims priority from the GB Patent Application No. 0622688.0, filed Nov. 14, 2006, and GB Patent Application No. 0711138.8, filed on Jul. 11, 2007, the contents of which are incorporated herein in their entirety for all purposes.

TECHNICAL FIELD

The present invention is directed to sulphated compounds comprising at least one glycosidic amine group, and polysaccharide, oligosaccharide, peptide and protein derivatives comprising such compounds, and mixtures thereof. The present invention is also directed to methods of synthesising such compounds. Such compounds may bind to a range of proteins, find application in methods of modifying, or testing for a modification in the level of a cytokine in vivo, ex vivo or in vitro, and find application in the treatment and/or prevention of inflammation, an inflammatory disorder, a proliferative disorder, an immune disorder, an angiogenesis-dependent disorder, a sensitivity disorder, an adverse endocrine reaction, a degenerative disorder, wound healing, depression, and other diseases and disorders.

BACKGROUND ART

Anti-inflammatory agents, such as corticosteroids, aminosalicylates, azathioprine, metronidazole and cyclosporin, are widely known and used to treat conditions such as inflammatory bowel disease. The use of carbohydrate-derived compounds to treat such conditions is, however, an emerging science.

One of the best-studied examples is that of the tetrasaccharide Sialyl Lewis$^X$ 1, both as a stand-alone molecule and as part of larger oligosaccharides and glycoproteins.

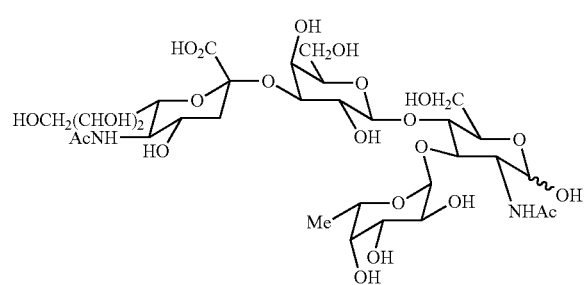

1

A review by Lowe in 2002 (*Immunological Reviews*, 186, (2002), pp. 19-36), for instance, has highlighted the role Sialyl Lewis$^X$ capped glycoproteins, and in particular 6-O-GlcNAc sulphate-modified derivatives, play in selectin counter-receptor activity by binding to selectins.

Selectins, in particular E-, P- and L-selectins, are proteins responsible for the initial recognition and adhesion of leukocytes to the vascular endothelium. This in turn influences the immune response at sites of chronic inflammation.

The inhibition of E-selectin expression has also been shown to dramatically improve patient survival rates, whilst the expression of Sialyl Lewis$^X$ and the similar Sialyl Lewis$^A$ (a trisaccharide lacking the terminal L-fucosyl group of Sialyl Lewis$^X$) has been implicated as a marker for metastasis and tumour progression in cancer patients (see the review by J. L. Magnani, *Archiv. Biochem. Biophys.*, 426, (2004), pp. 122-131).

It has also been demonstrated that, in addition to the selectin binding discussed above, 6-O-GlcNAc sulphate-modified Sialyl Lewis$^X$ derivatives may bind to certain Siglecs (sialic acid recognising, Ig-superfamily lectins), playing a role in, for example, intracellular signalling and cell-cell interactions (see Varki et al, *Glycobiology*, 16(1), (2006), pp. 1R-27R).

Thus, inhibitory analogues of Sialyl Lewis$^X$ have become key targets in the search for new classes of drugs. To date, successful inhibitors of selectins derived by this route include the E-selectin inhibitor 2 and the P-selectin inhibitor 3 (see Magnani).

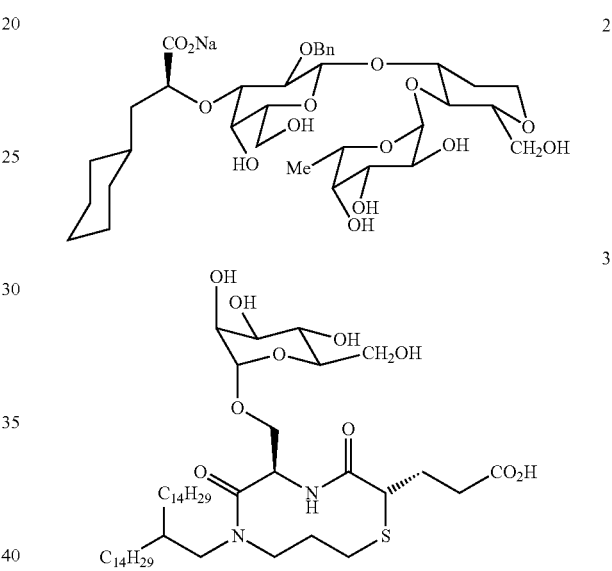

There is still a need, however, for further selectin inhibitors to be developed; sulphated glycosylamines remain unexplored in this respect.

A number of glycosylamines are known to be biologically active, for example, di-β-D-glucosylamine 4 has been shown to inhibit β-glucosidases (Kolarova et al, *Carbohydrate Research*, 273, (1995), pp. 109-114), although this activity was greatly reduced when N-acetylated.

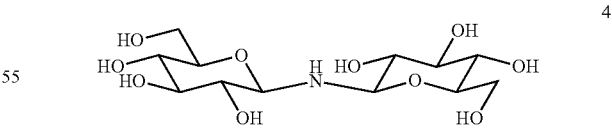

This compound has also been implicated as an anti-inflammatory agent (see U.S. Pat. No. 5,631,245). When administered to mice by parenteral routes, it inhibits articular inflammation (Bolton et al, *Inflamm. Res.*, Suppl. 2, (2005), p. S121), however it is inactive when given by the oral route, the glycosylamine group being readily hydrolysed under the acid conditions of the stomach. Although the mechanism by which it operates is not clear, it inhibits antigen induced immune cell proliferation and interleukin-2, interleukin-10 and IFN synthesis by antigen stimulated mice spleen cells in vitro. These actions are consistent with an anti-inflammatory and anti-immune profile of activity. In addition, di-β-D-glucosylamine prevents the development of ocular inflammation resulting from the reactivation of feline herpes infection (Roberts et al, XII Annual Meeting of the ACVO, Oct. 11-14, 1990, Scottsdale, Ariz.).

Sulphated carbohydrate derivatives, other than the sulphate-modified Sialyl Lewis$^X$ derivatives discussed above, have been explored for a wide variety of reasons. For instance, there is a class of sulphated glycosaminoglycan binding proteins, which perform a vast array of functions and are capable of recognising, for example, the subgroups of the naturally occurring heparan sulphate, dermatan sulphate or chondroitin sulphate (with repeating subgroup 5) glycosaminoglycans. Chondroitin sulphate reduces inflammatory cell accumulation and inflammation in inflamed joints (Ronca et al, Osteoarthritis and Cartilage, 6(Suppl. A), (1998), pp. 14-21).

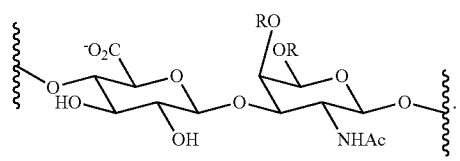

R = H or SO$_3$-

At the other end of the spectrum, a number of sulphated mono- and di-saccharides are well known and possess a range of biological activities. Perhaps the most extensively studied of these (primarily due to its low cost) is sucrose octasulphate. U.S. Pat. No. 5,202,311 for instance discloses the use of sucrose octasulphate and its aluminium/sodium salts for the stabilisation of fibroblast growth factor (FGF) and the use of the resultant composition to treat gastrointestinal ulcerations and other diseases responsive to FGF therapy. This stabilisation and resultant signalling has been hypothesised to be the result of sucrose octasulphate induced FGF dependent dimerisation of FGF receptors via the formation of a ternary complex in which sucrose octasulphate binds to both FGF and FGF receptors (Yeh et al, Mol. Cell. Biology, 22(20), (2002), pp. 7184-7192). Interestingly, the same study noted that the dimerisation occurred to a much lesser extent or not at all with 2-hydroxysucrose heptasulphate and 4,6-dihydroxysucrose hexasulphate respectively.

However, the enhancement of such FGF activity by sulphated carbohydrates is unlikely to result in anti-inflammatory activity, indeed FGF itself does not induce cell inflammatory cell recruitment, but when given with inflammatory cytokines such as tumour necrosis factor interferon, C5a or delayed-type hypersensitivity, it enhances inflammation (Zittermann et al, American Journal of Pathology, 168(3), (2006), pp. 835-846). In addition, FGF is intimately involved in the process of angiogenesis (Presta et al, Cytokine and Growth Factor Reviews, 16, (2005), pp. 159-178), and this is enhanced by heparinoid compounds. Angiogenesis is required for the development of chronic inflammatory tissues, but is also required for wound healing.

Sucrose octasulphate has also been shown to bind to the C-type lectin-like domain of a recombinant natural killer cell receptor (Kogelberg et al, Chem. Bio. Chem., 3, (2002), pp. 1072-1077), to a hepatocyte growth factor (Zhou et al, Biochemistry, 38(45), (1999), pp. 14793-14802), to follistatin (Innis et al, J. Biol. Chem., 278(41), (2003), pp. 39969-39977), and the pro-inflammatory chemokine MCP-1 (Yonghao et al, J. Am. Soc. Mass Spectrometry, 17, (2006), pp. 524-535; Yonghao et al, J. Biol. Chem., 280(37), (2005), pp. 32200-32208).

Sulphated oligosaccharides reduce inflammatory cell rolling and accumulation through the interference with P- and L-selectins (Walsh et al, Clinical Science, 81(3), (1991), pp. 341-346), and heparin-derived disaccharides purified from porcine blood inhibit murine macrophage tumour necrosis factor synthesis and inflammation (Cahalon et al, Int. Immunol., 9(10), (1997), pp. 1517-1522). Such sulphated disaccharides can bind chemokines that are involved in cell recruitment (Shaw et al, Structure, 12, (2004), pp. 2081-2089).

The biological activity of sucrose octasulphate has largely been explained to be a result of its ability to mimic the binding of the glycosaminoglycans heparan sulphate and heparin sulphate. Notably, however, studies on the isolated disaccharide 4-deoxy-α-L-threo-hex-4-ene-pyranosyluronic acid (1-4)-2-amino-2-deoxy-2,6-di-O-sulpho-glucopyranose, which is repeatedly present in heparin, have not always shown the same binding ability (see Kogelberg et al).

Also of note is the fact that sulphated glycosaminoglycans are desulphated to their constituent carbohydrates by vascular endothelium, and inactivated (Dawes & Pepper, Thrombosis and Haemostasis, 67(4), (1992), pp. 468-472). Indeed, desulphated heparin disaccharide O-(α-L-ido-4-enepyranosyluronic acid)-(1→4)-2-deoxy-N-acetyl-D-glucoseamine is ineffective as an anti-inflammatory agent (Cahalon et al, Int. Immunol., 9(10), (1997), pp. 1517-1522), unlike di-β-D-glucosylamine which possesses inherent anti-inflammatory activity (see Bolton et al).

Sulphated monosaccharides are known to occur in nature. One such monosaccharide is 3'-phosphoadenosine-5'-phosphosulphate (PAPS), 6.

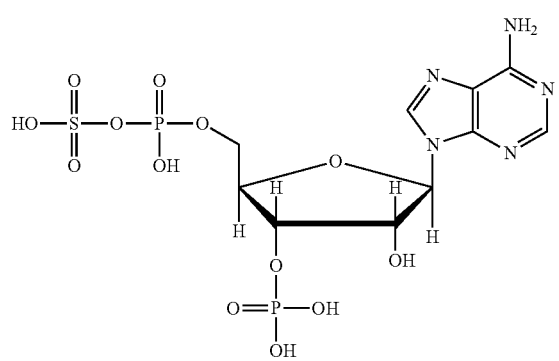

PAPS is active throughout the mammalian metabolism, where it has been identified as an activated sulphate molecule which represents the universal sulphonate donor for all sulphotransferase reactions. It therefore performs an essential role within the body, acting for instance to sulphonate the glycosaminoglycans referred to above, or to sulphonate xenobiotics in order to make them more hydrophilic and thereby encourage their excretion from the body (Venkatachalam et al, J. Biol. Chem., 273(30), (1998), pp. 19311-19320).

SUMMARY OF THE INVENTION

A first aspect of the present invention provides a compound comprising:

(i) at least one monosaccharide subunit comprising a glycosidic —$NR_2$ group, a glycosidic —$NR_3^+$ group, a directly bonded =NR group, or a directly bonded =$NR_2^+$ group, wherein each R is independently hydrogen, a —$SO_2$—OR' or —$SO_2$—N(R')$_2$ group, a further monosaccharide subunit, or a hydrocarbyl group, or two or three R groups and the nitrogen atom to which they are attached, together form a further monosaccharide subunit or a cyclic hydrocarbyl group; and (ii) at least one sulphate group, wherein a sulphate group is a —O—$SO_2$—OR', —NR'—$SO_2$—OR', —O—$SO_2$—N(R')$_2$ or —NR'—$SO_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the compound is not 3'-phosphoadenosine-5'-phosphosulphate.

Alternatively, the first aspect of the present invention provides a compound comprising:

(i) at least one monosaccharide subunit comprising a glycosidic —$NR_2$ group, a glycosidic —$NR_3^+$ group, a directly bonded =NR group, or a directly bonded =$NR_2^+$ group, wherein each R is independently hydrogen, a —$SO_2$—OR' or —$SO_2$—N(R')$_2$ group, a further monosaccharide subunit, or a hydrocarbyl group, or two or three R groups and the nitrogen atom to which they are attached, together form a further monosaccharide subunit or a cyclic hydrocarbyl group, provided that the glycosidic —$NR_2$ group is not —NHacyl; and (ii) at least one sulphate group, wherein a sulphate group is a —O—$SO_2$—OR', —NR'—$SO_2$—OR', —O—$SO_2$—N(R')$_2$ or —NR'—$SO_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the compound is not 3'-phosphoadenosine-5'-phosphosulphate; and provided that the at least one monosaccharide subunit is not substituted with an —OR''' group, wherein R''' is any group comprising a further pyranosyl or furanosyl monosaccharide subunit.

Alternatively, the first aspect of the present invention provides a compound comprising:

(i) at least one monosaccharide subunit comprising a glycosidic —$NR_2$ group, a glycosidic —$NR_3^+$ group, a directly bonded =NR group, or a directly bonded =$NR_2^+$ group, wherein each R is independently hydrogen, a —$SO_2$—OR' or —$SO_2$—N(R')$_2$ group, a further monosaccharide subunit, or a $C_1$-$C_7$ hydrocarbyl group, or two or three R groups and the nitrogen atom to which they are attached, together form a further monosaccharide subunit or a cyclic hydrocarbyl group; and (ii) at least one sulphate group, wherein a sulphate group is a —O—$SO_2$—OR', —NR'—$SO_2$—OR', —O—$SO_2$—N(R')$_2$ or —NR'—$SO_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the compound is not 3'-phosphoadenosine-5'-phosphosulphate; and provided that the at least one monosaccharide subunit is not substituted with an —OR''' group, wherein R''' is any group comprising a further pyranosyl or furanosyl monosaccharide subunit.

Alternatively, the first aspect of the present invention provides a compound comprising:

(i) at least one monosaccharide subunit comprising a glycosidic —$NR_2$ group, a glycosidic —$NR_3^+$ group, a directly bonded =NR group, or a directly bonded =$NR_2^+$ group, wherein each R is independently hydrogen, a —$SO_2$—OR' or —$SO_2$—N(R')$_2$ group, a further monosaccharide subunit, or a $C_1$-$C_7$ hydrocarbyl group, or two or three R groups and the nitrogen atom to which they are attached, together form a further monosaccharide subunit or a cyclic hydrocarbyl group; and (ii) at least one sulphate group, wherein a sulphate group is a —O—$SO_2$—OR', —NR'—$SO_2$—OR', —O—$SO_2$—N(R')$_2$ or —NR'—$SO_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the at least one monosaccharide subunit is not N-substituted a to said glycosidic —$NR_2$ group, glycosidic —$NR_3^+$ group, directly bonded =NR group, or directly bonded =$NR_2^+$ group.

In one embodiment of any compound of the first aspect of the present invention, the glycosidic —$NR_2$ group is not —NHacyl, the glycosidic —$NR_3^+$ group is not —$NH_2$acyl$^+$, the directly bonded =NR group is not =Nacyl, and/or the directly bonded =$NR_2^+$ group is not =NHacyl$^+$.

In one embodiment of any compound of the first aspect of the present invention, the at least one monosaccharide subunit is not substituted with an —OR''' group, wherein R''' is any group comprising a further pyranosyl or furanosyl monosaccharide subunit. Alternatively, R''' may be any group comprising a further 5- or 6-membered ring-closed monosaccharide subunit. Alternatively, R''' may be any group comprising a further pentosyl, hexosyl or higher monosaccharide subunit. Alternatively still, R''' may be any group comprising a further monosaccharide subunit.

Preferably the compound of the first aspect of the present invention comprises at least one monosaccharide subunit comprising a glycosidic —$NR_2$ group or a glycosidic —$NR_3^+$ group, or a tautomer or thereof.

For the purposes of the present invention, the term 'directly bonded' used in relation to a monosaccharide subunit comprising a group, means that the group is bonded to the carbon backbone of the monosaccharide subunit without any intervening atoms being present.

A second aspect of the present invention provides a compound comprising:

(i) a sequence of at least two monosaccharide subunits linked by a glycosidic —NR— group, a glycosidic —$NR_2^+$— group, a directly bonded =N— group, or a directly bonded =$NR^+$— group, wherein each R is independently hydrogen, a —$SO_2$—OR' or —$SO_2$—N(R')$_2$ group, a further monosaccharide subunit, or a hydrocarbyl group, or two R groups and the nitrogen atom to which they are attached, together form a further monosaccharide subunit or a cyclic hydrocarbyl group; and (ii) at least one sulphate group, wherein a sulphate group is a —O—$SO_2$—OR', —NR'—$SO_2$—OR', —O—$SO_2$—N(R')$_2$ or —NR'—$SO_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof.

Preferably the compound of the second aspect of the present invention comprises:

(i) a sequence of at least two monosaccharide subunits linked by a glycosidic —NR— group or a glycosidic —$NR_2^+$— group, wherein each R is independently hydrogen, a —$SO_2$—OR' or —$SO_2$—N(R')$_2$ group, a further monosaccharide subunit, or a hydrocarbyl group, or two R groups and the nitrogen atom to which they are attached, together form a further monosaccharide subunit or a cyclic hydrocarbyl group; and (ii) at least one sulphate group, wherein a sulphate group is a —O—$SO_2$—OR', —NR'—$SO_2$—OR', —O—$SO_2$—N(R')$_2$ or —NR'—$SO_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a tautomer or a salt thereof.

The at least two monosaccharide subunits are directly linked by the glycosidic —NR— group, the glycosidic —$NR_2^+$— group, the directly bonded =N— group, or the directly bonded =$NR^+$— group, such that the group is directly bonded to both monosaccharide subunits without any intervening atoms being present, such that the compounds of the second aspect of the present invention are or comprise poly- or oligosaccharides. The glycosidic —NR— group or the glycosidic —$NR_2^+$— group may be linked to one or both of the monosaccharide subunits by a glycosidic bond. The directly bonded =N— group or the directly bonded =$NR^+$— group may be linked to one or neither of the monosaccharide subunits by a glycosidic bond.

For the purposes of the present invention, a 'saccharide' is any compound comprising at least one monosaccharide subunit, optionally substituted and/or optionally modified. Thus, by this definition, a compound of the present invention is a saccharide. A saccharide may be a mono-, oligo- or polysaccharide. An 'oligosaccharide' may comprise between 2 and 10 monosaccharide subunits and may therefore be a disaccharide, trisaccharide, tetrasaccharide, pentasaccharide, hexasaccharide, heptasaccharide, octasaccharide, nonasaccharide, or decasaccharide. A 'polysaccharide' may comprise 11 or more monosaccharide subunits.

For the purposes of the present invention, the term 'monosaccharide subunit' refers to a monosaccharide optionally substituted and/or optionally modified, which may or may not be part of a compound comprising more than one monosaccharide subunit. Thus, for the avoidance of doubt, it is noted that the present invention covers compounds comprising just one monosaccharide subunit, such as monosaccharides.

For the purposes of the present invention, where a compound 'contains x monosaccharide subunits', this means that the compound has x monosaccharide subunits and no more, unless it is explicitly mentioned that the compound contains or comprises further monosaccharide subunits. In contrast, where a compound 'comprises x monosaccharide subunits', this means that the compound has x or more monosaccharide subunits.

The single bond between an anomeric carbon of a monosaccharide subunit and a substituent is called a glycosidic bond. A glycosidic group is linked to the anomeric carbon of a monosaccharide subunit by a glycosidic bond. One distinguishes between α- and β-glycosidic bonds depending on whether the participating anomeric carbon is in the α or β configuration. In the standard Haworth way of drawing monosaccharide subunits, an α-glycosidic bond of a D-monosaccharide subunit emanates below the plane of the monosaccharide subunit and a β-glycosidic bond emanates above that plane, and vice versa for an L-monosaccharide subunit.

For the purposes of the present invention, a 'glycosylamine' is any compound comprising at least one monosaccharide subunit with a glycosidic amine group. Thus, by this definition, a compound of the present invention is a glycosylamine. A 'glucosylamine' is any compound comprising at least one glucose subunit with a glycosidic amine group. A 'β,β-di-glucosylamine' is any compound comprising at least two glucose subunits linked by a β,β-glycosidic amine group. A β,β-glycosidic amine group is linked to the anomeric carbons of two monosaccharide subunits, with both glycosidic bonds being β-glycosidic bonds.

All monosaccharide subunits are independently ring-closed or open-chain or a mixture of ring-closed and open-chain. Ring-closed and open-chain monosaccharide subunits are tautomers of each other, which exist in their cyclic and acyclic forms respectively (with respect to the portion of the molecule referred to). For example, in the equilibrium below, A is the open-chain tautomer and B is the ring-closed tautomer:

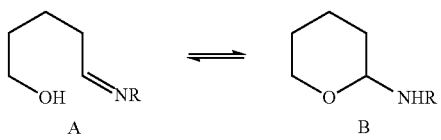

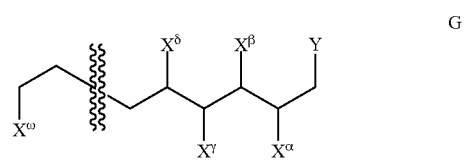

Thus, in the context of the present invention, it is understood that any substituent that contains a hydrogen atom of moderate acidity (e.g. a hydroxyl, amino or thiol group proton) may interact with the π-bond illustrated so as to establish the above equilibrium. A 'hydrogen atom of moderate acidity' is defined as one with an approximate $pK_a$ (relative to water) of less than 40, preferably less than 30, preferably less than 25, preferably less than 20. It is also understood that in some cases it is not possible to establish the above equilibrium due to a lack of a suitable hydrogen atom and the relevant portion of the molecule is effectively 'locked' in its open-chain form. In other cases, the relevant portion of the molecule will exist predominantly in its ring-closed form with little or none of the open-chain form being detectable. It is also to be understood that more than one equilibrium may be established within a given portion of the molecule, for example, the scenario below may be established, wherein the molecule exists in two ring-closed forms C and E, and one open-chain form D:

The following paragraphs apply equally to the compounds of the first and second aspects of the present invention.

In one embodiment of the present invention, none of the monosaccharide subunits is pyranosyl with N-substitution at the 2-position relative to the anomeric carbon of the pyranosyl subunit. Preferably none of the monosaccharide subunits is N-substituted α to the anomeric carbon.

In one embodiment of the present invention, none of the monosaccharide subunits is pyranosyl with a —$CO_2Q$ group attached to the 5-position relative to the anomeric carbon of the pyranosyl subunit, wherein Q is hydrogen or a hydrocarbyl group. Preferably, none of the monosaccharide subunits has a —$CO_2Q$ group attached to the 5-position and/or the ω-position relative to the anomeric carbon of the monosaccharide subunit. Preferably, none of the monosaccharide subunits is substituted with a —$CO_2Q$ group.

Each monosaccharide subunit independently may be substituted and/or modified.

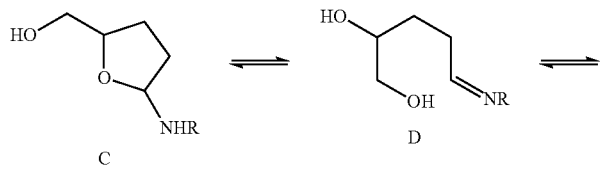

A pyranosyl monosaccharide subunit is a cyclic saccharide with a six-membered ring. Pyranosyl monosaccharide F shown below has been marked with substituent X in the 2-position relative to the anomeric carbon of the pyranosyl subunit:

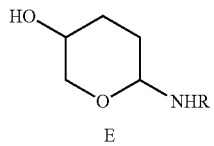

As used herein, where it is specified that a first group is located α to a second group, this means that the first group is attached to a carbon atom one bond removed from the carbon atom to which the second group is attached. Similarly, where it is specified that a first group is located β to a second group, this means that the first group is attached to a carbon atom two bonds removed from the carbon atom to which the second group is attached, and so on for groups located γ, δ etc. Where it is specified that a first group is located ω to a second group, this means that the first group is attached to the furthest carbon atom removed, along a continuous chain of carbon atoms, from the carbon atom to which the second group is attached. Formula G below has been marked with substituents X in the α-, β-, γ-, δ- and ω-positions relative to the group Y:

In a substituted monosaccharide subunit:

(a) independently one or more of the hydroxyl groups of the monosaccharide subunit is replaced with —H, —F, —Cl, —Br, —I, —$CF_3$, —$CCl_3$, —$CBr_3$, —$CI_3$, —SH, —$NH_2$, —$N_3$, —NH=$NH_2$, —CN, —$NO_2$, —COOH, —$R^a$—O—$R^b$, —$R^a$—S—$R^b$, —$R^a$—SO—$R^b$, —$R^a$—$SO_2$—$R^b$, —$R^a$—$SO_2$—$OR^b$, —$R^aO$—$SO_2$—$R^b$, —$R^a$—$SO_2$—$N(R^b)_2$, —$R^a$—$NR^b$—$SO_2$—$R^b$, —$R^aO$—$SO_2$—$OR^b$, —$R^aO$—$SO_2$—$N(R)_2$, —$R^a$—$NR^b$—$SO_2$—$OR^b$, —$R^a$—$NR^b$—$SO_2$—$N(R^b)_2$, —$R^a$—$N(R^b)_2$, —$R^a$—$N(R^b)_3^+$, —$R^a$—$B(R^b)_2$, —$R^a$—$P(R^b)_2$, —$R^a$—$PO(R^b)_2$, —$R^a$—$Si(R^b)_3$, —$R^a$—CO—$R^b$, —$R^a$—CO—$OR^b$, —$R^aO$—CO—$R^b$, —$R^a$—CO—$N(R^b)_2$, —$R^a$—$NR^b$—CO—$R^b$, —$R^aO$—CO—$OR^b$, —$R^aO$—CO—$N(R^b)_2$, —$R^a$—$NR^b$—CO—$OR^b$, —$R^a$—$NR^b$—CO—$N(R)_2$, —$R^a$—CS—$R^b$, —$R^a$—CS—$OR^b$, —$R^aO$—CS—$R^b$, —$R^a$—CS—$N(R^b)_2$, —$R^a$—$NR^b$—CS—$R^b$, —$R^aO$—CS—$OR^b$, —$R^aO$—CS—$N(R^b)_2$, —$R^a$—$NR^b$—CS—$OR^b$, —$R^a$—$NR^b$—CS—$N(R^b)_2$, or —$R^b$;

preferably independently one or more of the hydroxyl groups of the monosaccharide subunit is replaced with —H, —F, —Cl, —Br, —I, —$CF_3$, —$CCl_3$, —$CBr_3$, —$CI_3$, —SH, —$NH_2$, —$N_3$, —NH=$NH_2$, —CN, —$NO_2$, —COOH, —$R^a$—O—$R^b$, —$R^a$—S—$R^b$, —SO—$R^b$, —$SO_2$—$R^b$, —$SO_2$—$OR^b$, —O—$SO_2$—$R^b$, —O—$SO_2$—$OR^b$, —$R^a$—$N(R^b)_2$, —$R^a$—$N(R^b)_3^+$, —$R^a$—$Si(R^b)_3$, —$R^a$—CO—$R^b$, —$R^a$—CO—$OR^b$, —$R^aO$—CO—$R^b$, —$R^a$—CO—$N(R^b)_2$, —$R^a$—$NR^b$—CO—$R^b$, —$R^aO$—CO—$OR^b$, —$R^a$—CS—$R^b$, or —$R^b$; and/or (b) independently one, two or three of the hydrogens of the monosaccharide subunit is replaced with —F, —Cl, —Br,

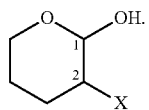

—I, —$CF_3$, —$CCl_3$, —$CBr_3$, —$CI_3$, —OH, —SH, —$NH_2$, —$N_3$, —NH=$NH_2$, —CN, —$NO_2$, —COOH, —$R^a$—O—$R^b$, —$R^a$—S—$R^b$, —$R^a$—SO—$R^b$, —$R^a$—$SO_2$—$R^b$, —$R^a$—$SO_2$—$OR^b$, —$R^aO$—$SO_2$—$R^b$, —$R^a$—$SO_2$—N($R^b$)$_2$, —$R^a$—$NR^b$—$SO_2$—$R^b$, —$R^aO$—$SO_2$—$OR^b$, —$R^aO$—$SO_2$—N(R)$_2$, —$R^a$—$NR^b$—$SO_2$—$OR^b$, —$R^a$—$NR^b$—$SO_2$—N($R^b$)$_2$, —$R^a$—N($R^b$)$_2$, —$R^a$—N($R^b$)$_3{}^+$, —$R^a$—B($R^b$)$_2$, —$R^a$—P(R)$_2$, —$R^a$—PO($R^b$)$_2$, —$R^a$—Si($R^b$)$_3$, —$R^a$—CO—$R^b$, —$R^a$—CO—$OR^b$, —$R^aO$—CO—$R^b$, —$R^a$—CO—N($R^b$)$_2$, —$R^a$—$NR^b$—CO—$R^b$, —$R^aO$—CO—$OR^b$, —$R^aO$—CO—N($R^b$)$_2$, —$R^a$—$NR^b$—CO—$OR^b$, —$R^a$—$NR^b$—CO—N($R^b$)$_2$, —$R^a$—CS—$R^b$, —$R^a$—CS—$OR^b$, —$R^aO$—CS—$R^b$, —$R^a$—CS—N($R^b$)$_2$, —$R^a$—$NR^b$—CS—$R^b$, —$R^aO$—CS—$OR^b$, —$R^aO$—CS—N($R^b$)$_2$, —$R^a$—$NR^b$—CS—$OR^b$, —$R^a$—$NR^b$—CS—N($R^b$)$_2$, or —$R^b$;

preferably independently one, two or three of the hydrogens of the monosaccharide subunit is replaced with —F, —Cl, —Br, —I, —$CF_3$, —$CCl_3$, —$CBr_3$, —$CI_3$, —OH, —SH, —$NH_2$, —$N_3$, —NH=$NH_2$, —CN, —$NO_2$, —COOH, —$R^a$—O—$R^b$, —$R^a$—S—$R^b$, —SO—$R^b$, —$SO_2$—$R^b$, —$SO_2$—$OR^b$, —O—$SO_2$—$R^b$, —$R^aO$—$SO_2$—$OR^b$, —$R^a$—N($R^b$)$_2$, —$R^a$—N($R^b$)$_3{}^+$, —$R^a$—Si($R^b$)$_3$, —$R^a$—CO—$R^b$, —$R^a$—CO—$OR^b$, —$R^aO$—CO—$R^b$, —$R^a$—CO—N($R^b$)$_2$, —$R^a$—$NR^b$—CO—$R^b$, —$R^aO$—CO—$OR^b$, —$R^a$—CS—$R^b$, or —$R^b$; and/or (c) independently one or more of the hydroxyl groups of the monosaccharide subunit, together with the hydrogen attached to the same carbon atom as the hydroxyl group, is replaced with =O, =S, =$NR^b$, or =N($R^b$)$_2{}^+$; and/or (d) independently two hydroxyl groups of the monosaccharide subunit are together replaced with —O—$R^c$—, —S—$R^c$—, —SO—$R^c$—, —$SO_2$—$R^c$—, or —$NR^b$—$R^c$—;

wherein:

—$R^a$— is independently a chemical bond, or a substituted or unsubstituted alkylene, alkenylene or alkynylene group which optionally includes one or more heteroatoms in its carbon skeleton and preferably comprises 1-10 carbon atoms;

—$R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises 1-15 carbon atoms;

—$R^c$— is independently a chemical bond, or a substituted or unsubstituted alkylene, alkenylene or alkynylene group which optionally includes one or more heteroatoms in its carbon skeleton and preferably comprises 1-10 carbon atoms; and M is a metal;

provided that the monosaccharide subunit comprises at least one, preferably at least two or at least three, —$OR^b$, —$OSOR^b$, —$OSO_2R^b$, —$OSO_3R^b$, —OSi($R^b$)$_3$, —$OCOR^b$, —$OCO_2R^b$, or —OM.

In a modified monosaccharide subunit:

(a) the ring of the modified monosaccharide subunit, or what would be the ring in the ring-closed form of the modified monosaccharide subunit, is partially unsaturated; and/or (b) the ring oxygen of the modified monosaccharide subunit, or what would be the ring oxygen in the ring-closed form of the modified monosaccharide subunit, is replaced with —S— or —$NR^b$—, wherein —$R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises 1-15 carbon atoms.

Each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton. Preferably a hydrocarbyl group comprises 1-30, 1-20, 1-15, 1-12, 1-6 or 1-4 carbon atoms. Preferably a hydrocarbyl group comprises 1-100, 1-50, 1-30, 1-20, 1-15, 1-10 or 1-6 atoms.

A substituted hydrocarbyl group may be substituted with one or more of —F, —Cl, —Br, —I, —$CF_3$, —$CCl_3$, —$CBr_3$, —$CI_3$, —OH, —SH, —$NH_2$, —$N_3$, —NH=$NH_2$, —CN, —$NO_2$, —COOH, —$R^a$—O—$R^b$, —$R^a$—S—$R^b$, —$R^a$—SO—$R^b$, —$R^a$—$SO_2$—$R^b$, —$R^a$—$SO_2$—$OR^b$, —$R^aO$—$SO_2$—$R^b$, —$R^a$—$SO_2$—N($R^b$)$_2$, —$R^a$—$NR^b$—$SO_2$—$R^b$, —$R^aO$—$SO_2$—$OR^b$, —$R^aO$—$SO_2$—N(R)$_2$, —$R^a$—$NR^b$—$SO_2$—$OR^b$, —$R^a$—$NR^b$—$SO_2$—N($R^b$)$_2$, —$R^a$—N($R^b$)$_2$, —$R^a$—N($R^b$)$_3{}^+$, —$R^a$—B(R)$_2$, —$R^a$—P($R^b$)$_2$, —$R^a$—PO($R^b$)$_2$, —$R^a$—Si($R^b$)$_3$, —$R^a$—CO—$R^b$, —$R^a$—CO—$OR^b$, —$R^aO$—CO—$R^b$, —$R^a$—CO—N($R^b$)$_2$, —$R^a$—$NR^b$—CO—$R^b$, —$R^aO$—CO—$OR^b$, —$R^aO$—CO—N($R^b$)$_2$, —$R^a$—$NR^b$—CO—$OR^b$, —$R^a$—$NR^b$—CO—N($R^b$)$_2$, —$R^a$—CS—$R^b$, —$R^a$—CS—$OR^b$, —$R^aO$—CS—$R^b$, —$R^a$—CS—N($R^b$)$_2$, —$R^a$—$NR^b$—CS—$R^b$, —$R^aO$—CS—$OR^b$, —$R^aO$—CS—N($R^b$)$_2$, —$R^a$—$NR^b$—CS—$OR^b$, —$R^a$—$NR^b$—CS—N($R^b$)$_2$, —$R^b$, or a monosaccharide subunit;

preferably a substituted hydrocarbyl group may be substituted with one or more of —F, —Cl, —Br, —I, —$CF_3$, —$CCl_3$, —$CBr_3$, —$CI_3$, —OH, —SH, —$NH_2$, —$N_3$, —NH=$NH_2$, —CN, —$NO_2$, —COOH, —$R^a$—O—$R^b$, —$R^a$—S—$R^b$, —SO—$R^b$, —$SO_2$—$R^b$, —$SO_2$—$OR^b$, —O—$SO_2$—$R^b$, —O—$SO_2$—$OR^b$, —$R^a$—N($R^b$)$_2$, —$R^a$—N($R^b$)$_3{}^+$, —$R^a$—Si($R^b$)$_3$, —$R^a$—CO—$R^b$, —$R^a$—CO—$OR^b$, —$R^aO$—CO—$R^b$, —$R^a$—CO—N($R^b$)$_2$, —$R^a$—$NR^b$—CO—$R^b$, —$R^aO$—CO—$OR^b$, —$R^a$—CS—$R^b$, —$R^b$, or a monosaccharide subunit;

wherein:

—$R^a$— is independently a chemical bond, or a substituted or unsubstituted alkylene, alkenylene or alkynylene group which optionally includes one or more heteroatoms in its carbon skeleton and preferably comprises 1-10 carbon atoms; and —$R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises 1-15 carbon atoms.

Any substituent, for example on a monosaccharide subunit or on a hydrocarbyl group, may be protected. Suitable protecting groups for protecting substituents are known in the art, for example from 'Protective Groups in Organic Synthesis' by Theodora W. Greene and Peter G. M. Wuts (Wiley-Interscience, 3$^{rd}$ edition, 1999).

In one embodiment, the compound of the present invention is a salt, preferably a pharmaceutically acceptable salt.

In one embodiment, the compound comprises at least one monosaccharide subunit comprising a glycosidic —$NR_2$ group or a directly bonded =NR group. In another embodiment, the compound comprises a sequence of at least two monosaccharide subunits linked by a glycosidic —NR— group or a directly bonded =N— group.

In preferred embodiments of the present invention:
(a) one R group is not hydrogen; and/or
(b) two R groups are not hydrogen; and/or
(c) one R group is a monosaccharide subunit and one R group is a hydrocarbyl group; and/or
(d) one R group is a monosaccharide subunit and one R group is hydrogen; and/or
(e) one R group is a hydrocarbyl group and one R group is hydrogen; and/or
(f) two R groups are independently monosaccharide subunits; and/or
(g) two R groups are independently hydrocarbyl groups; and/or
(h) one or two R groups are independently hydrogen, or an alkyl, acyl or alkoxycarbonyl group; and/or
(i) one or two R groups are independently hydrogen, or a $C_1$-$C_6$ alkyl, $C_2$-$C_6$ acyl, $C_2$-$C_6$ halo-acyl, or $C_{1-20}$ alkoxycarbonyl group; and/or
(j) one or two R groups are independently a methyl, ethyl, acetyl, trifluoroacetyl, Boc, Fmoc, or Zervas group.

In one embodiment of the present invention, none of the R groups are a —$SO_2$—OR' or —$SO_2$—N(R')$_2$ group. In another embodiment, none of the R groups are acyl. In another embodiment, none of the R groups contain an aromatic group.

In one embodiment of the present invention, each R group that is not hydrogen contains 1-12 carbon atoms. Each R group that is not hydrogen may contain 1-7, 1-6 or 1-4 carbon atoms. Each R group that is not hydrogen may contain at least 1, at least 2, at least 3, at least 4, at least 5, or at least 6 carbon atoms.

In one embodiment of the present invention, each R group contains 1-200 atoms. Each R group may contain 1-100, 1-50, 1-30, 1-20, 1-15, 1-10 or 1-5 atoms. Each R group may contain at least 2, at least 4, at least 6, at least 8, or at least 10 atoms.

Preferably the compounds of the present invention comprise:
(a) at least two or at least three sulphate groups; and/or
(b) at least one —O—$SO_2$—OR', —NR'—$SO_2$—OR', or —O—$SO_2$—N(R')$_2$ group; and/or
(c) at least one —$OSO_3$R' group; and/or
(d) at least two monosaccharide subunits, each of which is substituted with at least one sulphate group; and/or
(e) at least one pyranosyl subunit, which is substituted with one, two or three sulphate groups in the 2-, 3- and/or 6-position relative to the anomeric carbon of the pyranosyl subunit; preferably the pyranosyl subunit is part of a disaccharide; and/or
(f) at least one pyranosyl subunit, which is substituted with two or three sulphate groups in the 2-, 3- and/or 6-position relative to the anomeric carbon of the pyranosyl subunit; preferably the pyranosyl subunit is part of a disaccharide; and/or
(g) a first pyranosyl subunit, which is substituted with one sulphate group in the 2- or 6-position relative to the anomeric carbon of the pyranosyl subunit, and a second pyranosyl subunit, which is substituted with one sulphate group in the 2- or 3-position relative to the anomeric carbon of the pyranosyl subunit and one sulphate group in the 6-position relative to the anomeric carbon of the pyranosyl subunit; preferably the first and second pyranosyl subunits form a disaccharide; and/or
(h) at least one pyranosyl subunit, which is substituted with one or two sulphate groups in the 4- and/or 6-position relative to the anomeric carbon of the pyranosyl subunit; preferably the pyranosyl subunit is part of an oligosaccharide or a polysaccharide; and/or
(i) at least one, two or three sulphate groups, located on primary hydroxyl positions; and/or
(j) a sulphate group which is provided on a monosaccharide subunit comprising a glycosidic amine group.

In one embodiment of the present invention, some or all of the sulphate groups are directly linked to a monosaccharide subunit, such that the —O—$SO_2$—OR', —NR'—$SO_2$—OR', —O—$SO_2$—N(R')$_2$ or —NR'—$SO_2$—N(R')$_2$ group concerned is directly bonded to a carbon atom of the backbone of a monosaccharide subunit without any intervening atoms being present. Preferably 1, 2, 3, 4, 5, 6, 7, 8, or all sulphate groups are directly linked to a monosaccharide subunit.

In a preferred embodiment, 1-50, or 2-30, or 3-15, or 6-12, or all the hydroxyl groups on the monosaccharide subunits independently have been replaced with a sulphate group. The specified range relates to the total number of hydroxyl groups that have been replaced with a sulphate group across all the monosaccharide subunits within the compound.

In another preferred embodiment, 1-9, or 2-8, or 3-4 hydroxyl groups on each of 1, 2, 3, 4, 5, 6, 7, 8, or all monosaccharide subunits independently have been replaced with a sulphate group. Here, the specified range relates to the number of hydroxyl groups that have been replaced with a sulphate group per individual monosaccharide subunit within the compound, and the specified number relates to the number of monosaccharide subunits on which the specified replacement has occurred.

Where the compound of the present invention comprises a disaccharide or a disaccharide subunit (i.e. two monosaccharide subunits directly linked to each other), in one embodiment, one, two or three hydroxyl groups of the disaccharide or disaccharide subunit have been replaced with a sulphate group. In such an embodiment, the replacement ratio A:B, in relation to the number of hydroxyl groups replaced by sulphate groups on the first monosaccharide subunit (A) and on the second monosaccharide subunit (B) of the disaccharide or disaccharide subunit is preferably 2:1, 1:2, 2:0, 0:2, 1:1, 0:1 or 1:0.

In another preferred embodiment, the compound is a partially or fully sulphated saccharide.

In preferred embodiments of the present invention:
(a) R' is independently hydrogen, a metal, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises 1-15 carbon atoms; and/or
(b) R' is independently hydrogen, an alkali metal, an earth alkali metal, copper, silver, zinc, or a $C_1$-$C_6$ alkyl group.

When R' is a metal, then typically —$OSO_3$R' is –$OSO_3^-$Li$^+$, —$OSO_3^-$Na$^+$, —$OSO_3^-$K$^+$, —$OSO_3^-$Cu$^+$, or —$OSO_3^-$Ag$^+$, or two —$OSO_3$R' together are (—$OSO_3^-$)$_2$Mg$^{2+}$, (—$OSO_3^-$)$_2$Ca$^{2+}$, (—$OSO_3^-$)$_2$Cu$^{2+}$, or (—$OSO_3^-$)$_2$Zn$^{2+}$, or three —$OSO_3$R' together are (—$OSO_3^-$)$_3$Al$^{3+}$; typical —NR'—$SO_2$—OR' groups comprise the same metal cations.

Preferably the compounds of the present invention comprise:
(a) 1-100, 1-20, 2-10, or 2-4 monosaccharide subunits; and/or
(b) 1, 2, 3, 4, 5, 6, 7, 8, 9, 10 or more monosaccharide subunits; and/or
(c) a sequence of 1, 2, 3, 4, 5, 6, 7, 8, 9, 10 or more monosaccharide subunits.

It is preferred that, in total, including any further monosaccharide subunits, the compounds of the present invention contain one to twelve monosaccharide subunits, preferably one to eight monosaccharide subunits, preferably one to six monosaccharide subunits, preferably two to four monosaccharide subunits, preferably two to three monosaccharide subunits. Alternatively, the compounds may contain, in total, including any further monosaccharide subunits, one monosaccharide subunit, or two monosaccharide subunits, or three monosaccharide subunits, or four monosaccharide subunits, or five monosaccharide subunits, or six monosaccharide subunits, or seven monosaccharide subunits, or eight monosaccharide subunits, or nine monosaccharide subunits, or ten monosaccharide subunits, or eleven monosaccharide subunits, or twelve monosaccharide subunits.

All monosaccharide subunits are independently aldosyl or ketosyl monosaccharides. Preferably, 1, 2, 3, 4, or all monosaccharide subunits of the compounds of the present invention are independently triosyl, tetrosyl, pentosyl, hexosyl, heptosyl, octosyl or nonosyl monosaccharides. More preferably, 1, 2, 3, 4, or all monosaccharide subunits are independently glycerosyl, erythrosyl, threosyl, ribosyl, arabinosyl, xylosyl, lyxosyl, allosyl, altrosyl, glucosyl, mannosyl, gulosyl, idosyl, galactosyl, talosyl, rhamnosyl or fucosyl monosaccharides. All monosaccharide subunits are independently in the D- or L-configuration.

In a preferred embodiment, 1, 2, 3, 4, or all monosaccharide subunits are independently tetrosyl monosaccharides or higher, and the ring of those monosaccharides is furanosyl. In an alternative preferred embodiment, 1, 2, 3, 4, or all monosaccharide subunits are independently pentosyl monosaccharides or higher, and the ring of those monosaccharides is pyranosyl.

The stereochemistry of each glycosidic bond is independently α or β.

A preferred compound of the present invention is:

(a) a glucosylamine;
(b) β,β-di-glucosylamine;
(c) a mono-, di-, tri-, tetra-, penta-, hexa-, hepta- or octa-sulphated β,β-di-glucosylamine, or a mixture thereof;
(d) a mono-, di-, tri-, tetra-, penta-, hexa-, hepta- or octa-sulphated N-acetyl-β,β-di-glucosylamine, or a mixture thereof;
(e) a mono-, di-, tri-, tetra-, penta-, hexa-, hepta- or octa-sulphated N-ethyl-β,β-di-glucosylamine, or a mixture thereof;
(f) a sulphated di-(4,4'-glucosylglucosyl)amine;
(g) 1-benzamido-1-deoxy-2,3,4,6-tetra potassium sulphonatoglucose; or
(h) 1-N-octyl-1-N-decanoyl-1-amino-1-deoxy-6-potassium sulphonate-muramyl-D-isoglutamyl-alanine.

In one embodiment of the present invention, two R groups and the nitrogen atom to which they are attached, together do not form a heterocyclic aromatic group. In another embodiment, the atom connectivity S—O—P is not present in any monosaccharide subunit and/or in the entire compound. In yet another embodiment, the compound does not contain the group —O—P(=O)(OH)—O—SO$_2$OH. In another embodiment, the compound is not a nucleoside and/or not a nucleotide. In yet another embodiment, the compound does not comprise a ribose subunit comprising a glycosidic tertiary amine.

A third aspect of the present invention provides a compound having the formula (I):

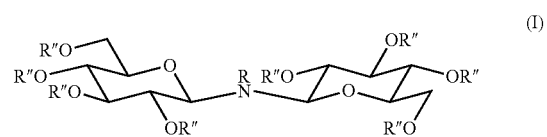

wherein:
R is Ac, Me, Et, COCF$_3$, or COPh;
each R" is SO$_3$R' or H with at least one R" being SO$_3$R'; and
each R' is H, Li, Na or K;
or a tautomer, a stereoisomer or a salt thereof.

The 8 R" groups may be 8×SO$_3$R', or 7×SO$_3$R' and 1×H, or 6×SO$_3$R' and 2×H, or 5×SO$_3$R' and 3×H, or 4×SO$_3$R' and 4×H, or 3×SO$_3$R' and 5×H, or 2×SO$_3$R' and 6×H, or 1×SO$_3$R' and 7×H.

The third aspect of the present invention further provides a compound having the formula (II):

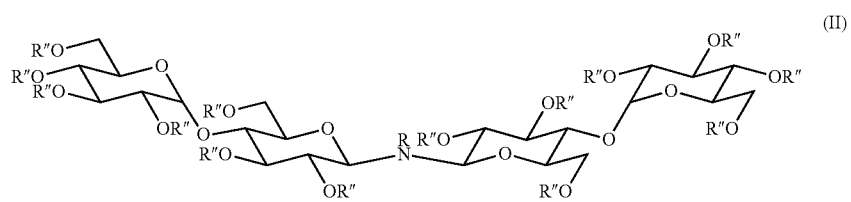

wherein:
R is Ac, Me, Et, COCF$_3$, or COPh;
each R" is SO$_3$R' or H with at least one R" being SO$_3$R'; and
each R' is H, Li, Na or K;
or a tautomer, a stereoisomer or a salt thereof.

The 14 R" groups may be 14×SO$_3$R', or 13×SO$_3$R' and 1×H, or 12×SO$_3$R' and 2×H, or 11×SO$_3$R' and 3×H, or 10×SO$_3$R' and 4×H, or 9×SO$_3$R' and 5×H, or 8×SO$_3$R' and 6×H, or 7×SO$_3$R' and 7×H, or 6×SO$_3$R' and 8×H, or 5×SO$_3$R' and 9×H, or 4×SO$_3$R' and 10×H, or 3×SO$_3$R' and 11×H, or 2×SO$_3$R' and 12×H, or 1×SO$_3$R' and 13×H.

The third aspect of the present invention further provides a compound having the formula (III):

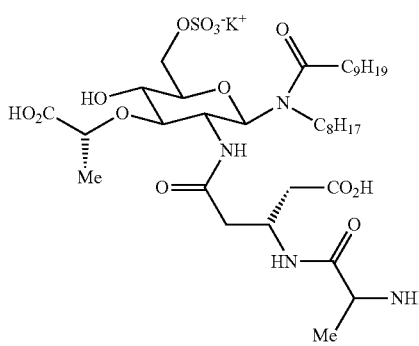
(III)

wherein R is H, CHO or COMe;
or a tautomer, a stereoisomer or a salt thereof.
The third aspect of the present invention further provides a compound having the formula (IV):

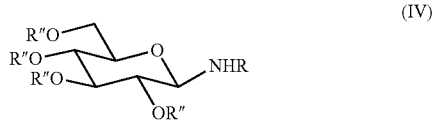
(IV)

wherein:
R is Ac, Me, Et, COCF$_3$, or COPh;
each R" is SO$_3$R' or H with at least one R" being SO$_3$R'; and
each R' is H, Li, Na or K;
or a tautomer, a stereoisomer or a salt thereof.
The 4 R" groups may be 4×SO$_3$R', or 3×SO$_3$R' and 1×H, or 2×SO$_3$R' and 2×H, or 1×SO$_3$R' and 3×H.

The third aspect of the present invention further provides stereoisomers of the compounds having formula (I), (II), (III) or (IV) as defined above.

The compounds of the first, second and third aspects of the present invention can be used both, in their free base form and their acid addition salt form. For the purposes of this invention, a 'salt' of a compound of the present invention can be an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic acid) or amino acids (for example, ornithinic, glutamic or aspartic acid). A preferred salt is a hydrohalogenic, sulphuric, phosphoric or organic acid addition salt. The acid addition salt may be a mono-, di-, tri-, tetra- or multi-acid addition salt, or a mixture thereof. A preferred salt is a multi-acid addition salt.

The compounds of the first, second and third aspects of the present invention can also be used both, in their free acid form and their salt form. For the purposes of this invention, a 'salt' of a compound of the present invention can also be formed between a carboxylic acid, sulphate, or other suitable functionality of a compound of the present invention and a suitable cation. Suitable cations include, but are not limited to, sodium, potassium, magnesium, calcium, ammonium and choline. The salt may be a mono-, di-, tri-, tetra- or multi-salt, or a mixture thereof. Preferably the salt is a multi-sodium, potassium, magnesium, calcium, ammonium or choline salt. More preferably the salt is a multi-potassium salt. Preferably the salt is a pharmaceutically acceptable salt. In one embodiment of the present invention, each sulphate group of a compound of the present invention exists in its salt form.

In addition to pharmaceutically acceptable salts, other salts are included in the present invention, since they have potential to serve as intermediates in the purification or preparation of other, for example pharmaceutically acceptable, salts, or are useful for identification, characterisation or purification of the compounds of the present invention.

The present invention encompasses salts, derivatives, solvates, clathrates and/or hydrates (including anhydrous forms) of the compounds of the present invention. Preferably these are pharmaceutically acceptable salts, derivatives, solvates, clathrates and/or hydrates (including anhydrous forms) of the compounds of the present invention.

The present invention encompasses quaternary ammonium salts of the compounds of the first, second and third aspects of the present invention, wherein the nitrogen of the glycosidic amine group is further substituted by a substituent other than hydrogen, resulting in a positive charge on the nitrogen, balanced by a suitable counter-anion. Preferably the substituent is alkyl, preferably methyl or ethyl. Suitable counter-anions include any of those formed in the process of generating acid addition salts as discussed above. Preferably, the compounds of the present invention do not exist as quaternary ammonium salts.

The compounds of the first, second and third aspects of the present invention may contain one or more chiral centres. The compounds may therefore exist in two or more stereoisomeric forms. The present invention encompasses racemic mixtures of the compounds of the present invention as well as enantiomerically enriched and substantially enantiomerically pure isomers of the compounds of the present invention. For the purposes of this invention, a 'substantially enantiomerically pure' isomer of a compound comprises less than 5% of other isomers of the same compound, preferably less then 3%, preferably less than 2%, preferably less than 1%, preferably less than 0.5%.

For the purposes of all aspects of the present invention, an 'alkyl' group is defined as a monovalent saturated hydrocarbon, which may be straight-chained or branched, or be or include cyclic groups. Examples of alkyl groups are methyl, ethyl, n-propyl, i-propyl, n-butyl, i-butyl, t-butyl and n-pentyl groups. Preferably an alkyl group is straight-chained or branched and does not include any heteroatoms in its carbon skeleton. Preferably an alkyl group is a C$_1$-C$_{12}$ alkyl group, which is defined as an alkyl group containing from 1 to 12 carbon atoms. More preferably an alkyl group is a C$_1$-C$_6$ alkyl group, which is defined as an alkyl group containing from 1 to 6 carbon atoms. An alkyl group may also be a C$_1$-C$_4$ alkyl group, which is defined as an alkyl group containing from 1 to 4 carbon atoms. An 'alkylene' group is similarly defined as a divalent alkyl group.

An 'alkenyl' group is defined as a monovalent hydrocarbon, which comprises at least one carbon-carbon double bond, which may be straight-chained or branched, or be or include cyclic groups. Examples of alkenyl groups are vinyl, allyl, but-1-enyl and but-2-enyl groups. Preferably an alkenyl group is straight-chained or branched and does not include any heteroatoms in its carbon skeleton. Preferably an alkenyl group is a $C_2$-$C_{12}$ alkenyl group, which is defined as an alkenyl group containing from 2 to 12 carbon atoms. More preferably an alkenyl group is a $C_2$-$C_6$ alkenyl group, which is defined as an alkenyl group containing from 2 to 6 carbon atoms. An alkenyl group may also be a $C_2$-$C_4$ alkenyl group, which is defined as an alkenyl group containing from 2 to 4 carbon atoms. An 'alkenylene' group is similarly defined as a divalent alkenyl group.

An 'alkynyl' group is defined as a monovalent hydrocarbon, which comprises at least one carbon-carbon triple bond, which may be straight-chained or branched, or be or include cyclic groups. Examples of alkynyl groups are ethynyl, propargyl, but-1-ynyl and but-2-ynyl groups. Preferably an alkynyl group is straight-chained or branched and does not include any heteroatoms in its carbon skeleton. Preferably an alkynyl group is a $C_2$-$C_{12}$ alkynyl group, which is defined as an alkynyl group containing from 2 to 12 carbon atoms. More preferably an alkynyl group is a $C_2$-$C_6$ alkynyl group, which is defined as an alkynyl group containing from 2 to 6 carbon atoms. An alkynyl group may also be a $C_2$-$C_4$ alkynyl group, which is defined as an alkynyl group containing from 2 to 4 carbon atoms. An 'alkynylene' group is similarly defined as a divalent alkynyl group.

An 'acyl' group is defined as a —$COR^x$ group, wherein $R^x$ is hydrogen, or an optionally substituted alkyl, alkenyl, alkynyl, aryl, arylalkyl, arylalkenyl, arylalkynyl, alkylaryl, alkenylaryl or alkynylaryl group. Examples of acyl groups are formyl, acetyl, trifluoroacetyl, propanoyl and benzoyl groups. Preferably an acyl group is straight-chained or branched and does not include any heteroatoms in its carbon skeleton. Preferably an acyl group is a $C_1$-$C_{12}$ acyl group, which is defined as an acyl group containing from 1 to 12 carbon atoms. More preferably an acyl group is a $C_1$-$C_6$ acyl group, which is defined as an acyl group containing from 1 to 6 carbon atoms. An acyl group may also be a $C_1$-$C_4$ acyl group, which is defined as an acyl group containing from 1 to 4 carbon atoms. An acyl group may also contain 1, 2, 3, 4, 5 or 6 carbon atoms.

An 'aryl' group is defined as a monovalent aromatic hydrocarbon. Examples of aryl groups are phenyl, naphthyl, anthracenyl and phenanthrenyl groups. Preferably an aryl group does not include any heteroatoms in its carbon skeleton. Preferably an aryl group is a $C_4$-$C_{14}$ aryl group, which is defined as an aryl group containing from 4 to 14 carbon atoms. More preferably an aryl group is a $C_6$-$C_{10}$ aryl group, which is defined as an aryl group containing from 6 to 10 carbon atoms. An 'arylene' group is similarly defined as a divalent aryl group.

For the purposes of the present invention, where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

For the purposes of this invention, a substituted group may be substituted monovalently with one or more of —F, —Cl, —Br, —I, —$CF_3$, —$CCl_3$, —$CBr_3$, —$CI_3$, —OH, —SH, —$NH_2$, —$N_3$, —NH=$NH_2$, —CN, —$NO_2$, —COOH, —$R^\beta$—O—$R^\gamma$, —$R^\beta$—S—$R^\gamma$, —$R^\beta$—SO—$R^\gamma$, —$R^\beta$—$SO_2$—$R^\gamma$, —$R^\beta$—$SO_2$—$OR^\gamma$, —$R^\beta O$—$SO_2$—$R^\gamma$, —$R^\beta$—$SO_2$—$N(R^\gamma)_2$, —$R^\beta$—$NR^\gamma$—$SO_2$—$R^\gamma$, —$R^\beta O$—$SO_2$—$OR^\gamma$, —$R^\beta O$—$SO_2$—$N(R^\gamma)_2$, —$R^\beta$—$NR^\gamma$—$SO_2$—$OR^\gamma$, —$R^\beta$—$NR^\gamma$—$SO_2$—$N(R^\gamma)_2$, —$R^\beta$—$N(R^\gamma)_2$, —$R^\beta$—$N(R^\gamma)_3^+$, —$R^\beta$—$B(R^\gamma)_2$, —$R^\beta$—$P(R^\gamma)_2$, —$R^\beta$—$PO(R^\gamma)_2$, —$R^\beta$—$Si(R^\gamma)_3$, —$R^\beta$—CO—$R^\gamma$, —$R^\beta$—CO—$OR^\gamma$, —$R^\beta O$—CO—$R^\gamma$, —$R^\beta$—CO—$N(R^\gamma)_2$, —$R^\beta$—$NR^\gamma$—CO—$R^\gamma$, —$R^\beta O$—CO—$OR^\gamma$, —$R^\beta O$—CO—$N(R^\gamma)_2$, —$R^\beta$—$NR^\gamma$—CO—$OR^\gamma$, —$R^\beta$—$NR^\gamma$—CO—$N(R^\gamma)_2$, —$R^\beta$—CS—$R^\gamma$, —$R^\beta$—CS—$OR^\gamma$, —$R^\beta O$—CS—$R^\gamma$, —$R^\beta$—CS—$N(R^\gamma)_2$, —$R^\beta$—$NR^\gamma$—CS—$R^\gamma$, —$R^\beta O$—CS—$OR^\gamma$, —$R^\beta O$—CS—$N(R^\gamma)_2$, —$R^\beta$—$NR^\gamma$—CS—$OR^\gamma$, —$R^\beta$—$NR^\gamma$—CS—$N(R^\gamma)_2$, or —$R^\gamma$; preferably monovalently with one or more of —F, —Cl, —Br, —I, —$CF_3$, —$CCl_3$, —$CBr_3$, —$CI_3$, —OH, —SH, —$NH_2$, —$N_3$, —NH=$NH_2$, —CN, —$NO_2$, —COOH, —$R^\beta$—O—$R^\gamma$, —$R^\beta$—S—$R^\gamma$, —SO—$R^\gamma$, —$SO_2$—$R^\gamma$, —$SO_2$—$OR^\gamma$, —O—$SO_2$—$R^\gamma$, —O—$SO_2$—$OR^\gamma$, —$R^\beta$—$N(R^\gamma)_2$, —$R^\beta$—$N(R^\gamma)_3^+$, —$R^\beta$—$Si(R^\gamma)_3$, —$R^\beta$—CO—$R^\gamma$, —$R^\beta$—CO—$OR^\gamma$, —$R^\beta O$—CO—$R^\gamma$, —$R^\beta$—CO—$N(R^\gamma)_2$, —$R^\beta$—$NR^\gamma$—CO—$R^\gamma$, —$R^\beta O$—CO—$OR^\gamma$, —$R^\beta$—CS—$R^\gamma$, or —$R^\gamma$; or divalently with one or more of —$R^\beta$—, =O, =S, or =$NR^\gamma$; or trivalently with one or more of =N—$R^\beta$—. In this context, —$R^\beta$— is independently a chemical bond, or a substituted or unsubstituted alkylene, alkenylene or alkynylene group, optionally including one or more heteroatoms in its carbon skeleton. —$R^\gamma$ is independently hydrogen, or a substituted or unsubstituted alkyl or aryl group, optionally including one or more heteroatoms in its carbon skeleton. Optional substituent(s) are not taken into account when calculating the total number of carbon atoms in the parent group substituted with the optional substituent(s). Preferably the total number of carbon atoms in any given —$R^\gamma$ or —$R^\beta$— group, including any further substitution on that group, is 1-50, preferably 1-20, preferably 1-10, preferably 1-6. Preferably a substituted group comprises 1, 2 or 3 substituents, preferably 1 or 2 substituents, preferably 1 substituent.

Any optional substituent may be protected. Suitable protecting groups for protecting optional substituents are known in the art, for example from 'Protective Groups in Organic Synthesis' by Theodora W. Greene and Peter G. M. Wuts (Wiley-Interscience, 3$^{rd}$ edition, 1999).

For the purposes of this invention, a heteroatom is preferably a B, Si, N, P, O or S; more preferably a heteroatom is a N, O or S.

A fourth aspect of the present invention provides a polysaccharide, oligosaccharide, peptide or protein derivative comprising a polysaccharide, oligosaccharide, peptide or protein covalently linked to a compound of the first, second or third aspect of the present invention.

As used herein, the term 'peptide' refers to a group comprising 1 to 50 amide bonds. As used herein, the term 'protein' refers to a group comprising 51 or more amide bonds. A peptidyl or proteinyl group may comprise any type of amino acid subunit. The amino acid subunits may be naturally occurring or synthetic. Preferably, all amino acid subunits are naturally occurring. The amino acid subunits may be α-, β-, γ- or δ-amino acid subunits, or a mixture thereof. Preferably, all amino acid subunits are α-amino acid subunits.

Any polysaccharide, oligosaccharide, peptide or protein derivative of the present invention may be further protected and/or sulphated. Suitable protecting groups for protecting polysaccharide, oligosaccharide, peptide and protein derivatives are known in the art, for example from 'Protective Groups in Organic Synthesis' by Theodora W. Greene and Peter G. M. Wuts (Wiley-Interscience, 3$^{rd}$ edition, 1999).

Preferably, in any of the above aspects of the present invention, the total number of amino acid residues within the compound or polysaccharide, oligosaccharide, peptide or protein derivative is in the range of from 1 to 1,000, preferably 1 to 100, preferably 1 to 10, preferably 2 to 8.

Preferably, in any of the above aspects of the present invention, the molecular weight of the compound or polysaccharide, oligosaccharide, peptide or protein derivative is in the range of from 100 to 100,000 Da, preferably 100 to 50,000 Da, preferably 200 to 10,000 Da, preferably 300 to 5,000 Da, preferably 500 to 3,500 Da.

Preferably, in any of the above aspects of the present invention, the total number of carbon atoms in the compound or polysaccharide, oligosaccharide, peptide or protein derivative is in the range of from 4 to 10,000, preferably 4 to 1,000, preferably 6 to 500, preferably 6 to 100, preferably 6 to 50.

Preferably, in any of the above aspects of the present invention, the total number of atoms in the compound or polysaccharide, oligosaccharide, peptide or protein derivative is in the range of from 4 to 50,000, preferably 4 to 10,000, preferably 6 to 5,000, preferably 6 to 1,000, preferably 6 to 250, preferably 10 to 100.

Preferably, in any of the above aspects of the present invention, the total number of monosaccharide subunits in the compound or polysaccharide, oligosaccharide, peptide or protein derivative is in the range of from 1 to 1000, preferably 1 to 100, preferably 1 to 10, preferably 2 to 8.

Preferably, in any of the above aspects of the present invention, the total number of glycosidic bonds in the compound or polysaccharide, oligosaccharide, peptide or protein derivative is in the range of from 1 to 1,000, preferably 1 to 100, preferably 1 to 10, preferably 2 to 8.

A fifth aspect of the present invention provides a mixture of any of the compounds or polysaccharide, oligosaccharide, peptide or protein derivatives of the present invention, wherein the compounds or derivatives differ only in their stereochemistry at the anomeric centre and/or in their degree of sulphation and/or their position of sulphation. Preferably 50%, 75%, 80%, 85%, 90%, 95% or 99% of the compounds or derivatives lie within three consecutive degrees of sulphation. Preferably the three consecutive degrees of sulphation are three- to five-fold sulphation, four- to six-fold sulphation, or five- to seven-fold sulphation.

For the purposes of the present invention, a 'sulphate group' is a —O—SO$_2$—OR', —NR'—SO$_2$—OR', —O—SO$_2$—N(R')$_2$ or —NR'—SO$_2$—N(R')$_2$ group, wherein each R' is independently hydrogen, a metal, a monosaccharide subunit, or a hydrocarbyl group. Preferably a sulphate group is a —OSO$_3$R' group. Preferably R' is hydrogen. The terms 'sulphated' and 'sulphation' are defined accordingly.

For the purposes of the present invention, the term 'x- to y-fold sulphation' means a mixture of sulphated compounds, 80%, 85%, 90% or more of which have from x to y sulphate groups. Thus, for example, a 'three- to five-fold sulphated compound' is a mixture of compounds, 80%, 85%, 90% or more of which have from three to five sulphate groups. A compound of the present invention, which is of a specific degree of sulphation, i.e. a compound comprising x sulphate groups, may be a mixture of regioisomers, in which the positions of the sulphate groups on the compound vary.

The compounds of the present invention can be prepared as mixtures of x- to y-fold sulphated compounds. Examples of such methods of preparation are set out in the synthetic examples below.

Alternatively, if sulphation at specific positions of the compounds is desired, then substituents, in particular hydroxyl groups, on the monosaccharide subunit(s) may need protecting prior to directed sulphation. Suitable protecting groups are known in the art, for example, from 'Protective Groups in Organic Synthesis' by Theodora W. Greene and Peter G. M. Wuts (Wiley-Interscience, 3$^{rd}$ edition, 1999). Methods of protecting and sulphating saccharides are also known, for example, from 'Monosaccharides, Their Chemistry and Their Roles in Natural Products' by Peter Collins and R. Ferrier (John Wiley & Sons, 1998), 'Carbohydrate Chemistry' by Benjamin G. Davis and Antony J. Fairbanks (Oxford Chemistry Primers, Oxford University Press, 2002), and 'Preparative Carbohydrate Chemistry' by Stephen Hanessian (ed.) (Marcel Dekker Ltd, 1997).

Preferred compounds of the present invention comprise at least one pyranosyl subunit, which is substituted with one, two or three sulphate groups in the 2-, 3- and/or 6-position relative to the anomeric carbon of the pyranosyl subunit. Other preferred compounds of the present invention comprise a first pyranosyl subunit, which is substituted with one sulphate group in the 2- or 6-position relative to the anomeric carbon of the pyranosyl subunit, and a second pyranosyl subunit, which is substituted with one sulphate group in the 2- or 3-position relative to the anomeric carbon of the pyranosyl subunit and one sulphate group in the 6-position relative to the anomeric carbon of the pyranosyl subunit. Other preferred compounds of the present invention comprise at least one pyranosyl subunit, which is substituted with one or two sulphate groups in the 4- and/or 6-position relative to the anomeric carbon of the pyranosyl subunit. Formula H below has been marked with substituents X in the 2-, 3-, 4- and 6-positions relative to the anomeric carbon of the pyranosyl subunit:

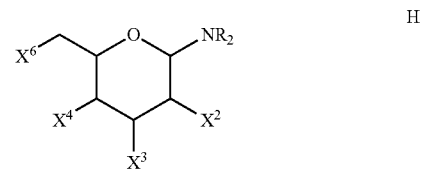

H

A sixth aspect of the present invention provides a method of synthesising a compound of the first aspect of the present invention, comprising the sulphation of a compound comprising:

at least one monosaccharide subunit comprising a glycosidic —NR$_2$ group, a glycosidic —NR$_3^+$ group, a directly bonded =NR group, or a directly bonded =NR$_2^+$ group, wherein each R is independently hydrogen, a —SO$_2$—OR' or —SO$_2$—N(R')$_2$ group, a further monosaccharide subunit, or a hydrocarbyl group, or two or three R groups and the nitrogen atom to which they are attached, together form a further monosaccharide subunit or a cyclic hydrocarbyl group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the compound is not 3'-phosphoadenosine-5'-phosphosulphate.

Preferably the method comprises the sulphation of a compound comprising at least one monosaccharide subunit comprising a glycosidic —NR$_2$ group or a glycosidic —NR$_3^+$ group, or a tautomer or thereof.

The sixth aspect of the present invention further provides a method of synthesising a compound of the second aspect of the present invention, comprising the sulphation of a compound comprising:

a sequence of at least two monosaccharide subunits linked by a glycosidic —NR— group, a glycosidic —NR$_2^+$— group, a directly bonded =N— group, or a directly bonded =NR$^+$— group, wherein each R is independently hydrogen, a —SO$_2$—OR' or —SO$_2$—N(R')$_2$ group, a further monosaccharide subunit, or a hydrocarbyl group, or two R groups and the nitrogen atom to which they are attached, together form a further monosaccharide subunit or a cyclic hydrocarbyl group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof.

Preferably the method comprises the sulphation of a compound comprising:

a sequence of at least two monosaccharide subunits linked by a glycosidic —NR— group or a glycosidic —NR$_2^+$— group, wherein each R is independently hydrogen, a further monosaccharide subunit, or a hydrocarbyl group, or two R groups and the nitrogen atom to which they are attached, together form a further monosaccharide subunit or a cyclic hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a tautomer or a salt thereof.

In any of the synthetic methods of the present invention, the compound may be O- and/or N-protected prior to sulphation. Preferably, for O-protection, O-silyl, O-acetyl, O-acyl, O-acetal, O-ketal, O-benzyl, O-benzoyl or O-THP protection is used. Preferably, for N-protection, N-Boc, N-Fmoc, N-Zervas, N-acetyl, N-acyl, N-alkyl or N-trifluoroacetyl protection is used.

In one embodiment of the sixth aspect of the present invention, the sulphation is performed using sulphur trioxide complexed to a nitrogen-containing base. Preferably the nitrogen-containing base is pyridine. Preferably the pyridine is used as solvent.

In another embodiment of the sixth aspect of the present invention, the sulphation is performed using a halosulphonic acid or a silyl-protected halosulphonic acid. Preferably the halosulphonic acid or silyl-protected halosulphonic acid is chlorosulphonic acid or trimethylsilylchlorosulphonate respectively.

A seventh aspect of the present invention provides a product produced by any of the above methods.

An eight aspect of the present invention provides a pharmaceutical composition comprising a compound, a polysaccharide, oligosaccharide, peptide or protein derivative, a mixture, or a product of the invention, and a pharmaceutically acceptable excipient, carrier or diluent.

A compound, a polysaccharide, oligosaccharide, peptide or protein derivative, a mixture, a product, or a pharmaceutical composition of the present invention may be used in medicine.

A ninth aspect of the present invention provides a compound, a polysaccharide, oligosaccharide, peptide or protein derivative, a mixture, a product, or a pharmaceutical composition of the present invention for binding to a macromolecule. Preferably the macromolecule is a protein, peptide, nucleic acid, lipid, polysaccharide, oligosaccharide, glycosaminoglycan, or proteoglycan; more preferably the macromolecule is a protein. The binding may result in the inhibition, activation, modification, destruction, re-folding, denaturisation, aggregation, or oligomerisation of the macromolecule; more preferably the binding results in the inhibition of the macromolecule. Alternatively, a compound, a polysaccharide, oligosaccharide, peptide or protein derivative, a mixture, or a product of the present invention, can be used in the manufacture of a medicament for the inhibition, activation, modification, destruction, re-folding, denaturisation, aggregation, or oligomerisation of a macromolecule. Also encompassed is a method of inhibiting, activating, modifying, destroying, re-folding, denaturising, aggregating, or oligomerising a macromolecule, comprising administering an effective amount of a compound, a polysaccharide, oligosaccharide, peptide or protein derivative, a mixture, a product, or a pharmaceutical composition of the present invention, to a patient in need thereof.

In any use or method of the ninth aspect of the present invention, preferably the macromolecule is a protein, peptide, nucleic acid, lipid, polysaccharide, oligosaccharide, glycosaminoglycan, or proteoglycan; more preferably the macromolecule is a protein. Preferably the binding results in the inhibition, activation, modification, destruction, re-folding, denaturisation, aggregation, or oligomerisation of the macromolecule; more preferably the binding results in the inhibition of the macromolecule.

In any compound, any polysaccharide, oligosaccharide, peptide or protein derivative, any mixture, any product, any pharmaceutical composition, any use or any method of the ninth aspect of the invention, the binding can occur in vitro, ex vivo or in vivo.

In embodiments of the ninth aspect of the present invention, the macromolecule may be:

(a) a member of the lectin family of proteins;

(b) a transmembrane glycoprotein;

(c) a member of the selectin sub-class of proteins, such as an E-, L- or P-selectin;

(d) a member of the siglecs sub-class of proteins;

(e) a mannose binding protein or a mannose receptor;

(f) a glycosidase, such as a glucosidase, such as a β-glucosidase;

(g) a growth factor, such as a granulocyte colony stimulating factor (G-CSF), a granulocyte macrophage colony stimulating factor (GM-CSF), a nerve growth factor (NGF), a neurotrophin, a platelet-derived growth factor (PDGF), erythropoietin (EPO), thrombopoietin (TPO), myostatin (GDF-8), growth differentiation factor-9 (GDF9), a hepatocyte growth factor, or a fibroblast growth factor (FGF);

(h) follistatin;

(i) a phosphorylase, such as a glycogen phosphorylase, a starch phosphorylase, a maltodextrin phosphorylase, a hepatic phosphorylase, phosphorylase a or phosphorylase b; or (j) a cytokine receptor, such as a chemokine receptor, or a cytokine, such as a chemokine, such as monocyte chemoattractant proteins MCP-1 or MCP-3.

A tenth aspect of the present invention provides a method of modifying the level of a cytokine in vivo, ex vivo or in vitro, said method comprising contacting a compound, a polysaccharide, oligosaccharide, peptide or protein derivative, a mixture, a product, or a pharmaceutical composition of the present invention with a cell.

An eleventh aspect of the present invention provides a method of testing for a modification in the level of a cytokine in vivo, ex vivo or in vitro, said method comprising contacting a compound, a polysaccharide, oligosaccharide, peptide or protein derivative, a mixture, a product, or a pharmaceutical composition of the present invention with a cell.

Preferably, in either the tenth or the eleventh aspect of the present invention, the cytokine is selected from GM-CSF, IL-1α, IL-1β, IL-2, IL-4, IL-5, IL-6, IL-7, IL-8, IL-10, IL-12, IL-13, IL-17, GCSF, VEGF, TNFα, RANTES, MCP-1 or IFNγ. Preferably the modification is an increase or decrease in the level of the cytokine. Preferably the modification is to the level of the cytokine synthesised by the cell.

As used herein, the term 'level of a cytokine' refers to the amount or concentration of the cytokine.

As used herein, 'a method of testing for a modification in the level of a cytokine' includes testing for an increase, a decrease, or no change in the level of that cytokine. Preferably, the test is for an increase or a decrease in the level of that cytokine.

In preferred embodiments of the eleventh aspect of the present invention, the method of testing relates to a method of observing an increase or a decrease in the level of the cytokine to be tested.

Preferably, in any embodiment of the eleventh aspect of the present invention, the cytokine level is tested using a radioimmunoassay, fluorescence activated cell sorting (FACS), a Northern blot analysis for mRNA, a gene chip assay, a gene activation assay, or an Enzyme-Linked ImmunoSorbent Assay (ELISA or EIA) such as an indirect ELISA, a sandwich ELISA, a competitive ELISA or an Enzyme-Linked Immunosorbent Spot assay (ELISpot). Preferably an ELISA is used. Preferably a bead-based sandwich ELISA is used, allowing for the levels of multiple cytokines to be measured simultaneously.

In one embodiment of either the tenth or the eleventh aspect of the present invention, the modification is a decrease in the level of GM-CSF, IL-1α, IL-1β, IL-2, IL-4, IL-5, IL-6, IL-10, IL-13, IL-17, GCSF, TNFα or IFNγ.

In another embodiment of either the tenth or the eleventh aspect of the present invention, the modification is an increase in the level of IL-7 or VEGF.

In yet another embodiment of either the tenth or the eleventh aspect of the present invention, the modification is no change or an increase in the level of IL-10.

In any embodiment of the tenth or the eleventh aspect of the present invention, it is preferred that the method comprises contacting the compound, polysaccharide, oligosaccharide, peptide or protein derivative, mixture, product, or pharmaceutical composition of the present invention with a blood cell and/or a human cell. Where the cell is a blood cell, it is preferred that the blood cell is an erythrocyte or a leukocyte such as a neutrophil, basophil, eosinophil, lymphocyte, monocyte, or macrophage.

In any embodiment of the tenth or the eleventh aspect of the present invention, it is preferred that the compound, polysaccharide, oligosaccharide, peptide or protein derivative, mixture, product, or pharmaceutical composition of the present invention is in fluid communication with the cell for at least 12 hours, preferably for at least 1, 2, 3, 4, 5 or 10 days.

Preferably, the compound, polysaccharide, oligosaccharide, peptide or protein derivative, mixture, product, or pharmaceutical composition of the present invention is in fluid communication with the cell at a concentration of between 0.001 and 1000 µM, preferably between 0.005 and 200 µM, preferably between 0.0075 and 50 µM, preferably about 0.01 µM.

In any embodiment of the tenth or the eleventh aspect of the present invention, it is preferred that the method is performed in vivo, preferably in such a manner that the contacting occurs after gastrointestinal absorption of the compound, polysaccharide, oligosaccharide, peptide or protein derivative, mixture, product, or pharmaceutical composition of the present invention, and/or preferably such that the modification, increase or decrease of the cytokine level is non-gastrointestinal.

Alternatively, in any embodiment of the tenth or the eleventh aspect of the present invention, the method may be performed in vitro, preferably for a non-therapeutic purpose.

In any embodiment of the eleventh aspect of the present invention, it is preferred that the cytokine level is tested at intervals of between 30 minutes and 10 days, preferably at intervals of between 2 hours and 5 days, preferably at intervals of between 12 hours and 2 days, preferably the cytokine level is tested about once a day.

In any embodiment of the tenth or the eleventh aspect of the present invention, it is preferred that the modification in the cytokine level occurs and/or is observed over a period of at least 12 hours, preferably over at least 1, 2, 3, 4, 5 or 10 days.

It is generally preferred that the same type of modification of the cytokine level occurs over the entire period of modification and/or observation, i.e. that the cytokine level is increased or decreased over the entire period. Alternatively, however, the type of modification may change over the period of modification and/or observation. For instance, a period of increased cytokine level may be observed followed by a period of decreased cytokine level, and vice versa. Alternatively still, periods of increased and/or decreased cytokine level may be accompanied by periods with no change in the cytokine level.

It is preferred that any increase and/or decrease in a cytokine level is statistically significant. Preferably any increase and/or decrease has a p-value of less than 0.2, less than 0.1, less than 0.05, less than 0.01, less than 0.001, or less than 0.0001.

In a further preferred embodiment, any increase and/or decrease in a cytokine level is greater than 10%, greater than 25%, greater than 50%, or greater than 75%.

In any embodiment of the tenth aspect of the present invention, the method may be a method of treating or preventing a disease or condition. Preferably the disease or condition is a disease or condition dependent upon the level of a cytokine. Preferably the disease or condition is inflammation, an inflammatory disorder, a proliferative disorder, an immune disorder, an autoimmune disorder, an angiogenesis-dependent disorder, a sensitivity disorder, an adverse endocrine reaction or a degenerative disorder. The disease or condition may be gastrointestinal or non-gastrointestinal. The disease or condition may include any of those listed below.

In one embodiment of the eleventh aspect of the present invention, the method may be a method of testing the compound in order to determine its efficacy at treating or preventing a disease or condition and/or its propensity for inducing unwanted side-effects. In another embodiment of the eleventh aspect of the present invention, the method may be a method of testing for a disease or condition. Preferably the disease, condition or side-effect is a disease, condition or side-effect dependent upon the level of the cytokine to be tested. Preferably the disease or condition is inflammation, an inflammatory disorder, a proliferative disorder, an immune disorder, an autoimmune disorder, an angiogenesis-dependent disorder, a sensitivity disorder, an adverse endocrine reaction or a degenerative disorder. The disease or condition may be gastrointestinal or non-gastrointestinal. The disease or condition may include any of those listed below.

A twelfth aspect of the present invention provides a compound, a polysaccharide, oligosaccharide, peptide or protein derivative, a mixture, a product, or a pharmaceutical composition of the present invention, for the treatment or prevention of inflammation. Alternatively, a compound, a polysaccharide, oligosaccharide, peptide or protein derivative, a mixture, or a product of the present invention can be used in the manufacture of a medicament for the treatment or prevention of inflammation. Also encompassed is a method of treating or preventing inflammation, comprising administering a therapeutically or prophylactically effective amount of a compound, a polysaccharide, oligosaccharide, peptide or protein derivative, a mixture, a product, or a pharmaceutical composition of the present invention, to a patient in need thereof. Also encompassed is a method of modifying the level of a cytokine in vivo, ex vivo or in vitro, said method comprising contacting a compound, a polysaccharide, oligosaccharide, peptide or protein derivative, a mixture, a product, or a pharmaceutical composition of the present invention, with a cell, wherein the method is a method of treating or preventing inflammation.

In a preferred embodiment of the twelfth aspect of the present invention, the inflammation is chronic inflammation. Preferably, the inflammation occurs as a result of an inflammatory disorder, as a symptom of a non-inflammatory disorder, or is secondary to trauma, injury or autoimmunity.

A thirteenth aspect of the present invention provides a compound, a polysaccharide, oligosaccharide, peptide or protein derivative, a mixture, a product, or a pharmaceutical composition of the present invention, for the treatment or prevention of an inflammatory disorder, a proliferative disorder, an immune disorder, an angiogenesis-dependent disorder, a sensitivity disorder, an adverse endocrine reaction or a degenerative disorder. Alternatively, a compound, a polysaccharide, oligosaccharide, peptide or protein derivative, a mixture, or a product of the present invention can be used in the manufacture of a medicament for the treatment or prevention of an inflammatory disorder, a proliferative disorder, an immune disorder, an angiogenesis-dependent disorder, a sensitivity disorder, an adverse endocrine reaction or a degenerative disorder. Also encompassed is a method of treating or preventing an inflammatory disorder, a proliferative disorder, an immune disorder, an angiogenesis-dependent disorder, a sensitivity disorder, an adverse endocrine reaction or a degenerative disorder, comprising administering a therapeutically or prophylactically effective amount of a compound, a polysaccharide, oligosaccharide, peptide or protein derivative, a mixture, a product, or a pharmaceutical composition of the present invention, to a patient in need thereof. Also encompassed is a method of modifying the level of a cytokine in vivo, ex vivo or in vitro, said method comprising contacting a compound, a polysaccharide, oligosaccharide, peptide or protein derivative, a mixture, a product, or a pharmaceutical composition of the present invention, with a cell, wherein the method is a method of treating or preventing an inflammatory disorder, a proliferative disorder, an immune disorder, an angiogenesis-dependent disorder, a sensitivity disorder, an adverse endocrine reaction or a degenerative disorder.

In one embodiment of the twelfth or thirteenth aspect of the present invention, the inflammation, inflammatory disorder, proliferative disorder, immune disorder, angiogenesis-dependent disorder, sensitivity disorder, adverse endocrine reaction or degenerative disorder is an inflammatory bowel disease, Crohn's disease, ulcerative colitis, collagenous colitis, lymphocytic colitis, ischaemic colitis, diversion colitis, infective colitis or indeterminate colitis. In yet another embodiment, the inflammation, inflammatory disorder, proliferative disorder, immune disorder, angiogenesis-dependent disorder, sensitivity disorder, adverse endocrine reaction or degenerative disorder is psoriasis, plaque psoriasis, pustular psoriasis, guttate psoriasis, psoriatic arthritis, inverse psoriasis or erythrodermic psoriasis. In another embodiment, the inflammation, inflammatory disorder, proliferative disorder, immune disorder, angiogenesis-dependent disorder, sensitivity disorder, adverse endocrine reaction or degenerative disorder is sarcoidosis, arthritis, rheumatoid arthritis, osteoarthritis, Behçet's syndrome, asthma, chronic obstructive pulmonary disease, or atherosclerosis.

In another embodiment of the twelfth or thirteenth aspect of the present invention, the inflammation, inflammatory disorder, proliferative disorder, immune disorder, angiogenesis-dependent disorder, sensitivity disorder, adverse endocrine reaction or degenerative disorder is cancer, restenosis, papilloma, polyposis, fibrosis, proliferative bronchiolitis, tumour growth, proliferative periostitis, proliferative pulpitis, proliferative verrucous leukoplakia, or macular degeneration. Alternatively the inflammation, inflammatory disorder, proliferative disorder, immune disorder, angiogenesis-dependent disorder, sensitivity disorder, adverse endocrine reaction or degenerative disorder is an autoimmune disorder, an immunodeficiency disorder, or a transplant rejection disorder including a disorder related to a transplant such as a disorder related to a renal, hepatic, corneal, cartilage, stem cell, chondrocyte, pulmonary, cardiac, vascular or myeloid transplant. Preferably, the autoimmune disorder, immunodeficiency disorder, or transplant rejection disorder is HIV infection, AIDS, multiple sclerosis, systemic lupus erythematosus or septic shock. The inflammation, inflammatory disorder, proliferative disorder, immune disorder, angiogenesis-dependent disorder, sensitivity disorder, adverse endocrine reaction or degenerative disorder may also be an allergy, a hyposensitivity or a hypersensitivity, preferably hypersensitivity following the reactivation of herpes.

In yet another embodiment of the twelfth or thirteenth aspect of the present invention, the inflammation, inflammatory disorder, proliferative disorder, immune disorder, angiogenesis-dependent disorder, sensitivity disorder, adverse endocrine reaction or degenerative disorder is diabetes. Preferably, the diabetes is diabetes mellitus, preferably type 1, type 2, gestational, malnutrition related, or impaired glucose tolerance related. Alternatively, the diabetes is diabetes insipidus, preferably central, nephrogenic, dipsogenic, or gestational.

In yet another embodiment of the twelfth or thirteenth aspect of the present invention, the inflammation, inflammatory disorder, proliferative disorder, immune disorder, angiogenesis-dependent disorder, sensitivity disorder, adverse endocrine reaction or degenerative disorder is a degenerative disease or disorder, a degenerative joint disease, a neurodegenerative disease, an inflammatory degenerative disease, or an osteochondral defect. The inflammation, inflammatory disorder, proliferative disorder, immune disorder, angiogenesis-dependent disorder, sensitivity disorder, adverse endocrine reaction or degenerative disorder may also be keratitis (including herpetic keratitis), herpes simplex or shingles.

In one embodiment of the twelfth or thirteenth aspect of the present invention, the inflammation, inflammatory disorder, proliferative disorder, immune disorder, angiogenesis-dependent disorder, sensitivity disorder, adverse endocrine reaction or degenerative disorder is not, or does not occur as a result of a gastrointestinal cancer or tumour, gastrointestinal polyposis, Crohn's disease, ulcerative colitis, collagenous colitis, lymphocytic colitis, ischaemic colitis, diversion colitis, infective colitis or indeterminate colitis.

In another embodiment of the thirteenth aspect of the present invention, the inflammatory disorder, proliferative disorder, immune disorder, angiogenesis-dependent disorder, sensitivity disorder, adverse endocrine reaction or degenerative disorder is an autoimmune disease.

Preferably, the autoimmune disease is selected from acute disseminated encephalitis, Addison's disease, ankylosing spondylitis, antiphospholipid antibody syndrome (APS), aplastic anemia, autoimmune adrenalitis, autoimmune hepatitis, autoimmune oophoritis, autoimmune polyglandular failure, autoimmune thyroiditis, Coeliac disease, Crohn's disease, diabetes mellitus, Goodpasture's syndrome, Graves' disease, Guillain-Barré syndrome (GBS), Hashimoto's disease, idiopathic thrombocytopenic purpura, Kawasaki's disease, lupus erythematosus, multiple sclerosis, myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis, Reiter's syndrome, Sjögren's syndrome, a systemic connective tissue disorder, Takayasu's arteritis, temporal arteritis, warm autoimmune hemolytic anemia, Wegener's granulomatosis, alopecia universalis, Behçet's disease, Chagas' disease, chronic fatigue syndrome, dysautonomia, endometriosis, hidradenitis suppurativa, interstitial cystitis, Lyme disease, neuromyotonia, psoriasis, sarcoidosis, schizophrenia, scleroderma, ulcerative colitis, vitiligo or vulvodynia. In one embodiment, the autoimmune disease is not Coeliac disease, Crohn's disease or ulcerative colitis.

More preferably, the autoimmune disease is selected from acute disseminated encephalitis, Addison's disease, ankylosing spondylitis, antiphospholipid antibody syndrome (APS), aplastic anemia, autoimmune adrenalitis, autoimmune hepatitis, autoimmune oophoritis, autoimmune polyglandular failure, autoimmune thyroiditis, diabetes mellitus, Goodpasture's syndrome, Graves' disease, Guillain-Barré syndrome (GBS), Hashimoto's disease, idiopathic thrombocytopenic purpura, Kawasaki's disease, lupus erythematosus, multiple sclerosis, myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis, Reiter's syndrome, Sjögren's syndrome, a systemic connective tissue disorder, Takayasu's arteritis, temporal arteritis, warm autoimmune hemolytic anemia or Wegener's granulomatosis.

A fourteenth aspect of the present invention provides a compound, a polysaccharide, oligosaccharide, peptide or protein derivative, a mixture, a product, or a pharmaceutical composition of the present invention, for the aid of wound healing. Alternatively, a compound, a polysaccharide, oligosaccharide, peptide or protein derivative, a mixture, or a product of the present invention can be used in the manufacture of a medicament for the aid of wound healing. Also encompassed is a method of aiding wound healing, comprising administering a therapeutically effective amount of a compound, a polysaccharide, oligosaccharide, peptide or protein derivative, a mixture, a product, or a pharmaceutical composition of the present invention, to a patient in need thereof. Also encompassed is a method of modifying the level of a cytokine in vivo, ex vivo or in vitro, said method comprising contacting a compound, a polysaccharide, oligosac-charide, peptide or protein derivative, a mixture, a product, or a pharmaceutical composition of the present invention, with a cell, wherein the method is a method of treating a wound or aiding wound healing.

In one embodiment of the fourteenth aspect of the present invention, the wound is chronic, and/or has arisen from trauma, decubitis, cosmetic surgery, surgical therapy, organ and tissue transplantation, insect bites or burns.

A fifteenth aspect of the present invention provides a compound, a polysaccharide, oligosaccharide, peptide or protein derivative, a mixture, a product, or a pharmaceutical composition of the present invention, for the treatment or prevention of depression. Alternatively, a compound, a polysaccharide, oligosaccharide, peptide or protein derivative, a mixture, or a product of the present invention can be used in the manufacture of a medicament for the treatment or prevention of depression. Also encompassed is a method of treating or preventing depression, comprising administering a therapeutically or prophylactically effective amount of a compound, a polysaccharide, oligosaccharide, peptide or protein derivative, a mixture, a product, or a pharmaceutical composition of the present invention, to a patient in need thereof. Also encompassed is a method of modifying the level of a cytokine in vivo, ex vivo or in vitro, said method comprising contacting a compound, a polysaccharide, oligosaccharide, peptide or protein derivative, a mixture, a product, or a pharmaceutical composition of the present invention, with a cell, wherein the method is a method of treating or preventing depression.

In one embodiment of the fifteenth aspect of the present invention, the depression is a major depressive disorder, preferably catatonic features specification, melancholic features specification, atypical features specification, or psychotic features specification. In other embodiments of the thirteenth aspect of the present invention, the depression is dysthymia, bipolar I disorder, bipolar II disorder, or post-natal depression.

A sixteenth aspect of the present invention provides a compound, a polysaccharide, oligosaccharide, peptide or protein derivative, a mixture, a product, or a pharmaceutical composition of the present invention, for aiding cartilage repair or cartilage regeneration. Alternatively, a compound, a polysaccharide, oligosaccharide, peptide or protein derivative, a mixture, or a product of the present invention can be used in the manufacture of a medicament for aiding cartilage repair or cartilage regeneration.

Also encompassed is a method of aiding cartilage repair or cartilage regeneration, comprising administering a therapeutically effective amount of a compound, a polysaccharide, oligosaccharide, peptide or protein derivative, a mixture, a product, or a pharmaceutical composition of the present invention, to a patient in need thereof. Also encompassed is a method of modifying the level of a cytokine in vivo, ex vivo or in vitro, said method comprising contacting a compound, a polysaccharide, oligosaccharide, peptide or protein derivative, a mixture, a product, or a pharmaceutical composition of the present invention, with a cell, wherein the method is a method of aiding cartilage repair or cartilage regeneration.

In addition to the disorders discussed above, the following is a non-exhaustive list of other disorders and diseases that may be treated, prevented or tested for by compounds, or polysaccharide, oligosaccharide, peptide or protein derivatives, or mixtures, products, pharmaceutical compositions, uses or methods of the present invention, or that may have compounds tested against them by the methods of the present invention: osteochondral defects, post traumatic regeneration injury, ischemia, reperfusion injury, scarring, CNS trauma, spinal section, edema, repetitive strain injuries, tendonitis, carpal tunnel syndrome, alopecia areata, ankylosing spondylitis, antiphospholipid syndrome, autoimmune Addison's disease, aplastic anemia, autoimmune hemolytic anemia, autoimmune hepatitis, Behcet's disease, biliary cirrhosis, bullous pemphigoid, canavan disease, cardiomyopathy, celiac sprue dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, diffuse cerebral sclerosis of schilder, discoid lupus, essential mixed cryoglobulinemia, fibromyalgia fibromyositis, Fuchs heterochromic iridocyclitis, Graves' disease, Guillain-Barré syndrome, Hashimoto's thyroiditis, idiopathic pulmonary fibrosis, idiopathic thrombocytopenia purpura (ITP), IgA nephropathy, insulin dependent diabetes, intermediate uveitis, juvenile arthritis, lichen planus, lupus, Ménière's disease, mixed connective tissue disease, multiple sclerosis, myasthenia gravis, nephrotic syndrome, pemphigus vulgaris, pernicious anemia, polyarteritis nodosa, polychondritis, polyglandular syndrome, polymyalgia rheumatica, polymyositis, dermatomyositis, primary agammaglobulinemia, primary biliary cirrhosis, psoriasis, Raynaud's phenomenon, Reiter's syndrome, rheumatic fever, sarcoidosis, scleroderma, Sjögren's syndrome, stiffman syndrome, Takayasu's arteritis, temporal arteritis, giant cell arteritis, ulcerative colitis, vasculitis, vitiligo, VKH (Vogt-Koyanagi-Harada) disease, Wegener's granulomatosis, anti-phospholipid antibody syndrome (lupus anticoagulant), churg-strauss (allergic granulomatosis), dermatomyositis, polymyositis, Goodpasture's syndrome, interstitial granulomatous dermatitis with arthritis, lupus erythematosus (SLE, DLE, SCLE), mixed connective tissue disease, relapsing polychondritis, HLA-B27 associated conditions, ankylosing spondylitis, psoriasis, ulcerative colitis, IBD, Reiter's syndrome, uveal diseases, uveitis, paediatric uveitis, HLA-B27 associated uveitis, intermediate uveitis, posterior uveitis, iritis, degenerative diseases and disorders, degenerative joint disease, neurodegenerative diseases, inflammatory degenerative diseases, Alzheimer's disease, Huntington's disease, Parkinson's disease, Creutzfeldt-Jakob disease, viral diseases related to paramyxovirus, picornavirus, rhinovirus, coxsackie virus, influenza virus, herpes virus (including herpes I, herpes II, herpes zoster (shingles), herpetic conjunctivitis, keratitis, and genital herpes), adenovirus, parainfluenza virus, respiratory syncytial virus, echovirus, coronavirus, Epstein-Barr virus, cytomegalovirus, varicella zoster virus, hepatitis variants (including hepatitis C virus (HCV), hepatitis A virus (HAV), hepatitis B virus (HBV), hepatitis D virus (HDV), hepatitis E virus (HEV), hepatitis F virus (HFV), hepatitis G virus (HGV)), human immunodeficiency virus; neoplastic diseases, leukemia, lymphoma, myeloma, hepatomas, other major organ carcinomas and sarcomas, glioma, neuroblastoma, astrocytic and glial tumours, invasive and non-invasive tumours (anaplastic (malignant) astrocytoma, glioblastoma multiforme variants, giant cell glioblastoma, gliosarcoma, pilocytic astrocytoma, subependymal giant cell astrocytoma, pleomorphic xanthoastrocytoma), oligodendroglial tumours, ependymal cell tumours, mixed gliomas, neuroepithelial tumours of uncertain origin, tumours of the choroid plexus, neuronal and mixed neuronal-glial tumours, pineal parenchyma tumours, tumours with neuroblastic or glioblastic elements (embryonal tumours), neuroblastoma, ganglioneuroblastoma, tumours of the sellar region, hematopoietic tumours, primary malignant lymphomas, plasmacytoma, granulocytic sarcoma, germ cell tumours, tumours of the meninges, allergies, rhinitis, bronchitis, asthma, conditions relating to excessively active or stimulated eosinophils, disorders related to transplants (such as renal, hepatic, corneal, cartilage, stem cell, chondrocyte, pulmonary, cardiac, vascular, and myeloid transplants), hypoglycemia, myocarditis (Chagas' disease and coxsackie myocarditis), autoimmune hemolytic anemia, idiopathic thrombocytopenic purpura autoimmune neutropenia, sperm and testicular autoimmunity, intradermal infection (optionally with allergic reactions), acute and chronic bacterial infections (optionally with allergic reactions), skin contact hypersensitivities, optic contact hypersensitivities, leprosy and other mycobacterium infections, eczema acne, chicken pox, hypertension, adrenal autoimmunity, myasthenia gravis, and myositis.

In any aspect of the present invention relating to treatment, prevention, or testing, the inflammation, disorder or disease to be treated, prevented or tested for may be non-gastrointestinal. Alternatively, the inflammation, disorder or disease to be treated, prevented or tested for may be gastrointestinal.

As used herein, the terms 'gastrointestinal' and 'gastrointestines' refer to any part of the stomach and any part of the alimentary canal thereafter, including the small intestine, large intestine and any other intestines if any, but not to any part of the alimentary canal prior to the stomach such as the mouth, pharynx or oesophagus. The term 'alimentary canal' refers to the passage along which food passes through the body from the mouth to the anus.

Thus, 'non-gastrointestinal inflammation' refers to inflammation occurring in any part of a body other than the gastrointestines, including inflammation of any other part of the alimentary canal. In some embodiments of the present invention, inflammation of the entire alimentary canal is excluded, in which case the inflammation is referred to as 'non-alimentary canal inflammation'.

Similarly, the term 'non-gastrointestinal disorder or disease' refers to disorders or diseases to the extent that they occur in any part of a body other than the gastrointestines, including disorders or diseases occurring in any other part of the alimentary canal. Non-gastrointestinal disorders or diseases may display some symptoms in the gastrointestines.

Optionally, disorders or diseases which display symptoms in the gastrointestines may be excluded from the scope of the present invention. Thus, in one embodiment of the present invention, the disorder or disease to be treated or prevented is a 'non-gastrointestinal disorder or disease without symptoms in the gastrointestines'.

In some embodiments of the present invention, disorders or diseases to the extent that they occur in the entire alimentary canal are excluded from the scope of the present invention, in which case the disorder or disease to be treated or prevented is referred to as a 'non-alimentary canal disorder or disease'. Non-alimentary canal disorders or diseases may display some symptoms in the alimentary canal.

Optionally, disorders or diseases which display symptoms in the alimentary canal may be excluded from the scope of the present invention. Thus, in one embodiment of the present invention, the disorder or disease to be treated is a 'non-alimentary canal disorder or disease without symptoms in the alimentary canal'.

In any aspect of the present invention relating to treatment, prevention, or testing, the treatment of, prevention of, or test for inflammation, a disorder or a disease may be performed via gastrointestinal absorption of the compounds, or polysaccharide, oligosaccharide, peptide or protein derivatives, or mixtures, products or pharmaceutical compositions of the present invention The term 'gastrointestinal absorption' of the compounds of the present invention refers to absorption that occurs systemically via the gastrointestines. To achieve gastrointestinal absorption, the compounds of the present invention may be administered, for example, orally, rectally or by tube feeding. Preferably the administration is oral.

In any of the eighth to sixteenth aspects of the present invention, the patient to be treated can be a mammal, preferably a human.

A seventeenth aspect of the present invention provides a compound, a polysaccharide, oligosaccharide, peptide or protein derivative, a mixture, a product, or a pharmaceutical composition of the present invention, for the performance of a laboratory test. Alternatively, a compound, a polysaccharide, oligosaccharide, peptide or protein derivative, a mixture, or a product of the present invention can be used in the manufacture of a diagnostic agent for the performance of a laboratory test. Also encompassed is a method of performing a laboratory test, comprising administering a compound, a polysaccharide, oligosaccharide, peptide or protein derivative, a mixture, a product, or a pharmaceutical composition of the present invention, to a subject to be tested.

In one embodiment of the seventeenth aspect of the present invention, the testing occurs in vitro, ex vivo or in vivo. In another embodiment, the subject to be tested is a mammal, which can be either a human or a non-human.

In any embodiment of the eleventh and seventeenth aspect of the present invention, where the patient or subject to be tested is a mammal, the mammal can be either a human or a non-human. In one embodiment, a non-human subject is mutilated or sacrificed as a result of the test.

Any of the medicaments employed in the present invention can be administered by oral, parental (including intravenous, subcutaneous, intramuscular, intradermal, intratracheal, intraperitoneal, intraarticular, intracranial and epidural), transdermal, airway (aerosol), rectal, vaginal or topical (including buccal, mucosal and sublingual) administration.

Preferably, the mode of administration selected is that most appropriate to the disorder or disease to be treated or prevented. For example, oral administration may be preferred for the treatment or prevention of rheumatoid arthritis, oral or topical administration may be preferred for the treatment or prevention of psoriasis, and airway administration may be preferred for the treatment or prevention of asthma.

For oral administration, the compounds, or polysaccharide, oligosaccharide, peptide or protein derivatives, or mixtures, products, or pharmaceutical compositions of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, or polysaccharide, oligosaccharide, peptide or protein derivatives, or mixtures, products, or pharmaceutical compositions of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For topical and transdermal administration, the compounds, or polysaccharide, oligosaccharide, peptide or protein derivatives, or mixtures, products, or pharmaceutical compositions of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, or polysaccharide, oligosaccharide, peptide or protein derivatives, or mixtures, products, or pharmaceutical compositions of the present invention will, of course, vary with the disorder or disease to be treated or prevented. In general, a suitable dose will be in the range of 0.01 to 500 mg per kilogram body weight of the recipient per day, preferably in the range of 1.0 to 200 mg per kilogram body weight per day, preferably 50 to 100 mg per kilogram body weight per day. The desired dose is preferably presented once a day, but may be dosed as two, three, four, five, six or more sub-doses administered at appropriate intervals throughout the day. These sub-doses may be administered in unit dosage forms, for example, containing 1 mg to 20 g, preferably 100 mg to 10 g, preferably 1 g to 5 g of active ingredient per unit dosage form.

A final aspect of the present invention relates to a unit dosage form comprising at least 1 mg of a compound, a polysaccharide, oligosaccharide, peptide or protein derivative, a mixture or a product of any one of the preceding aspects of the present invention. Preferably, the unit dosage form is suitable for oral administration. Preferably, the unit dosage form comprises at least 10 mg, at least 100 mg, at least 500 mg, at least 1 g, at least 2.5 g, at least 5 g, at least 7.5 g, at least 10 g, at least 20 g or at least 50 g of a compound, a polysaccharide, oligosaccharide, peptide or protein derivative, a mixture or a product of any one of the preceding aspects of the present invention.

The invention will now be described with reference to the following examples. It will be appreciated that what follows is by way of example only and that modifications to detail may be made whilst still falling within the scope of the invention.

Figure 1:
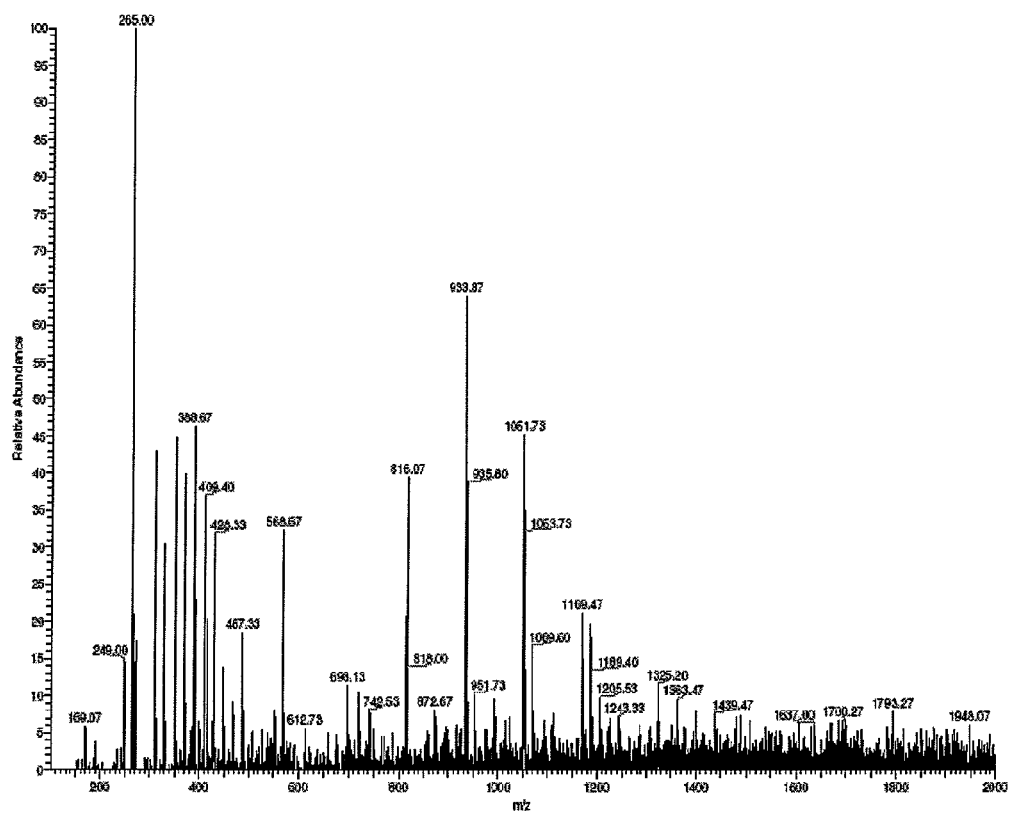
FIG. 1 shows the mass spectrum of the multi-potassium salt of four- to six-fold sulphated N-acetyl-β,β-diglucosylamine.

The following paragraphs enumerated consecutively from 1 through 158 provide for various aspects of the present invention. In one embodiment, the present invention provides:

1. A compound comprising:
(i) at least one monosaccharide subunit comprising a glycosidic —NR$_2$ group, a glycosidic —NR$_3^+$ group, a directly bonded =NR group, or a directly bonded =NR$_2^+$ group, wherein each R is independently hydrogen, a —SO$_2$—OR' or —SO$_2$—N(R')$_2$ group, a further monosaccharide subunit, or a hydrocarbyl group, or two or three R groups and the nitrogen atom to which they are attached, together form a further monosaccharide subunit or a cyclic hydrocarbyl group; and
(ii) at least one sulphate group, wherein a sulphate group is a —O—SO$_2$—OR', —NR'—SO$_2$—OR', —O—SO$_2$—N(R')$_2$ or —NR'—SO$_2$—N(R')$_2$ group;
wherein each R' is independently hydrogen, a metal, a further monosaccharide subunit, or a hydrocarbyl group;
wherein each monosaccharide subunit independently is optionally substituted and/or optionally modified; and
wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;
or a salt thereof;
provided that the compound is not 3'-phosphoadenosine-5'-phosphosulphate.

2. A compound of paragraph 1, comprising:
(i) at least one monosaccharide subunit comprising a glycosidic —NR$_2$ group, a glycosidic —NR$_3^+$ group, a directly bonded =NR group, or a directly bonded =NR$_2^+$ group, wherein each R is independently hydrogen, a —SO$_2$—OR' or —SO$_2$—N(R')$_2$ group, a further monosaccharide subunit, or a hydrocarbyl group, or two or three R groups and the nitrogen atom to which they are attached, together form a further monosaccharide subunit or a cyclic hydrocarbyl group, provided that the glycosidic —NR$_2$ group is not —NHacyl; and
(ii) at least one sulphate group, wherein a sulphate group is a —O—SO$_2$—OR', —NR'—SO$_2$—OR', —O—SO$_2$—N(R')$_2$ or —NR'—SO$_2$—N(R')$_2$ group;
wherein each R' is independently hydrogen, a metal, a further monosaccharide subunit, or a hydrocarbyl group;
wherein each monosaccharide subunit independently is optionally substituted and/or optionally modified; and
wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the compound is not 3'-phosphoadenosine-5'-phosphosulphate; and provided that the at least one monosaccharide subunit is not substituted with an —OR''' group, wherein R''' is any group comprising a further pyranosyl or furanosyl monosaccharide subunit.

3. A compound of paragraph 1 or 2, wherein each R is independently hydrogen, a further monosaccharide subunit, or a hydrocarbyl group, or two or three R groups and the nitrogen atom to which they are attached, together form a further monosaccharide subunit or a cyclic hydrocarbyl group.

4. A compound of paragraph 1, comprising:

(i) at least one monosaccharide subunit comprising a glycosidic —NR$_2$ group, a glycosidic —NR$_3^+$ group, a directly bonded =NR group, or a directly bonded =NR$_2^+$ group, wherein each R is independently hydrogen, a —SO$_2$—OR' or —SO$_2$—N(R')$_2$ group, a further monosaccharide subunit, or a $C_1$-$C_7$ hydrocarbyl group, or two or three R groups and the nitrogen atom to which they are attached, together form a further monosaccharide subunit or a cyclic hydrocarbyl group; and (ii) at least one sulphate group, wherein a sulphate group is a —O—SO$_2$—OR', —NR'—SO$_2$—OR', —O—SO$_2$—N(R')$_2$ or —NR'—SO$_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the compound is not 3'-phosphoadenosine-5'-phosphosulphate; and provided that the at least one monosaccharide subunit is not substituted with an —OR''' group, wherein R''' is any group comprising a further pyranosyl or furanosyl monosaccharide subunit.

5. A compound of paragraph 1, comprising:

(i) at least one monosaccharide subunit comprising a glycosidic —NR$_2$ group, a glycosidic —NR$_3^+$ group, a directly bonded =NR group, or a directly bonded =NR$_2^+$ group, wherein each R is independently hydrogen, a —SO$_2$—OR' or —SO$_2$—N(R')$_2$ group, a further monosaccharide subunit, or a $C_1$-$C_7$ hydrocarbyl group, or two or three R groups and the nitrogen atom to which they are attached, together form a further monosaccharide subunit or a cyclic hydrocarbyl group; and (ii) at least one sulphate group, wherein a sulphate group is a —O—SO$_2$—OR', —NR'—SO$_2$—OR', —O—SO$_2$—N(R')$_2$ or —NR'—SO$_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof;

provided that the at least one monosaccharide subunit is not N-substituted a to said glycosidic —NR$_2$ group, glycosidic —NR$_3^+$ group, directly bonded =NR group, or directly bonded =NR$_2^+$ group.

6. A compound of paragraph 4 or 5, wherein each R is independently hydrogen, a further monosaccharide subunit, or a $C_1$-$C_7$ hydrocarbyl group, or two or three R groups and the nitrogen atom to which they are attached, together form a further monosaccharide subunit or a cyclic hydrocarbyl group.

7. A compound comprising:

(i) a sequence of at least two monosaccharide subunits linked by a glycosidic —NR— group, a glycosidic —NR$_2^+$— group, a directly bonded =N— group, or a directly bonded =NR$^+$— group, wherein each R is independently hydrogen, a —SO$_2$—OR' or —SO$_2$—N(R')$_2$ group, a further monosaccharide subunit, or a hydrocarbyl group, or two R groups and the nitrogen atom to which they are attached, together form a further monosaccharide subunit or a cyclic hydrocarbyl group; and (ii) at least one sulphate group, wherein a sulphate group is a —O—SO$_2$—OR', —NR'—SO$_2$—OR', —O—SO$_2$—N(R')$_2$ or —NR'—SO$_2$—N(R')$_2$ group;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

or a salt thereof.

8. A compound of paragraph 7, wherein the glycosidic —NR— group or the glycosidic —NR$_2^+$— group is linked to one or both of the monosaccharide subunits by a glycosidic bond.

9. A compound of paragraph 7, wherein the directly bonded =N— group or the directly bonded =NR$^+$— group is linked to one or neither of the monosaccharide subunits by a glycosidic bond.

10. A compound of paragraph 7 or 8, wherein each R is independently hydrogen, a further monosaccharide subunit, or a hydrocarbyl group, or two R groups and the nitrogen atom to which they are attached, together form a further monosaccharide subunit or a cyclic hydrocarbyl group.

11. A compound of any of the preceding paragraphs, wherein all monosaccharide subunits are independently ring-closed or open-chain or a mixture of ring-closed and open-chain.

12. A compound of any of the preceding paragraphs, wherein one or more monosaccharide subunit is substituted and/or modified.

13. A compound of any of the preceding paragraphs, wherein in a substituted monosaccharide subunit:

(a) independently one or more of the hydroxyl groups of the monosaccharide subunit is replaced with —H, —F, —Cl, —Br, —I, —CF$_3$, —CCl$_3$, —CBr$_3$, —CI$_3$, —SH, —NH$_2$, —N$_3$, —NH—NH$_2$, —CN, —NO$_2$, —COOH, —R$^a$—O—R$^b$, —R$^a$—S—R$^b$, —R$^a$—SO—R$^b$, —R$^a$—SO$_2$—R$^b$, —R$^a$—SO$_2$—OR$^b$, —R$^a$O—SO$_2$—R$^b$, —R$^a$—SO$_2$—N(R$^b$)$_2$, —R$^a$—NR$^b$—SO$_2$—R$^b$, —R$^a$O—SO$_2$—OR$^b$, —R$^a$O—SO$_2$—N(R$^b$)$_2$, —R$^a$—NR$^b$—SO$_2$—OR$^b$, —R$^a$—

$-NR^b-SO_2-N(R^b)_2$, $-R^a-N(R^b)_2$, $-R^a-N(R^b)_3{}^+$, $-R^a-B(R^b)_2$, $-R^a-P(R^b)_2$, $-R^a-PO(R^b)_2$, $-R^a-Si(R^b)_3$, $-R^a-CO-R^b$, $-R^a-CO-OR^b$, $-R^aO-CO-R^b$, $-R^a-CO-N(R^b)_2$, $-R^a-NR^b-CO-R^b$, $-R^aO-CO-OR^b$, $-R^aO-CO-N(R^b)_2$, $-R^a-NR^b-CO-OR^b$, $-R^a-NR^b-CO-N(R^b)_2$, $-R^a-CS-R^b$, $-R^a-CS-OR^b$, $-R^aO-CS-R^b$, $-R^a-CS-N(R^b)_2$, $-R^a-NR^b-CS-R^b$, $-R^aO-CS-OR^b$, $-R^aO-CS-N(R^b)_2$, $-R^a-NR^b-CS-OR^b$, $-R^a-NR^b-CS-N(R^b)_2$, or $-R^b$; and/or (b) independently one, two or three of the hydrogens of the monosaccharide subunit is replaced with $-F$, $-Cl$, $-Br$, $-I$, $-CF_3$, $-CCl_3$, $-CBr_3$, $-CI_3$, $-OH$, $-SH$, $-NH_2$, $-N_3$, $-NH=NH_2$, $-CN$, $-NO_2$, $-COOH$, $-R^a-O-R^b$, $-R^a-S-R^b$, $-R^a-SO-R^b$, $-R^a-SO_2-R^b$, $-R^a-SO_2-OR^b$, $-R^aO-SO_2-R^b$, $-R^a-SO_2-N(R)_2$, $-R^a-NR^b-SO_2-R^b$, $-R^aO-SO_2-OR^b$, $-R^aO-SO_2-N(R)_2$, $-R^a-NR^b-SO_2-OR^b$, $-R^a-NR^b-SO_2-N(R^b)_2$, $-R^a-N(R^b)_2$, $-R^a-N(R^b)_3{}^+$, $-R^a-B(R^b)_2$, $-R^a-P(R^b)_2$, $-R^a-PO(R^b)_2$, $-R^a-Si(R^b)_3$, $-R^a-CO-R^b$, $-R^a-CO-OR^b$, $-R^aO-CO-R^b$, $-R^a-CO-N(R^b)_2$, $-R^a-NR^b-CO-R^b$, $-R^aO-CO-OR^b$, $-R^aO-CO-N(R^b)_2$, $-R^a-NR^b-CO-OR^b$, $-R^a-NR^b-CO-N(R^b)_2$, $-R^a-CS-R^b$, $-R^a-CS-OR^b$, $-R^aO-CS-R^b$, $-R^a-CS-N(R^b)_2$, $-R^a-NR^b-CS-R^b$, $-R^aO-CS-OR^b$, $-R^aO-CS-N(R^b)_2$, $-R^a-NR^b-CS-OR^b$, $-R^a-NR^b-CS-N(R^b)_2$, or $-R^b$; and/or (c) independently one or more of the hydroxyl groups of the monosaccharide subunit, together with the hydrogen attached to the same carbon atom as the hydroxyl group, is replaced with $=O$, $=S$, $=NR^b$, or $=N(R^b)_2{}^+$; and/or (d) independently two hydroxyl groups of the monosaccharide subunit are together replaced with $-O-R^c-$, $-S-R^c-$, $-SO-R^c-$, $-SO_2-R^c-$, or $-NR^b-R^c-$;

wherein:

$-R^a-$ is independently a chemical bond, or a substituted or unsubstituted alkylene, alkenylene or alkynylene group which optionally includes one or more heteroatoms in its carbon skeleton;

$-R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

$-R^c-$ is independently a chemical bond, or a substituted or unsubstituted alkylene, alkenylene or alkynylene group which optionally includes one or more heteroatoms in its carbon skeleton; and M is a metal;

provided that the monosaccharide subunit comprises at least one $-OR^b$, $-OSOR^b$, $-OSO_2R^b$, $-OSO_3R^b$, $-OSi(R^b)_3$, $-OCOR^b$, $-OCO_2R^b$, or $-OM$.

14. A compound of any of the preceding paragraphs, wherein in a modified monosaccharide subunit:

(a) the ring of the modified monosaccharide subunit, or what would be the ring in the ring-closed form of the modified monosaccharide subunit, is partially unsaturated; and/or (b) the ring oxygen of the modified monosaccharide subunit, or what would be the ring oxygen in the ring-closed form of the modified monosaccharide subunit, is replaced with $-S-$ or $-NR^b-$, wherein $-R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

15. A compound of any of the preceding paragraphs, wherein each hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton.

16. A compound of paragraph 15, wherein a substituted hydrocarbyl group is substituted with one or more of $-F$, $-Cl$, $-Br$, $-I$, $-CF_3$, $-CCl_3$, $-CBr_3$, $-CI_3$, $-OH$, $-SH$, $-NH_2$, $-N_3$, $-NH=NH_2$, $-CN$, $-NO_2$, $-COOH$, $-R^a-O-R^b$, $-R^a-S-R^b$, $-R^a-SO-R^b$, $-R^a-SO_2-R^b$, $-R^a-SO_2-OR^b$, $-R^aO-SO_2-R^b$, $-R^a-SO_2-N(R^b)_2$, $-R^a-NR^b-SO_2-R^b$, $-R^aO-SO_2-OR^b$, $-R^aO-SO_2-N(R^b)_2$, $-R^a-NR^b-SO_2-OR^b$, $-R^a-NR^b-SO_2-N(R)_2$, $-R^a-N(R^b)_2$, $-R^a-N(R^b)_3{}^+$, $-R^a-B(R^b)_2$, $-R^a-P(R^b)_2$, $-R^a-PO(R^b)_2$, $-R^a-Si(R^b)_3$, $-R^a-CO-R^b$, $-R^a-CO-OR^b$, $-R^aO-CO-R^b$, $-R^a-CO-N(R^b)_2$, $-R^a-NR^b-CO-R^b$, $-R^aO-CO-OR^b$, $-R^aO-CO-N(R^b)_2$, $-R^a-NR^b-CO-OR^b$, $-R^a-NR^b-CO-N(R^b)_2$, $-R^a-CS-R^b$, $-R^a-CS-OR^b$, $-R^aO-CS-R^b$, $-R^a-CS-N(R^b)_2$, $-R^a-NR^b-CS-R^b$, $-R^aO-CS-OR^b$, $-R^aO-CS-N(R^b)_2$, $-R^a-NR^b-CS-OR^b$, $-R^a-NR^b-CS-N(R^b)_2$, $-R^b$, or a monosaccharide subunit;

wherein:

$-R^a-$ is independently a chemical bond, or a substituted or unsubstituted alkylene, alkenylene or alkynylene group which optionally includes one or more heteroatoms in its carbon skeleton; and $-R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

17. A compound of any of the preceding paragraphs, wherein the compound is a pharmaceutically acceptable salt.

18. A compound of any of the preceding paragraphs, wherein the compound comprises at least one monosaccharide subunit comprising a glycosidic $-NR_2$ group or a directly bonded $=NR$ group.

19. A compound of any of the preceding paragraphs, wherein the compound comprises a sequence of at least two monosaccharide subunits linked by a glycosidic $-NR-$ group or a directly bonded $=N-$ group.

20. A compound of any of the preceding paragraphs, wherein (a) one R group is not hydrogen; and/or (b) two R groups are not hydrogen; and/or (c) one R group is a monosaccharide subunit and one R group is a hydrocarbyl group; and/or (d) one R group is a monosaccharide subunit and one R group is hydrogen; and/or (e) one R group is a hydrocarbyl group and one R group is hydrogen; and/or (f) two R groups are independently monosaccharide subunits; and/or (g) two R groups are independently hydrocarbyl groups; and/or (h) one or two R groups are independently hydrogen, or an alkyl, acyl or alkoxycarbonyl group; and/or (i) one or two R groups are independently hydrogen, or a $C_1$-$C_6$ alkyl, $C_2$-$C_6$ acyl, $C_2$-$C_6$ halo-acyl, or $C_{1-20}$ alkoxycarbonyl group; and/or (j) one or two R groups are independently a methyl, ethyl, acetyl, trifluoroacetyl, Boc, Fmoc, or Zervas group.

21. A compound of any of the preceding paragraphs, comprising at least two or at least three sulphate groups.

22. A compound of any of the preceding paragraphs, comprising at least one —O—$SO_2$—OR', —NR'—$SO_2$—OR', or —O—$SO_2$—N(R')$_2$ group.

23. A compound of any of the preceding paragraphs, comprising at least one —$OSO_3$R' group.

24. A compound of any of the preceding paragraphs, comprising at least two monosaccharide subunits, each of which is substituted with at least one sulphate group.

25. A compound of any of the preceding paragraphs, comprising at least one pyranosyl subunit, which is substituted with one, two or three sulphate groups in the 2-, 3- and/or 6-position relative to the anomeric carbon of the pyranosyl subunit.

26. A compound of paragraph 25, wherein the pyranosyl subunit is substituted with two or three sulphate groups in the 2-, 3- and/or 6-position relative to the anomeric carbon of the pyranosyl subunit.

27. A compound of paragraph 25 or 26, wherein the pyranosyl subunit is part of a disaccharide.

28. A compound of any of the preceding paragraphs, comprising a first pyranosyl subunit, which is substituted with one sulphate group in the 2- or 6-position relative to the anomeric carbon of the pyranosyl subunit, and a second pyranosyl subunit, which is substituted with one sulphate group in the 2- or 3-position relative to the anomeric carbon of the pyranosyl subunit and one sulphate group in the 6-position relative to the anomeric carbon of the pyranosyl subunit.

29. A compound of paragraph 28, wherein the first and second pyranosyl subunits form a disaccharide.

30. A compound of any of the preceding paragraphs, comprising at least one pyranosyl subunit, which is substituted with one or two sulphate groups in the 4- and/or 6-position relative to the anomeric carbon of the pyranosyl subunit.

31. A compound of paragraph 30, wherein the pyranosyl subunit is part of an oligosaccharide or a polysaccharide.

32. A compound of any of the preceding paragraphs, comprising at least one, two or three sulphate groups, located on primary hydroxyl positions.

33. A compound of any of the preceding paragraphs, wherein a sulphate group is provided on a monosaccharide subunit comprising a glycosidic amine group.

34. A compound of any of the preceding paragraphs, wherein 1-50, or 2-30, or 3-15, or 6-12, or all the hydroxyl groups on the monosaccharide subunits independently have been replaced with a sulphate group.

35. A compound of any of the preceding paragraphs, wherein 1-9, or 2-8, or 3-4 hydroxyl groups on each of 1, 2, 3, 4, 5, 6, 7, 8, or all monosaccharide subunits independently have been replaced with a sulphate group.

36. A compound of any of the preceding paragraphs, wherein the compound is a partially or fully sulphated saccharide.

37. A compound of any of the preceding paragraphs, wherein R' is independently hydrogen, a metal, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

38. A compound of any of the preceding paragraphs, wherein R' is independently hydrogen, an alkali metal, an earth alkali metal, copper, silver, zinc, or a $C_1$-$C_6$ alkyl group.

39. A compound of any of the preceding paragraphs, comprising 1-100, 1-20, 2-10, or 2-4 monosaccharide subunits.

40. A compound of any of the preceding paragraphs, comprising 1, 2, 3, 4, 5, 6, 7, 8, 9, 10 or more monosaccharide subunits.

41. A compound of any of the preceding paragraphs, comprising a sequence of 1, 2, 3, 4, 5, 6, 7, 8, 9, 10 or more monosaccharide subunits.

42. A compound of any of the preceding paragraphs, wherein all monosaccharide subunits are independently aldosyl or ketosyl monosaccharides.

43. A compound of paragraph 42, wherein 1, 2, 3, 4, or all monosaccharide subunits are independently triosyl, tetrosyl, pentosyl, hexosyl, heptosyl, octosyl or nonosyl monosaccharides.

44. A compound of paragraph 43, wherein 1, 2, 3, 4, or all monosaccharide subunits are independently glycerosyl, erythrosyl, threosyl, ribosyl, arabinosyl, xylosyl, lyxosyl, allosyl, altrosyl, glucosyl, mannosyl, gulosyl, idosyl, galactosyl, talosyl, rhamnosyl or fucosyl monosaccharides.

45. A compound of any of the preceding paragraphs, wherein all monosaccharide subunits are independently in the D- or L-configuration.

46. A compound of any of the preceding paragraphs, wherein 1, 2, 3, 4, or all monosaccharide subunits are independently tetrosyl monosaccharides or higher, and the ring of those monosaccharides is furanosyl.

47. A compound of any of the preceding paragraphs, wherein 1, 2, 3, 4, or all monosaccharide subunits are independently pentosyl monosaccharides or higher, and the ring of those monosaccharides is pyranosyl.

48. A compound of any of the preceding paragraphs, wherein the stereochemistry of each glycosidic bond is independently α or β.

49. A compound of any of the preceding paragraphs, wherein the compound is:

(a) a glucosylamine;

(b) β,β-di-glucosylamine;

(c) a mono-, di-, tri-, tetra-, penta-, hexa-, hepta- or octa-sulphated β,β-di-glucosylamine, or a mixture thereof;

(d) a mono-, di-, tri-, tetra-, penta-, hexa-, hepta- or octa-sulphated N-acetyl-β,β-di-glucosylamine, or a mixture thereof;

(e) a mono-, di-, tri-, tetra-, penta-, hexa-, hepta- or octa-sulphated N-ethyl-β,β-di-glucosylamine, or a mixture thereof;

(f) a sulphated di-(4,4'-glucosylglucosyl)amine;

(g) 1-benzamido-1-deoxy-2,3,4,6-tetra potassium sulphonatoglucose; or (h) 1-N-octyl-1-N-decanoyl-1-amino-1-deoxy-6-potassium sulphonate-muramyl-D-isoglutamyl-alanine.

50. A compound of any of the preceding paragraphs, wherein two R groups and the nitrogen atom to which they are attached, together do not form a heterocyclic aromatic group.

51. A compound of any of the preceding paragraphs, wherein the atom connectivity S—O—P is not present in any monosaccharide subunit and/or in the entire compound.

52. A compound of any of the preceding paragraphs, wherein the compound does not contain the group —O—P(=O)(OH)—O—$SO_2$OH.

53. A compound of any of the preceding paragraphs, wherein the compound is not a nucleoside and/or not a nucleotide.

54. A compound of any of the preceding paragraphs, wherein the compound does not comprise a ribose subunit comprising a glycosidic tertiary amine.

55. A compound having the formula (I):

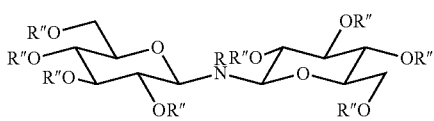

wherein:
R is Ac, Me, Et, COCF$_3$, or COPh;
each R" is SO$_3$R' or H with at least one R" being SO$_3$R'; and
each R' is H, Li, Na or K;
or a tautomer, a stereoisomer or a salt thereof.

56. A compound having the formula (II):

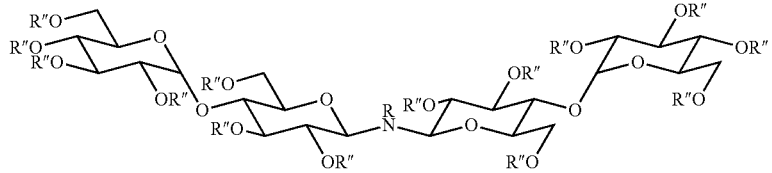

wherein:
R is Ac, Me, Et, COCF$_3$, or COPh;
each R" is SO$_3$R' or H with at least one R" being SO$_3$R'; and
each R' is H, Li, Na or K;
or a tautomer, a stereoisomer or a salt thereof.

57. A compound having the formula (III):

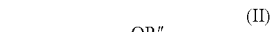
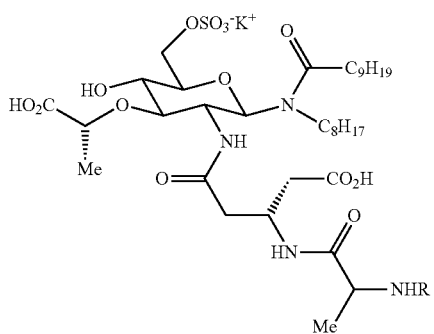

wherein R is H, CHO or COMe;
or a tautomer, a stereoisomer or a salt thereof.

58. A compound having the formula (IV):

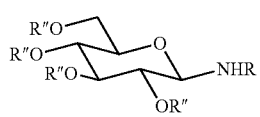

wherein:
R is Ac, Me, Et, COCF$_3$, or COPh;
each R" is SO$_3$R' or H with at least one R" being SO$_3$R'; and
each R' is H, Li, Na or K;
or a tautomer, a stereoisomer or a salt thereof.

59. A polysaccharide, oligosaccharide, peptide or protein derivative comprising a polysaccharide, oligosaccharide, peptide or protein covalently linked to a compound of any of paragraphs 1 to 58.

60. A mixture of compounds of any of paragraphs 1 to 58, or a mixture of polysaccharide, oligosaccharide, peptide or protein derivatives of paragraph 59, wherein the compounds or derivatives differ only in their stereochemistry at the anomeric centre and/or in their degree of sulphation and/or their position of sulphation.

61. A mixture of paragraph 60, wherein 50%, 75%, 80%, 85%, 90%, 95% or 99% of the compounds or derivatives lie within three consecutive degrees of sulphation.

62. A mixture of paragraph 61, wherein the three consecutive degrees of sulphation are three- to five-fold sulphation, four- to six-fold sulphation, or five- to seven-fold sulphation.

63. A method of synthesising a compound of any of paragraphs 1 to 58, comprising the sulphation of a compound comprising:

(a) at least one monosaccharide subunit comprising a glycosidic —NR$_2$ group, a glycosidic —NR$_3^+$ group, a directly bonded =NR group, or a directly bonded =NR$_2^+$ group, wherein each R is independently hydrogen, a —SO$_2$—OR' or —SO$_2$—N(R')$_2$ group, a further monosaccharide subunit, or a hydrocarbyl group, or two or three R groups and the nitrogen atom to which they are attached, together form a further monosaccharide subunit or a cyclic hydrocarbyl group; or a salt thereof; provided that the compound is not 3'-phosphoadenosine-5'-phosphosulphate;

(b) a sequence of at least two monosaccharide subunits linked by a glycosidic —NR— group, a glycosidic —NR$_2^+$— group, a directly bonded =N— group, or a directly bonded =NR$^+$— group, wherein each R is independently hydrogen, a —SO$_2$—OR' or —SO$_2$—N(R')$_2$ group, a further monosaccharide subunit, or a hydrocarbyl group, or two R groups and the nitrogen atom to which they are attached, together form a further monosaccharide subunit or a cyclic hydrocarbyl group; or a salt thereof;

wherein each R' is independently hydrogen, a metal, a further monosaccharide subunit, or a hydrocarbyl group;

wherein each monosaccharide subunit independently is optionally substituted and/or optionally modified; and wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

64. A method of paragraph 63, wherein the compound is O- and/or N-protected prior to sulphation.

65. A method of paragraph 64, wherein O-silyl, O-acetyl, O-acyl, O-acetal, O-ketal, O-benzyl, O-benzoyl or O-THP protection is used.

66. A method of paragraph 64, wherein N-Boc, N-Fmoc, N-Zervas, N-acetyl, N-acyl, N-alkyl or N-trifluoroacetyl protection is used.

67. A method of any of paragraphs 63 to 66, wherein the sulphation is performed using sulphur trioxide complexed to a nitrogen-containing base.

68. A method of paragraph 67, wherein the nitrogen-containing base is pyridine.

69. A method of paragraph 68, wherein pyridine is used as solvent.

70. A method of any of paragraphs 63 to 66, wherein the sulphation is performed using a halosulphonic acid or a silyl-protected halosulphonic acid.

71. A method of paragraph 70, wherein the halosulphonic acid or silyl-protected halosulphonic acid is chlorosulphonic acid or trimethylsilylchlorosulphonate respectively.

72. A product produced by a method of any of paragraphs 63 to 71.

73. A pharmaceutical composition comprising a compound of any of paragraphs 1 to 58, a polysaccharide, oligosaccharide, peptide or protein derivative of paragraph 59, a mixture of any of paragraphs 60 to 62, or a product of paragraph 72, and a pharmaceutically acceptable excipient, carrier or diluent.

74. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for use in medicine.

75. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for binding to a macromolecule.

76. A compound, derivative, mixture, product or pharmaceutical composition of paragraph 75, wherein the macromolecule is a protein, peptide, nucleic acid, lipid, polysaccharide, oligosaccharide, glycosaminoglycan, or proteoglycan.

77. A compound, derivative, mixture, product or pharmaceutical composition of paragraph 75 or 76, wherein the binding results in inhibition, activation, modification, destruction, re-folding, denaturisation, aggregation, or oligomerisation of the macromolecule.

78. Use of a compound of any of paragraphs 1 to 58, a polysaccharide, oligosaccharide, peptide or protein derivative of paragraph 59, a mixture of any of paragraphs 60 to 62, or a product of paragraph 72, in the manufacture of a medicament for the inhibition, activation, modification, destruction, re-folding, denaturisation, aggregation, or oligomerisation of a macromolecule.

79. A method of inhibiting, activating, modifying, destroying, re-folding, denaturising, aggregating, or oligomerising a macromolecule, comprising administering an effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

80. A compound, derivative, mixture, product, pharmaceutical composition, use or method of any of paragraphs 75 to 79, wherein the binding occurs in vitro, ex vivo or in vivo.

81. A compound, derivative, mixture, product, pharmaceutical composition, use or method of any of paragraphs 75 to 80, wherein the macromolecule is a member of the lectin family of proteins.

82. A compound, derivative, mixture, product, pharmaceutical composition, use or method of any of paragraphs 75 to 81, wherein the macromolecule is a transmembrane glycoprotein.

83. A compound, derivative, mixture, product, pharmaceutical composition, use or method of any of paragraphs 75 to 80, wherein the protein is a member of the selectin sub-class.

84. A compound, derivative, mixture, product, pharmaceutical composition, use or method of paragraph 83, wherein the selectin is an E-, L- or P-selectin.

85. A compound, derivative, mixture, product, pharmaceutical composition, use or method of any of paragraphs 75 to 80, wherein the protein is a member of the siglecs sub-class.

86. A compound, derivative, mixture, product, pharmaceutical composition, use or method of any of paragraphs 75 to 80, wherein the macromolecule is a mannose binding protein or a mannose receptor.

87. A compound, derivative, mixture, product, pharmaceutical composition, use or method of any of paragraphs 75 to 80, wherein the macromolecule is a glycosidase.

88. A compound, derivative, mixture, product, pharmaceutical composition, use or method of paragraph 87, wherein the glycosidase is a glucosidase.

89. A compound, derivative, mixture, product, pharmaceutical composition, use or method of paragraph 88, wherein the glucosidase is a β-glucosidase.

90. A compound, derivative, mixture, product, pharmaceutical composition, use or method of any of paragraphs 75 to 80, wherein the macromolecule is a growth factor.

91. A compound, derivative, mixture, product, pharmaceutical composition, use or method of paragraph 90, wherein the growth factor is a granulocyte colony stimulating factor (G-CSF), a granulocyte macrophage colony stimulating factor (GM-CSF), a nerve growth factor (NGF), a neurotrophin, a platelet-derived growth factor (PDGF), erythropoietin (EPO), thrombopoietin (TPO), myostatin (GDF-8), growth differentiation factor-9 (GDF9), a hepatocyte growth factor, or a fibroblast growth factor (FGF).

92. A compound, derivative, mixture, product, pharmaceutical composition, use or method of any of paragraphs 75 to 80, wherein the macromolecule is follistatin.

93. A compound, derivative, mixture, product, pharmaceutical composition, use or method of any of paragraphs 75 to 80, wherein the macromolecule is a phosphorylase.

94. A compound, derivative, mixture, product, pharmaceutical composition, use or method of paragraph 93, wherein the phosphorylase is glycogen, starch or maltodextrin phosphorylase.

95. A compound, derivative, mixture, product, pharmaceutical composition, use or method of paragraph 93 or 94, wherein the phosphorylase is hepatic.

96. A compound, derivative, mixture, product, pharmaceutical composition, use or method of any of paragraphs 93 to 95, wherein the phosphorylase is phosphorylase a or phosphorylase b.

97. A compound, derivative, mixture, product, pharmaceutical composition, use or method of any of paragraphs 75 to 80, wherein the macromolecule is a cytokine receptor or a cytokine.

98. A compound, derivative, mixture, product, pharmaceutical composition, use or method of paragraph 97, wherein the cytokine receptor or cytokine is a chemokine receptor or a chemokine.

99. A compound, derivative, mixture, product, pharmaceutical composition, use or method of paragraph 97 or 98, wherein the chemokine is MCP-1 or MCP-3.

100. A method of modifying the level of a cytokine in vivo, ex vivo or in vitro, said method comprising contacting a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, with a cell.

101. A method of testing for a modification in the level of a cytokine in vivo, ex vivo or in vitro, said method comprising contacting a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, with a cell.

102. A method of paragraph 100 or 101, wherein the cytokine is selected from GM-CSF, IL-1α, IL-1β, IL-2, IL-4, IL-5, IL-6, IL-7, IL-8, IL-10, IL-12, IL-13, IL-17, GCSF, VEGF, TNFα, RANTES, MCP-1 or IFNγ.

103. A method of paragraph 102, wherein the modification is a decrease in the level of GM-CSF, IL-1α, IL-1β, IL-2, IL-4, IL-5, IL-6, IL-10, IL-13, IL-17, GCSF, TNFα or IFNγ.

104. A method of paragraph 102, wherein the modification is an increase in the level of IL-7 or VEGF.

105. A method of any of paragraphs 100 to 104, wherein the method comprises contacting the compound or pharmaceutically acceptable salt thereof with a blood cell and/or a human cell.

106. A method of any of paragraphs 100 to 105, wherein the method is performed in vitro.

107. A method of any of paragraphs 100 to 105, wherein the method is performed in vivo.

108. A method of any of paragraphs 100 to 107, wherein the method is a method of treating or preventing a disease or condition.

109. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for the treatment or prevention of inflammation.

110. Use of a compound of any of paragraphs 1 to 58, a polysaccharide, oligosaccharide, peptide or protein derivative of paragraph 59, a mixture of any of paragraphs 60 to 62, or a product of paragraph 72, in the manufacture of a medicament for the treatment or prevention of inflammation.

111. A method of treating or preventing inflammation, comprising administering a therapeutically or prophylactically effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

112. A method of paragraph 108, wherein the disease or condition is inflammation.

113. A compound, derivative, mixture, product, pharmaceutical composition, use or method of any of paragraphs 109 to 112, wherein the inflammation is chronic inflammation.

114. A compound, derivative, mixture, product, pharmaceutical composition, use or method of any of paragraphs 109 to 112, wherein the inflammation occurs as a result of an inflammatory disorder, as a symptom of a non-inflammatory disorder, or is secondary to trauma, injury or autoimmunity.

115. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for the treatment or prevention of an inflammatory disorder, a proliferative disorder, an immune disorder, an angiogenesis-dependent disorder, a sensitivity disorder, an adverse endocrine reaction or a degenerative disorder.

116. Use of a compound of any of paragraphs 1 to 58, a polysaccharide, oligosaccharide, peptide or protein derivative of paragraph 59, a mixture of any of paragraphs 60 to 62, or a product of paragraph 72, in the manufacture of a medicament for the treatment or prevention of an inflammatory disorder, a proliferative disorder, an immune disorder, an angiogenesis-dependent disorder, a sensitivity disorder, an adverse endocrine reaction or a degenerative disorder.

117. A method of treating or preventing an inflammatory disorder, a proliferative disorder, an immune disorder, an angiogenesis-dependent disorder, a sensitivity disorder, an adverse endocrine reaction or a degenerative disorder, comprising administering a therapeutically or prophylactically effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

118. A method of paragraph 108, wherein the disease or condition is an inflammatory disorder, a proliferative disorder, an immune disorder, an angiogenesis-dependent disorder, a sensitivity disorder, an adverse endocrine reaction or a degenerative disorder.

119. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for the treatment or prevention of an inflammatory bowel disease, Crohn's disease, ulcerative colitis, collagenous colitis, lymphocytic colitis, ischaemic colitis, diversion colitis, infective colitis, indeterminate colitis, psoriasis, sarcoidosis, arthritis, rheumatoid arthritis, osteoarthritis, Behçet's syndrome, asthma, chronic obstructive pulmonary disease, atherosclerosis, cancer, inflammation, restenosis, papilloma, polyposis, fibrosis, proliferative bronchiolitis, tumour growth, proliferative periostitis, proliferative pulpitis, proliferative verrucous leukoplakia, macular degeneration, an autoimmune disorder, an immunodeficiency disorder, a transplant rejection disorder, a disorder related to a transplant, a disorder related to a renal, hepatic, corneal, cartilage, stem cell, chondrocyte, pulmonary, cardiac, vascular or myeloid transplant, HIV infection, AIDS, multiple sclerosis, systemic lupus erythematosus, septic shock, an allergy, a hyposensitivity, a hypersensitivity, hypersensitivity following the reactivation of herpes, diabetes, a degenerative disease or disorder, a degenerative joint disease, a neurodegenerative disease, an inflammatory degenerative disease, osteochondral defects, keratitis (including herpetic keratitis), herpes simplex or shingles.

120. Use of a compound of any of paragraph 1 to 58, a polysaccharide, oligosaccharide, peptide or protein derivative of paragraph 59, a mixture of any of paragraphs 60 to 62, or a product of paragraph 72, in the manufacture of a medicament for the treatment or prevention of an inflammatory bowel disease, Crohn's disease, ulcerative colitis, collagenous colitis, lymphocytic colitis, ischaemic colitis, diversion colitis, infective colitis, indeterminate colitis, psoriasis, sarcoidosis, arthritis, rheumatoid arthritis, osteoarthritis, Behçet's syndrome, asthma, chronic obstructive pulmonary disease, atherosclerosis, cancer, inflammation, restenosis, papilloma, polyposis, fibrosis, proliferative bronchiolitis, tumour growth, proliferative periostitis, proliferative pulpitis, proliferative verrucous leukoplakia, macular degeneration, an autoimmune disorder, an immunodeficiency disorder, a transplant rejection disorder, a disorder related to a transplant, a disorder related to a renal, hepatic, corneal, cartilage, stem cell, chondrocyte, pulmonary, cardiac, vascular or myeloid transplant, HIV infection, AIDS, multiple sclerosis, systemic lupus erythematosus, septic shock, an allergy, a hyposensitivity, a hypersensitivity, hypersensitivity following the reactivation of herpes, diabetes, a degenerative disease or disorder, a degenerative joint disease, a neurodegenerative disease, an inflammatory degenerative disease, osteochondral defects, keratitis (including herpetic keratitis), herpes simplex or shingles.

121. A method of treating or preventing an inflammatory bowel disease, Crohn's disease, ulcerative colitis, collagenous colitis, lymphocytic colitis, ischaemic colitis, diversion colitis, infective colitis, indeterminate colitis, psoriasis, sarcoidosis, arthritis, rheumatoid arthritis, osteoarthritis, Behçet's syndrome, asthma, chronic obstructive pulmonary disease, atherosclerosis, cancer, inflammation, restenosis, papilloma, polyposis, fibrosis, proliferative bronchiolitis, tumour growth, proliferative periostitis, proliferative pulpitis, proliferative verrucous leukoplakia, macular degeneration, an autoimmune disorder, an immunodeficiency disorder, a transplant rejection disorder, a disorder related to a transplant, a disorder related to a renal, hepatic, corneal, cartilage, stem cell, chondrocyte, pulmonary, cardiac, vascular or myeloid transplant, HIV infection, AIDS, multiple sclerosis, systemic lupus erythematosus, septic shock, an allergy, a hyposensitivity, a hypersensitivity, hypersensitivity following the reactivation of herpes, diabetes, a degenerative disease or disorder, a degenerative joint disease, a neurodegenerative disease, an inflammatory degenerative disease, osteochondral defects, keratitis (including herpetic keratitis), herpes simplex or shingles, comprising administering a therapeutically or prophylactically effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

122. A method of paragraph 108, wherein the disease or condition is selected from an inflammatory bowel disease, Crohn's disease, ulcerative colitis, collagenous colitis, lymphocytic colitis, ischaemic colitis, diversion colitis, infective colitis, indeterminate colitis, psoriasis, sarcoidosis, arthritis, rheumatoid arthritis, osteoarthritis, Behçet's syndrome, asthma, chronic obstructive pulmonary disease, atherosclerosis, cancer, inflammation, restenosis, papilloma, polyposis, fibrosis, proliferative bronchiolitis, tumour growth, proliferative periostitis, proliferative pulpitis, proliferative verrucous leukoplakia, macular degeneration, an autoimmune disorder, an immunodeficiency disorder, a transplant rejection disorder, a disorder related to a transplant, a disorder related to a renal, hepatic, corneal, cartilage, stem cell, chondrocyte, pulmonary, cardiac, vascular or myeloid transplant, HIV infection, AIDS, multiple sclerosis, systemic lupus erythematosus, septic shock, an allergy, a hyposensitivity, a hypersensitivity, hypersensitivity following the reactivation of herpes, diabetes, a degenerative disease or disorder, a degenerative joint disease, a neurodegenerative disease, an inflammatory degenerative disease, osteochondral defects, keratitis (including herpetic keratitis), herpes simplex or shingles.

123. A compound, derivative, mixture, product, pharmaceutical composition, use or method of any of paragraphs 119 to 122, wherein the psoriasis is plaque psoriasis, pustular psoriasis, guttate psoriasis, psoriatic arthritis, inverse psoriasis, or erythrodermic psoriasis.

124. A compound, derivative, mixture, product, pharmaceutical composition, use or method of any of paragraphs 119 to 122, wherein the diabetes is diabetes mellitus.

125. A compound, derivative, mixture, product, pharmaceutical composition, use or method of paragraph 124, wherein the diabetes is type 1, type 2, gestational, malnutrition related, or impaired glucose tolerance related.

126. A compound, derivative, mixture, product, pharmaceutical composition, use or method of any of paragraphs 119 to 122, wherein the diabetes is diabetes insipidus.

127. A compound, derivative, mixture, product, pharmaceutical composition, use or method of paragraph 126, wherein the diabetes is central, nephrogenic, dipsogenic, or gestational.

128. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for the treatment or prevention of an autoimmune disease.

129. Use of a compound of any of paragraphs 1 to 58, a polysaccharide, oligosaccharide, peptide or protein derivative of paragraph 59, a mixture of any of paragraphs 60 to 62, or a product of paragraph 72, in the manufacture of a medicament for the treatment or prevention of an autoimmune disease.

130. A method of treating or preventing an autoimmune disease, comprising administering a therapeutically or prophylactically effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

131. A method of paragraph 108, wherein the disease or condition is an autoimmune disease.

132. A compound, derivative, mixture, product, pharmaceutical composition, use or method of any of paragraphs 128 to 131, wherein the autoimmune disease is selected from acute disseminated encephalitis, Addison's disease, ankylosing spondylitis, antiphospholipid antibody syndrome (APS), aplastic anemia, autoimmune adrenalitis, autoimmune hepatitis, autoimmune oophoritis, autoimmune polyglandular failure, autoimmune thyroiditis, Coeliac disease, Crohn's disease, diabetes mellitus, Goodpasture's syndrome, Graves' disease, Guillain-Barré syndrome (GBS), Hashimoto's disease, idiopathic thrombocytopenic purpura, Kawasaki's disease, lupus erythematosus, multiple sclerosis, myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis, Reiter's syndrome, Sjögren's syndrome, a systemic connective tissue disorder, Takayasu's arteritis, temporal arteritis, warm autoimmune hemolytic anemia, Wegener's granulomatosis, alopecia universalis, Behçcet's disease, Chagas' disease, chronic fatigue syndrome, dysautonomia, endometriosis, hidradenitis suppurativa, interstitial cystitis, Lyme disease, neuromyotonia, psoriasis, sarcoidosis, schizophrenia, scleroderma, ulcerative colitis, vitiligo or vulvodynia.

133. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for the aid of wound healing.

134. Use of a compound of any of paragraphs 1 to 58, a polysaccharide, oligosaccharide, peptide or protein derivative of paragraph 59, a mixture of any of paragraphs 60 to 62, or a product of paragraph 72, in the manufacture of a medicament for the aid of wound healing.

135. A method of aiding wound healing, comprising administering a therapeutically effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

136. A method of paragraph 108, wherein the disease or condition is a wound.

137. A compound, derivative, mixture, product, pharmaceutical composition, use or method of any of paragraphs 133 to 136, wherein the wound is chronic, and/or has arisen from trauma, decubitis, cosmetic surgery, surgical therapy, organ and tissue transplantation, insect bites or burns.

138. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for the treatment or prevention of depression.

139. Use of a compound of any of paragraphs 1 to 58, a polysaccharide, oligosaccharide, peptide or protein derivative of paragraph 59, a mixture of any of paragraphs 60 to 62, or a product of 72, in the manufacture of a medicament for the treatment or prevention of depression.

140. A method of treating or preventing depression, comprising administering a therapeutically or prophylactically effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

141. A method of paragraph 108, wherein the disease or condition is depression.

142. A compound, derivative, mixture, product, pharmaceutical composition, use or method of any of paragraphs 138 to 141, wherein the depression is a major depressive disorder, catatonic features specification, melancholic features specification, atypical features specification, psychotic features specification, dysthymia, bipolar I disorder, bipolar II disorder, or post-natal depression.

143. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for aiding cartilage repair or cartilage regeneration.

144. Use of a compound of any of paragraphs 1 to 58, a polysaccharide, oligosaccharide, peptide or protein derivative of paragraph 59 a mixture of any of paragraphs 60 to 62, or a product of paragraph 72, in the manufacture of a medicament for aiding cartilage repair or cartilage regeneration.

145. A method of aiding cartilage repair or cartilage regeneration, comprising administering a therapeutically effective amount of a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a patient in need thereof.

146. A method of any of paragraphs 100 to 108, wherein the method is a method of aiding cartilage repair or cartilage regeneration.

147. A compound, derivative, mixture, product, pharmaceutical composition, use or method of any of paragraphs 74 to 146, wherein the patient to be treated is a mammal.

148. A compound, derivative, mixture, product, pharmaceutical composition, use or method of paragraph 147, wherein the mammal is a human.

149. A compound, derivative, mixture, product, pharmaceutical composition, use or method of paragraph 147, wherein the mammal is a non-human.

150. A compound, derivative, mixture, product, pharmaceutical composition, use or method of paragraph 149 when dependent on paragraph 101, wherein the non-human subject is mutilated or sacrificed as a result of the test.

151. A compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, for the performance of a laboratory test.

152. Use of a compound of any of paragraphs 1 to 58, a polysaccharide, oligosaccharide, peptide or protein derivative of paragraph 59, a mixture of any of paragraphs 60 to 62, or a product of paragraph 72, in the manufacture of a diagnostic agent for the performance of a laboratory test.

153. A method of performing a laboratory test, comprising administering a compound of any of paragraphs 1 to 58, a polysaccharide, oligosaccharide, peptide or protein derivative of paragraph 59, a mixture of any of paragraphs 60 to 62, a product of paragraph 72, or a pharmaceutical composition of paragraph 73, to a subject to be tested.

154. A compound, derivative, mixture, product, pharmaceutical composition, use or method of any of paragraphs 151 to 153, wherein the testing occurs in vitro, ex vitro or in vivo.

155. A compound, derivative, mixture, product, pharmaceutical composition, use or method of any of paragraphs 151 to 154, wherein the subject to be tested is a mammal.

156. A compound, derivative, mixture, product, pharmaceutical composition, use or method of paragraph 155, wherein the mammal is a human.

157. A compound, derivative, mixture, product, pharmaceutical composition, use or method of paragraph 155, wherein the mammal is a non-human.

158. A compound, derivative, mixture, product, pharmaceutical composition, use or method of paragraph 157, wherein the non-human subject is mutilated or sacrificed as a result of the test.

SYNTHETIC EXAMPLES

Theoretical preparation of [1-N-octyl-1-N-decanoyl-1-amino-1-deoxy-6-potassium sulphonatomuramyl]-D-isoglutamyl-(N-formyl or N-acetyl)-alanine

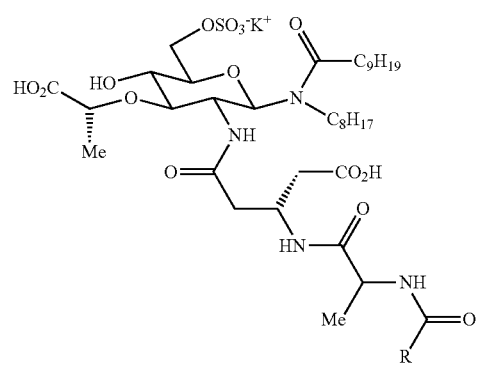

R = H or Me

A solution of 130 mg of [1-N-octyl-1-N-decanoyl-1-amino-1-deoxymuramyl]-D-isoglutamyl-(N-formyl or N-acetyl)-alanine in 3 ml of pyridine is treated with sulphur trioxide pyridine complex. The mixture is kept at ambient temperature for 12 hours and then the excess solvent is decanted from the oily residue. This residue is dissolved in ice water and the pH is adjusted to pH 9 with KOH solution. Addition of methanol precipitates the product.

Theoretical preparation of three- to four-fold sulphated 1-benzamido-1-deoxy-glucose

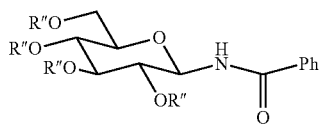

0 to 1 x R" = H
3 to 4 x R" = SO$_3^-$K$^+$

A solution of 1.8 g of 1-amino-1-deoxyglucose and 600 mg of potassium carbonate in water is treated with 1.5 g of benzoyl chloride under cooling with ice. After completion of the reaction, 280 mg of N-benzoyl-1-amino-1-deoxyglucose is dissolved in 5 ml of pyridine and 10 ml of DMF, and 950 mg of sulphur trioxide pyridine complex is added. The mixture is heated to 50° C. for 7 hours under stirring and then allowed to cool to ambient temperature. The oily residue is separated by decanting the supernatant and then dissolved in ice water. The mixture is neutralized with cold KOH solution under external cooling. The precipitation of the product is completed by adding methanol and the product is collected by filtration.

N-Acetyl-β,β-diglucosylamine

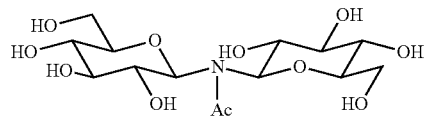 [SMILES: CC(=O)N(C1OC(CO)C(O)C(O)C1O)C1OC(CO)C(O)C(O)C1O]

A suspension of 1.7 g of O-octaacetyl-β,β-diglucosylamine in 10 ml of acetic anhydride was treated with 1.2 g of freshly fused and powdered zinc chloride. After 3 hours, the clear solution was poured onto ice and 0.5 ml of pyridine was added. Rapid stirring produced a white precipitate that was collected by filtration and washed with water. The material was used without further purification. The material was suspended in 4 ml of a solution of ammonia in methanol (7 M) and agitated overnight. Evaporation yielded a white solid that showed uniformity in t.l.c. (methanol). The crude product was used without further purification.

Three- to five fold sulphated
N-acetyl-β,β-diglucosylamine

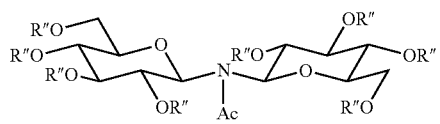

3 to 5 x R" = H
3 to 5 x R" = SO$_3^-$K$^+$

To a suspension of 1.66 g of sulphur trioxide pyridine complex in 10 ml of dry pyridine and 2 ml of dry DMAc was added, at 60° C., 0.5 g of N-acetyl-β,β-diglucosylamine. The mixture was stirred rapidly at a temperature of 55-65° C. for 4 hours. After cooling the supernatant was decanted and the residue was dissolved in a small amount of ice water. The solution was treated with a solution of 400 mg of KOH and 300 mg of potassium acetate in 4 ml of water. Precipitation of a white solid occurred and was completed by addition of methanol. The white solid was filtered off and recrystallised from a small quantity of water to give the multi-potassium salt. MS analysis indicated the product to consist mainly of three- to five-fold sulphated material.

Four- to six-fold sulphated
N-acetyl-β,β-diglucosylamine

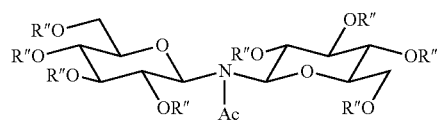

2 to 4 x R" = H
4 to 6 x R" = SO$_3^-$K$^+$

To a suspension of 1.66 g of sulphur trioxide pyridine complex in 10 ml of dry pyridine and 2 ml of dry DMAc was added, at 60° C., 0.5 g of N-acetyl-β,β-diglucosylamine. The mixture was stirred rapidly at a temperature of 55-65° C. for 6 hours. After cooling the supernatant was decanted and the residue dissolved in a small amount of ice water. The solution was treated with a solution of 400 mg of KOH and 300 mg of potassium acetate in 4 ml of water. Precipitation of a white solid occurred and was completed by addition of methanol. The white solid was filtered off and recrystallised from a small quantity of water. MS analysis showed the product to consist mainly of four- to six-fold sulphated material.

Five- to seven fold sulphated
N-acetyl-β,β-diglucosylamine

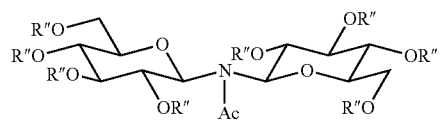

1 to 3 x R" = H
5 to 7 x R" = SO$_3^-$K$^+$

To a suspension of 1.66 g of sulphur trioxide pyridine complex in 10 ml of dry pyridine and 2 ml of dry DMAc was added, at 60° C., 0.5 g of N-acetyl-β,β-diglucosylamine. The mixture was stirred rapidly at a temperature of 60-70° C. for 8 hours until the colour turned slightly brownish. After cooling the supernatant was decanted and the residue dissolved in a small amount of ice water. The solution was treated with a solution of 400 mg of KOH and 300 mg of potassium acetate in 4 ml of water. Precipitation of a white solid occurred and was completed by addition of methanol. The white solid was filtered off and recrystallised from a small quantity of water to give the multi-potassium salt. MS analysis showed the product to consist mainly of five- to seven-fold sulphated material.

Theoretical preparation of four- to seven-fold sulphated N-ethyl-β,β-diglucosylamine

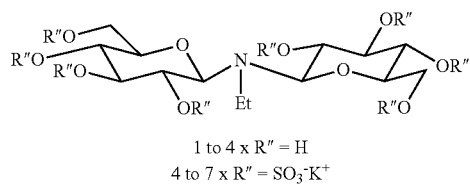

1 to 4 x R" = H
4 to 7 x R" = SO₃⁻K⁺

To as suspension of 1.7 g of sulphur trioxide pyridine complex in 6 ml of dry pyridine is added 5.5 g of N-ethyl-β,β-diglucosylamine. The mixture is stirred at 60° C. for 12 hours. Stirring is then stopped and, after cooling, the supernatant liquid is decanted from the reddish brown oil. The residual oil is dissolved in ice water and neutralised with concentrated KOH solution while applying external cooling. Addition of methanol completes the precipitation of the product, which is recrystallised from a small quantity of water to give the multi-potassium salt.

BIOLOGICAL EXAMPLES

Safety/Toxicity Studies

N-Acetyl-β,β-diglucosylamine oligosulphate 850 (i.e. the multi-potassium salt form of N-acetyl-β,β-diglucosylamine sulphated so that the average molecular weight is approximately 850) was administered to 12 mice orally for 35 days at a dosage of 100 mg/kg/day. No adverse events were observed.

The above experiment was repeated using N-acetyl-β,β-diglucosylamine oligosulphate 1000. Again, no adverse events were observed.

Collagen-Induced Arthritis
Preparation of Collagen:

Chick sternal collagen II was dissolved in 0.01M acetic acid by gentle stirring overnight at 4° C. at a concentration of 2 mg/ml. This was emulsified with ice-cold Freund's complete adjuvant (FCA: 2 mg/ml *mycobacterium tuberculosis* in Freund's incomplete adjuvant) by addition of small volumes of the collagen II solution to the FCA and mixing to a ratio of 1:1.

Induction of Arthritis:

Mice were lightly anaesthetised with halothane. The base of the tail was shaved and 100 μl collagen II/FCA emulsion (100 μg collagen II) was injected intradermally to the left hand side of this site. 21 days after initial sensitisation, collagen II was dissolved in acetic acid as above, emulsified 1:1 in Freund's incomplete adjuvant and 100 μl was injected into the base of the tail on the right hand side of the tail base. This day was given as day 0.

Dosing:

The non-control mice were dosed with either N-acetyl-β,β-diglucosylamine oligosulphate 850 or N-acetyl-β,β-diglucosylamine oligosulphate 1000 orally at concentrations of 118 μM/kg/day and 100 μM/kg/day respectively (100 mg dissolved in 10 ml water) once a day on days 0-35. Water was used as the control.

Assessment:

Mice were individually marked and examined every other day from the time of the day of boost (day 0). The degree of arthritis was scored using an arbitrary scale on predetermined days. The animals' paws were examined and any inflammation was noted. Every inflamed main digit scored one, inflammation of the front paw scored one, inflammation of the hind paw scored one, and involvement of the ankle scored one. Thus a maximal score for each animal was 22. Body weights were also recorded.

Figure 2:
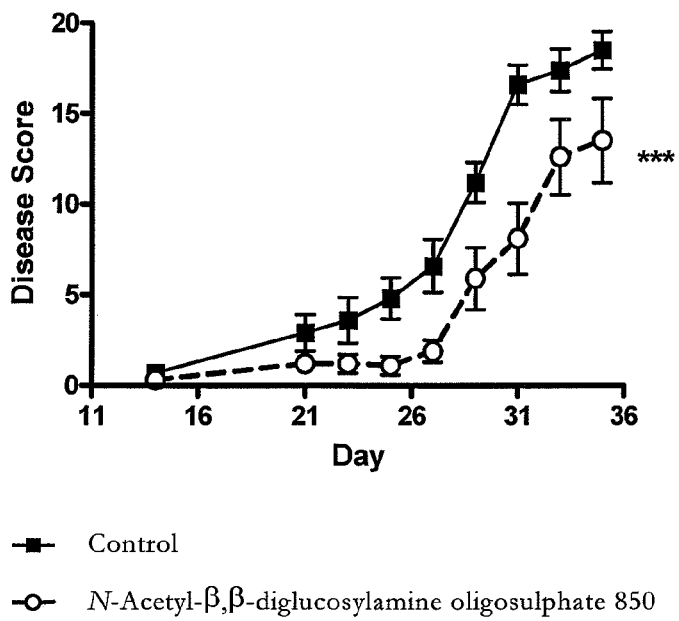
FIG. 2 shows the inhibition of mouse collagen arthritis by N-acetyl-β,β-diglucosylamine oligosulphate 850 administered orally at a concentration of 118 μM/kg on days 0-35, n=10, mean±s.e.m., ***=p<0.001, 2-way ANOVA.
Figure 3:
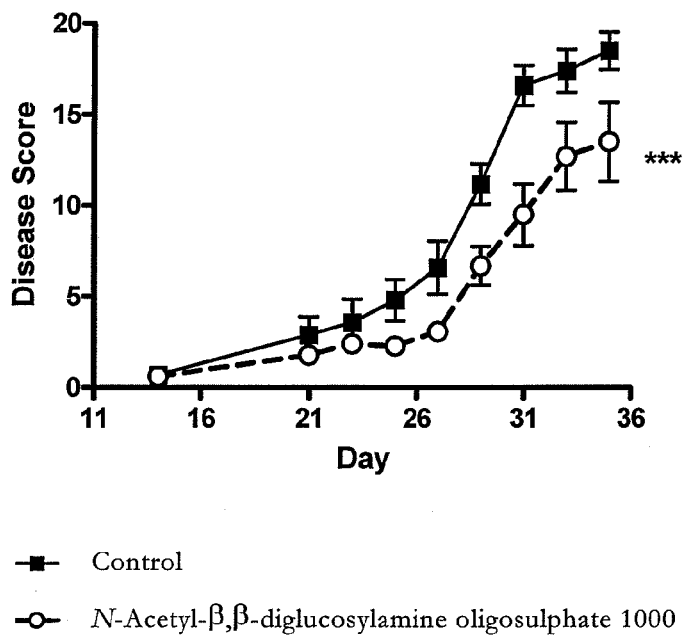
FIG. 3 shows the inhibition of mouse collagen arthritis by N-acetyl-β,β-diglucosylamine oligosulphate 1000 administered orally at a concentration of 100 μM/kg on days 0-35, n=10, mean±s.e.m., ***=p<0.001, 2-way ANOVA.

Results:

The results for N-acetyl-β,β-diglucosylamine oligosulphate 850 and 1000 respectively are illustrated in FIGS. 2 and 3. It can be seen that both compounds prevented the development of arthritic disease in these mice as assessed by clinical scoring of the disease. Mice receiving the drugs did not exhibit any alteration of body mass when compared to the vehicle control.

Antigen-Induced Arthritis

Figure 4:
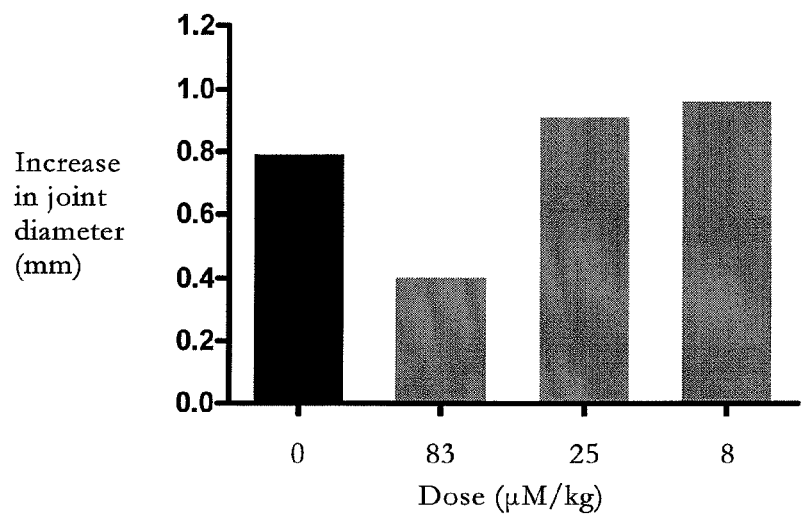
FIG. 4 shows the inhibition of mouse mBSA antigen induced arthritis after the oral administration of N-acetyl-β,β-diglucosylamine oligosulphate 1200 at concentrations of 83 μM/kg, 25 μM/kg and 8 μM/kg.

C57bl/6 mice were sensitised to methylated bovine serum albumin in Freund's complete adjuvant. 14 days later they were challenged with the intra-articular injection of mBSA in one stifle joint and saline in the other. The non-control mice were dosed orally, 1 hour prior to the challenge, with N-acetyl-β,β-diglucosylamine oligosulphate 1200 at concentrations of 83 μM/kg, 25 μM/kg and 8 μM/kg. Joint inflammation was assessed as an increase in diameter, measured with calipers. The results are shown in FIG. 4. It can be seen from this that an oral prophylactic dose of 83 μM/kg N-acetyl-β,β-diglucosylamine oligosulphate 1200 significantly reduces joint inflammation.

TNF Synthesis in Lps Stimulated Human Differentiated Macrophage Cells

Figure 5:
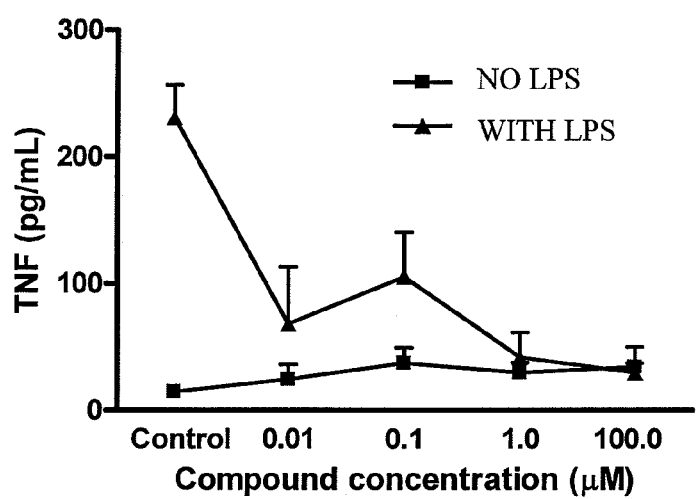
FIG. 5 shows the inhibition of TNF synthesis in lipopolysaccharide (lps) stimulated human differentiated macrophage cells, through their incubation with N-acetyl-β,β-diglucosylamine oligosulphate 1200.
Figure 6:
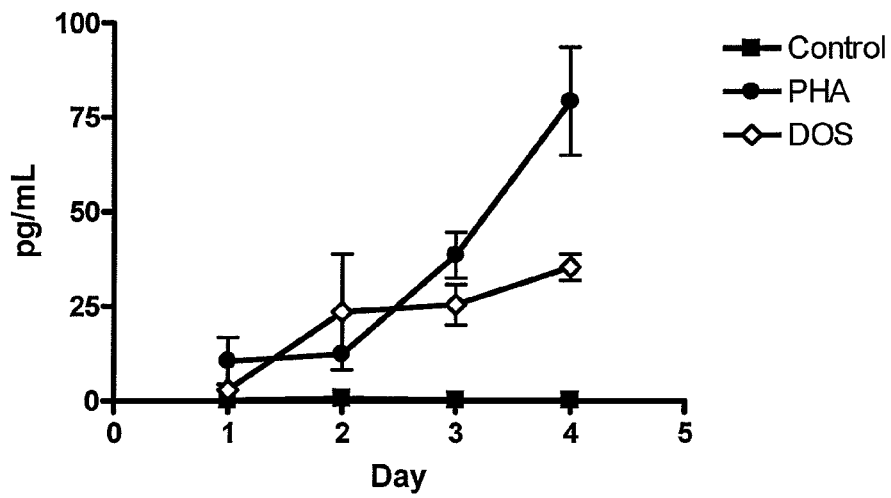
FIG. 6 shows the inhibition of PHA stimulated IL-1α synthesis in human whole blood by 0.01 μM N-acetyl-β,β-diglucosylamine octasulphate (DOS).
Figure 7:
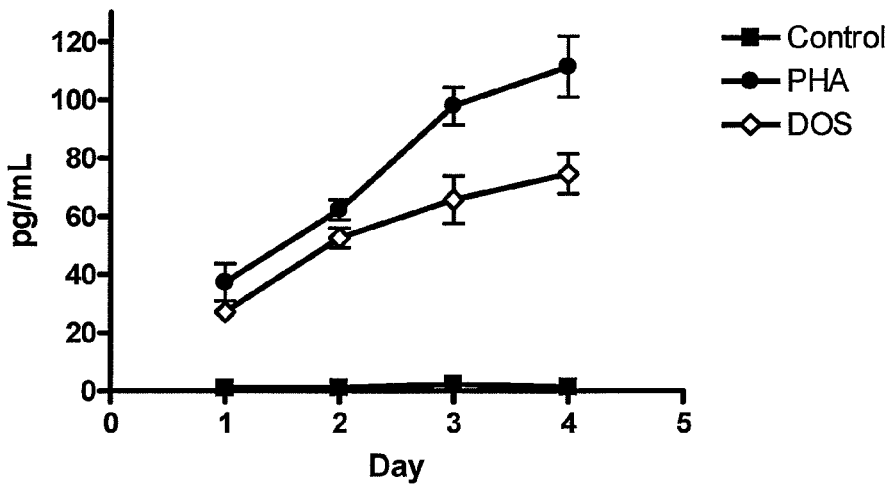
FIG. 7 shows the inhibition of PHA stimulated IL-1β synthesis in human whole blood by 0.01 μM N-acetyl-β,β-diglucosylamine octasulphate (DOS).
Figure 8:
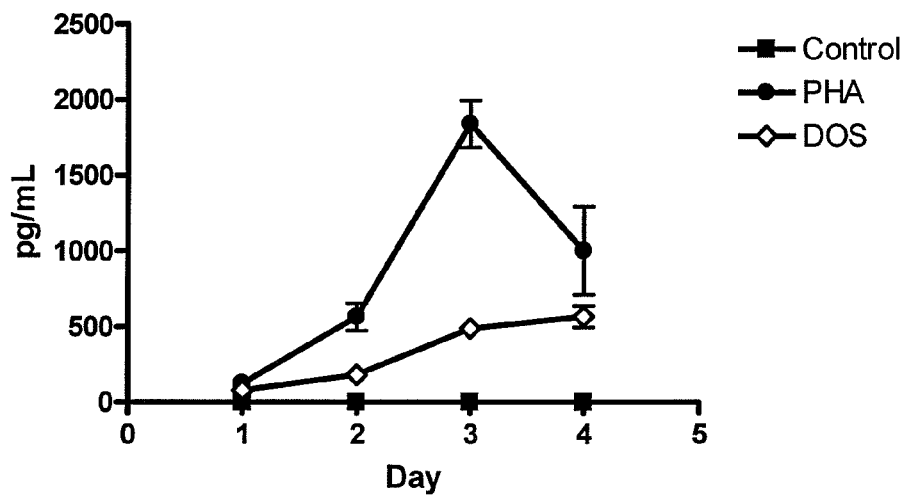
FIG. 8 shows the inhibition of PHA stimulated IL-2 synthesis in human whole blood by 0.01 μM N-acetyl-β,β-diglucosylamine octasulphate (DOS).
Figure 9:
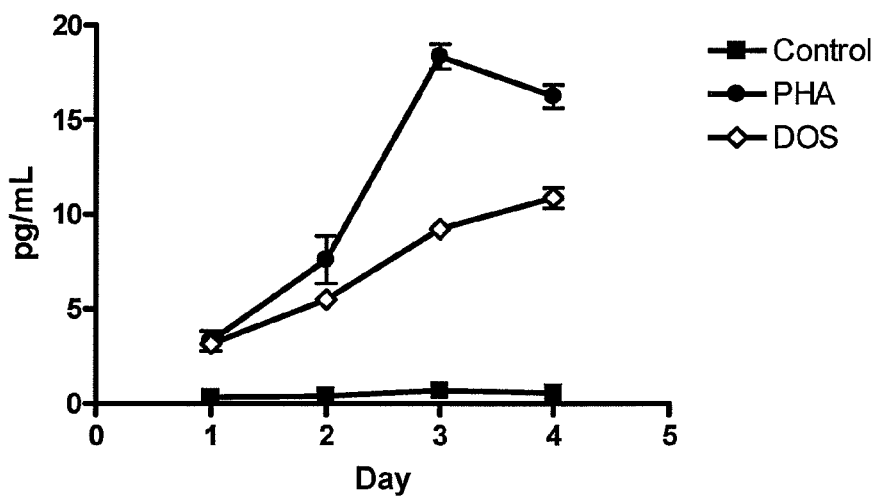
FIG. 9 shows the inhibition of PHA stimulated IL-4 synthesis in human whole blood by 0.01 μM N-acetyl-β,β-diglucosylamine octasulphate (DOS).
Figure 10:
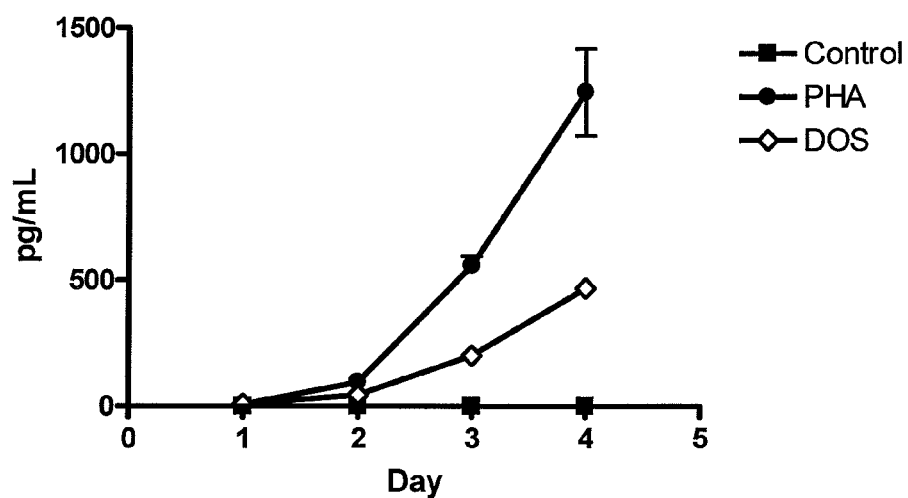
FIG. 10 shows the inhibition of PHA stimulated IL-5 synthesis in human whole blood by 0.01 μM N-acetyl-β,β-diglucosylamine octasulphate (DOS).
Figure 11:
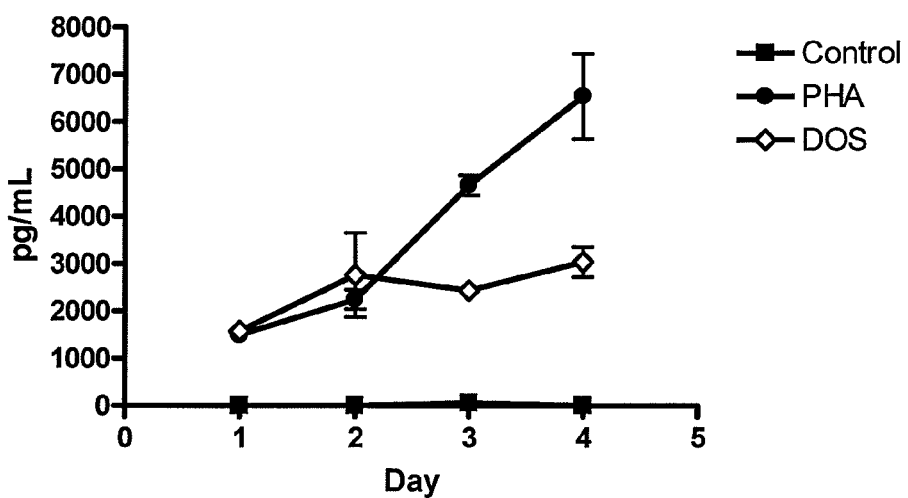
FIG. 11 shows the inhibition of PHA stimulated IL-6 synthesis in human whole blood by 0.01 μM N-acetyl-β,β-diglucosylamine octasulphate (DOS).
Figure 12:
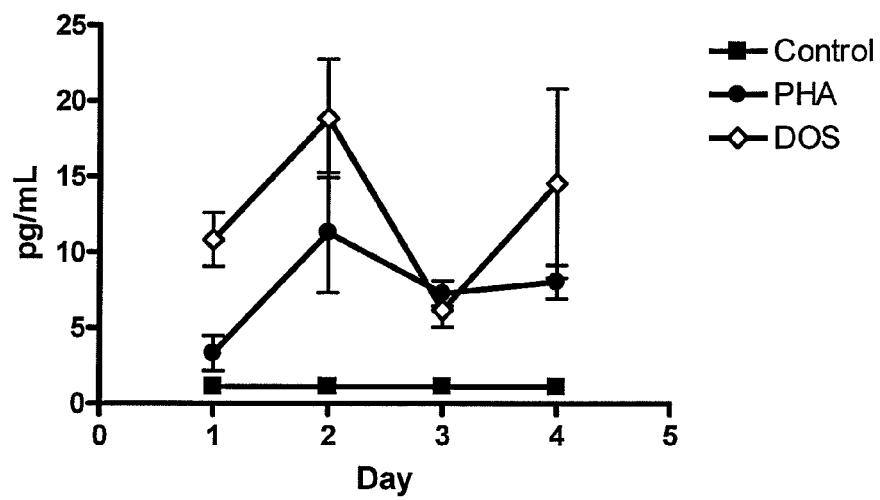
FIG. 12 shows the further stimulation of PHA stimulated IL-7 synthesis in human whole blood by 0.01 μM N-acetyl-β,β-diglucosylamine octasulphate (DOS).
Figure 13:
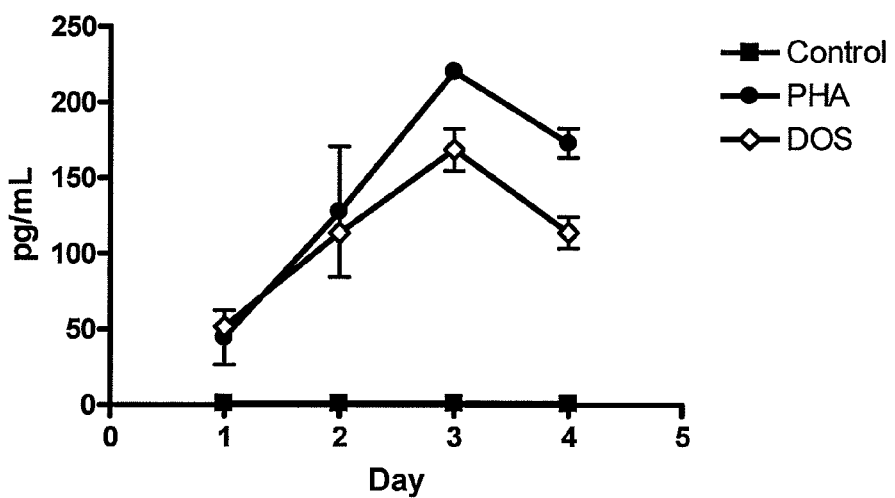
FIG. 13 shows the effect on PHA stimulated IL-10 synthesis in human whole blood by 0.01 μM N-acetyl-β,β-diglucosylamine octasulphate (DOS).
Figure 14:
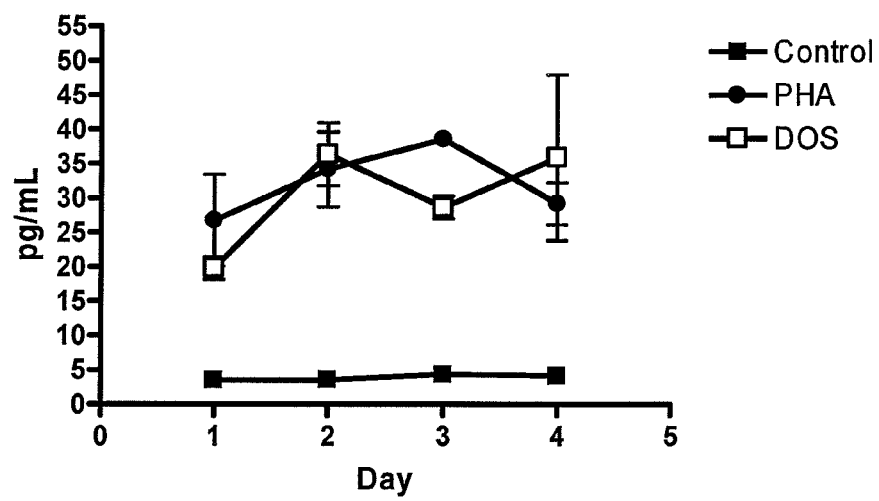
FIG. 14 shows the effect on PHA stimulated IL-12 synthesis in human whole blood by 0.01 μM N-acetyl-β,β-diglucosylamine octasulphate (DOS).
Figure 15:
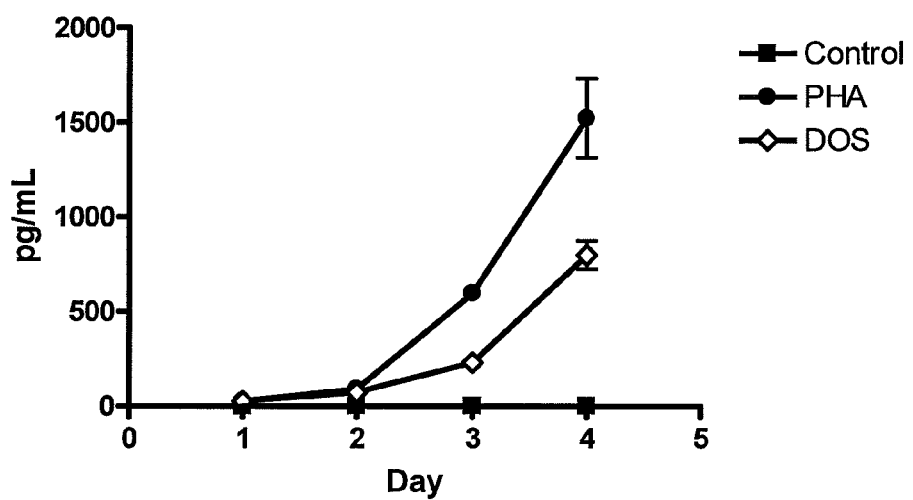
FIG. 15 shows the inhibition of PHA stimulated IL-13 synthesis in human whole blood by 0.01 μM N-acetyl-β,β-diglucosylamine octasulphate (DOS).
Figure 16:
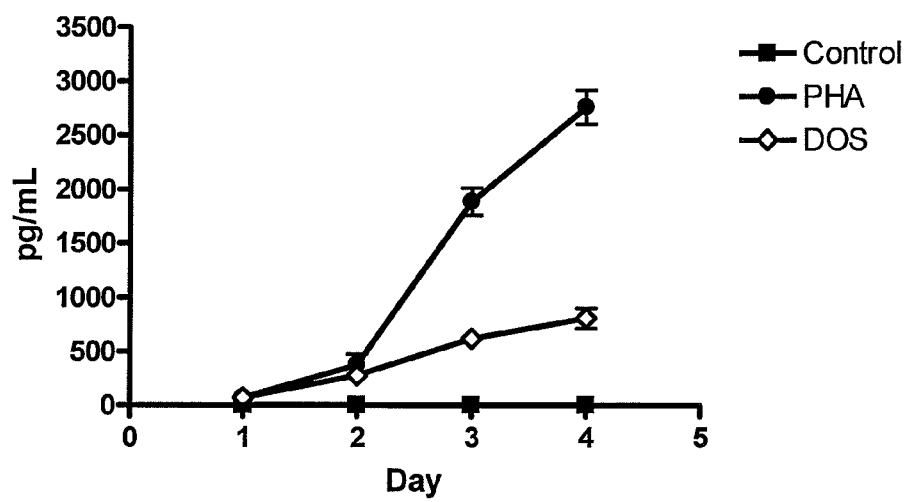
FIG. 16 shows the inhibition of PHA stimulated IL-17 synthesis in human whole blood by 0.01 μM N-acetyl-β,β-diglucosylamine octasulphate (DOS).
Figure 17:
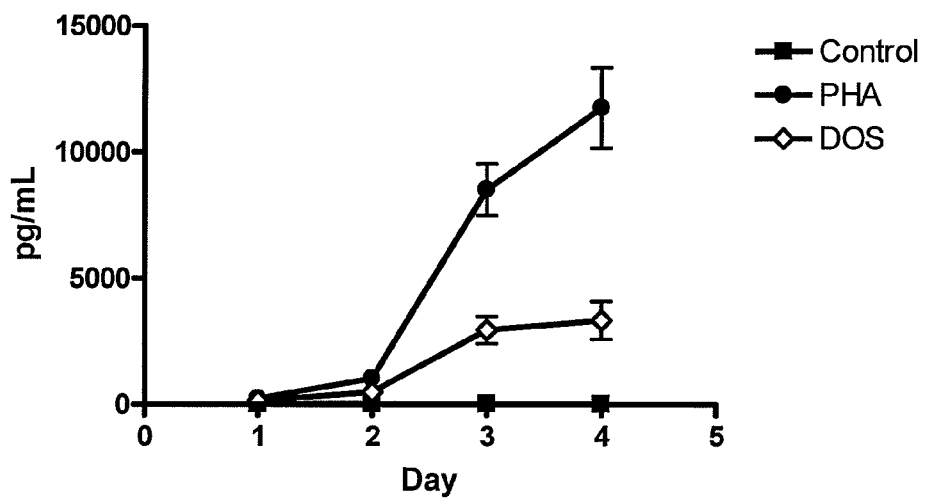
FIG. 17 shows the inhibition of PHA stimulated IFNγ synthesis in human whole blood by 0.01 μM N-acetyl-β,β-diglucosylamine octasulphate (DOS).
Figure 18:
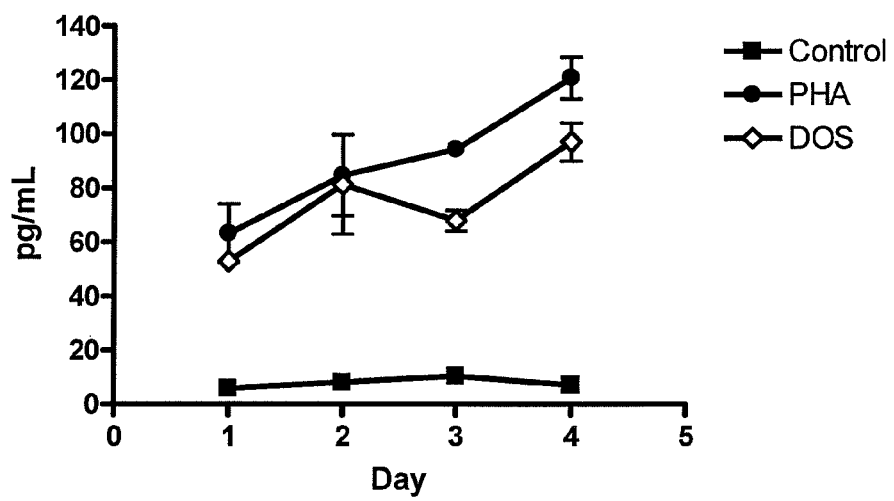
FIG. 18 shows the inhibition of PHA stimulated GCSF synthesis in human whole blood by 0.01 μM N-acetyl-β,β-diglucosylamine octasulphate (DOS).
Figure 19:
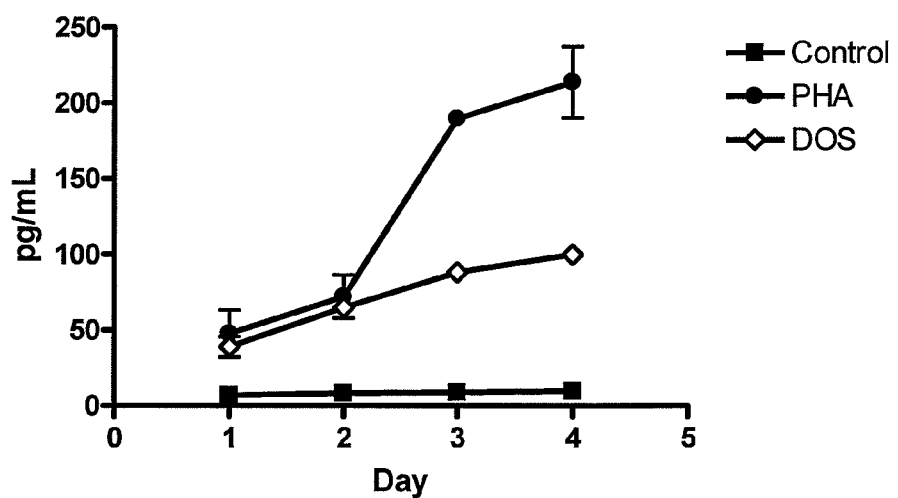
FIG. 19 shows the inhibition of PHA stimulated GM-CSF synthesis in human whole blood by 0.01 μM N-acetyl-β,β-diglucosylamine octasulphate (DOS).
Figure 20:
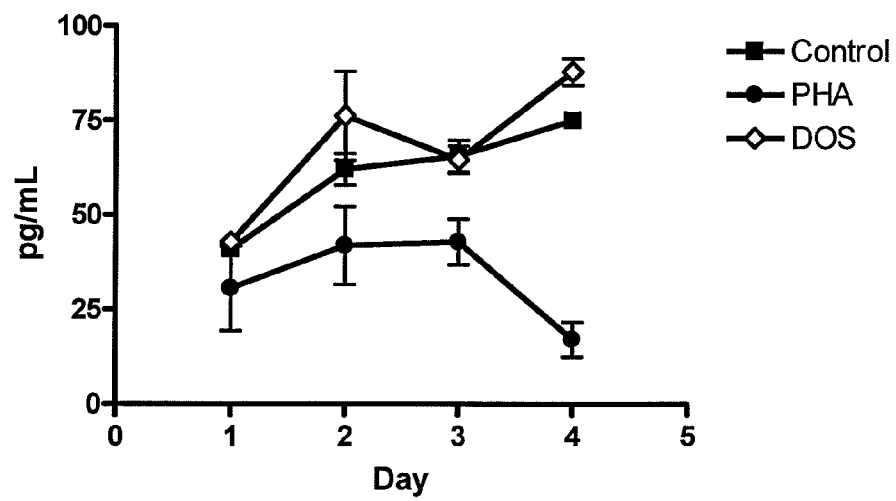
FIG. 20 shows the 0.01 μM N-acetyl-β,β-diglucosylamine octasulphate (DOS) induced stimulation of VEGF synthesis in human whole blood in which the VEGF synthesis has been inhibited by PHA.
Figure 21:
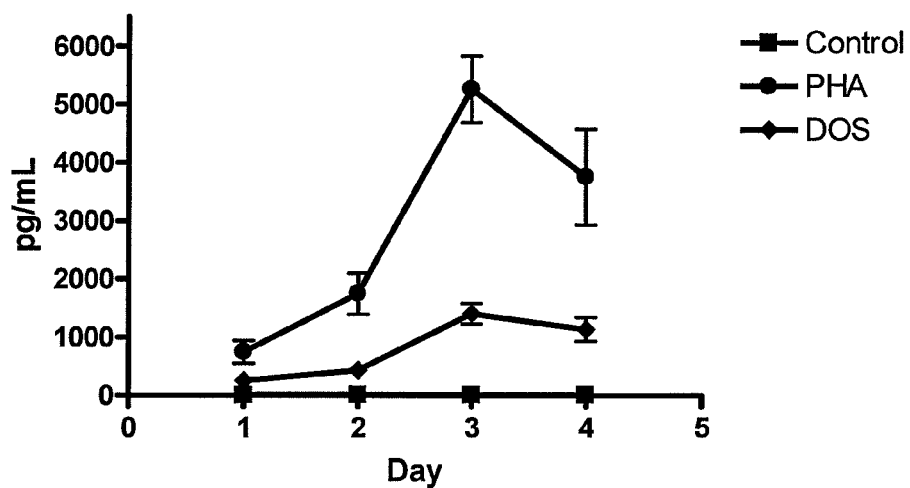
FIG. 21 shows the inhibition of PHA stimulated TNFα synthesis in human whole blood by 0.01 μM N-acetyl-β,β-diglucosylamine octasulphate (DOS).

U937 cells were differentiated in phorbol mysterate acetate into human macrophages. TNF synthesis was induced by lipopolysaccharide (lps) for 8 hours in the absence or presence of N-acetyl-β,β-diglucosylamine oligosulphate 1200 at concentrations of 0.01, 0.1, 1.0, or 100 μM. The inhibition of TNF synthesis was assayed by ELISA. The results are shown in FIG. 5. It can be seen that N-acetyl-β,β-diglucosylamine oligosulphate 1200 effectively inhibits TNF synthesis in lps stimulated human differentiated macrophage cells.

PHA Stimulated Human Whole Blood Cytokine Synthesis
Whole Blood Culture:

Blood was taken from a healthy young male volunteer, into heparin Vacutainers®. Whole-blood was diluted to give a final concentration of ¹/₁₀ in culture medium (CM). CM consisted of RPMI 1640 with L-glutamine, penicillin and streptomycin. PHA (phytohaemagglutinin) solution and N-acetyl-β,β-diglucosylamine octasulphate (DOS) and PHA solution were added to non-control samples. Final drug concentrations tested were 100 μM, 1 μM, 0.1 μM and 0.01 μM. All samples were tested in triplicate.

Reagents were placed in four sets of 24-well (6×4) flat-bottomed plates (Corning US) and incubated for 1, 2, 3 and 4 days respectively (incubator conditions: 37° C., humid and 5% CO₂). After each day, starting at day 1, a set of plates was centrifuged (at 400 rpm for 6 minutes) and supernatant placed in individual 1.5 ml eppendorf tubes and stored at −80° C.

ELISA:

The protocol of Lagrelius et al. was followed (*Cytokine,* 2006, 33, pp. 156-165). The culture supernatants were analysed once for concentrations of IL-1α, IL-1β, IL-2, IL-4, IL-5, IL-6, IL-7, IL-10, IL-12, IL-13, IL-17, IFNγ, GCSF, GM-CSF, MCP-1, RANTES, VEGF and TNFα. The cytokines were measured simultaneously using a Bio-Plex assay. This assay employs a bead-based sandwich immunoassay technique. A monoclonal antibody specific for each cytokine of interest is coupled onto a particular set of beads with a known internal fluorescence, and several combinations of cytokine antibody coated beads can be included and thus multiple cytokines are measured simultaneously. The assay was performed according to the manufacturer's instructions using a Bio-Plex kit (Bio-Rad Laboratories). Briefly, 50 ml of standard or test sample along with 50 ml of mixed beads were added into the wells of a pre-wet 96-well microtitre plate. After 1 hour incubation and washing, 25 ml of detection antibody mixture was added and the samples were incubated for 30 minutes and then washed. Finally, 50 ml of streptavidin-PE was added and after 10 minutes incubation and washing, the beads were resuspended in 125 ml of assay buffer. The beads were analysed employing a Bio-Plex suspension array system (Bio-Rad Laboratories) and the Bio-Plex manager software (version 3.0). A minimum of 100 beads per region were analysed. A curve fit was applied to each standard curve according to the manufacturer's manual and sample concentrations were interpolated from the standard curves. The limit of quantification of cytokine detection using this method was 2 pg/ml for IL-5, IL-10, IL-12 and IL-17, 2.8 pg/ml for IL-2, IL-4, IL-6, IL-13 and TNFα, 2.32 pg/ml for IFNγ, and 8.32 pg/ml for GM-CSF.

Results:

PHA increased the levels of all cytokines except VEGF which was reduced. IL-8, MCP-1 and RANTES were outside the range of the assay. The action of 0.01 µM N-acetyl-β,β-diglucosylamine octasulphate (DOS) on PHA stimulated synthesis of IL-1α, IL-1β, IL-2, IL-4, IL-5, IL-6, IL-7, IL-10, IL-12, IL-13, IL-17, IFNγ, GCSF, GM-CSF, VEGF and TNFα is shown in FIGS. 6 to 21 respectively.

It can be seen that N-acetyl-β,β-diglucosylamine octasulphate (DOS) inhibits the PHA stimulated synthesis of IL-1α, IL-1β, IL-2, IL-4, IL-5, IL-6, IL-10, IL-13, IL-17, IFNγ, GCSF, GM-CSF and TNFα, whilst levels of IL-7 and VEGF are increased.

TNFα Synthesis in Whole Blood Stimulated with 5 µg/ml PHA

Figure 22:
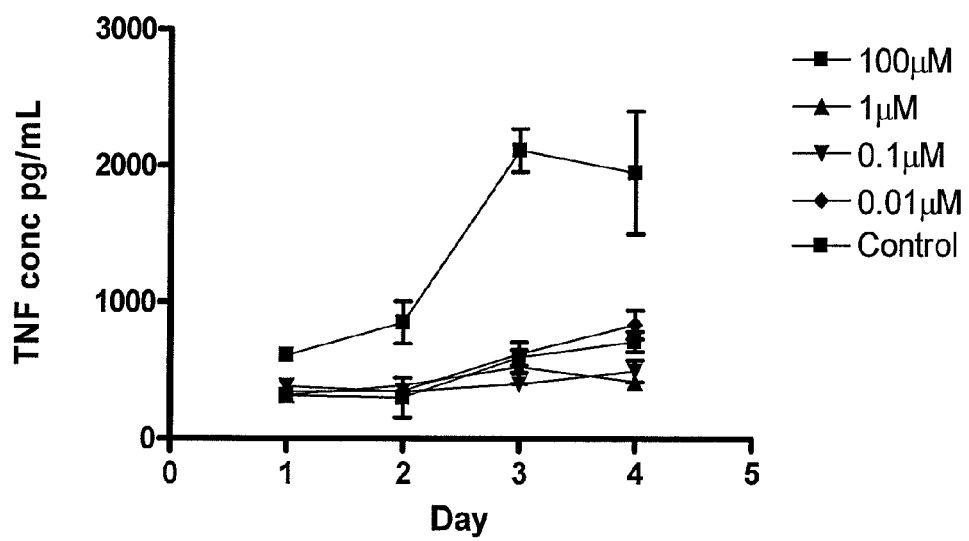
FIG. 22 shows the inhibition of TNF synthesis in human whole blood stimulated with 5 μg/ml PHA, by the addition of N-acetyl-β,β-diglucosylamine octasulphate (DOS) at concentrations of 0.01, 0.1 and 1 μM.
Figure 23:
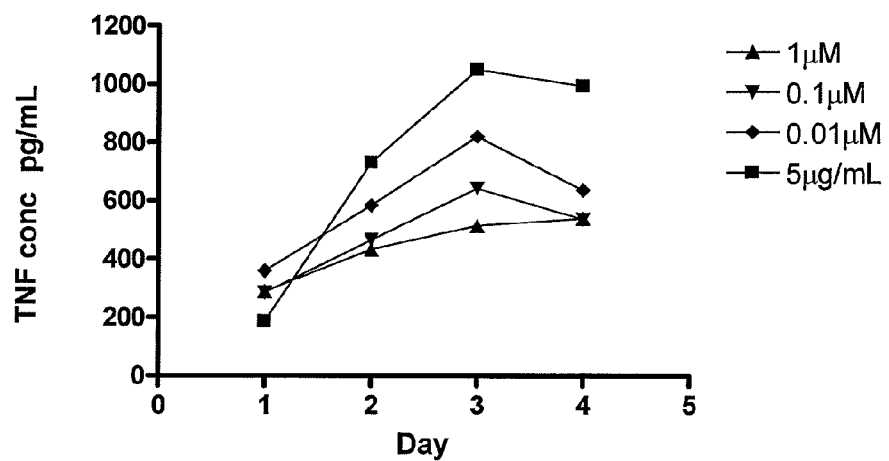
FIG. 23 shows the inhibition of TNF synthesis in human whole blood stimulated with 5 μg/ml PHA, by the addition of N-acetyl-β,β-diglucosylamine oligosulphate 1200 at concentrations of 0.01, 0.1 and 1 μM.

Human whole blood was diluted 1:10 in RPMI and stimulated with 5 µg/ml phytohaemagglutinin (PHA) for 4 days in the absence or presence of N-acetyl-β,β-diglucosylamine octasulphate (DOS) or N-acetyl-β,β-diglucosylamine oligosulphate 1200 at concentrations of 0.01, 0.1 or 1 µM. The TNFα concentrations were assayed by ELISA on days 1, 2, 3 and 4. The results are shown in FIGS. 22 and 23 respectively. It can be seen that N-acetyl-β,β-diglucosylamine octasulphate and N-acetyl-β,β-diglucosylamine oligosulphate 1200 effectively inhibit TNFα synthesis in whole blood stimulated with 5 µg/ml PHA.

LPS Stimulated U937 Macrophage TNFα Synthesis

Figure 24:
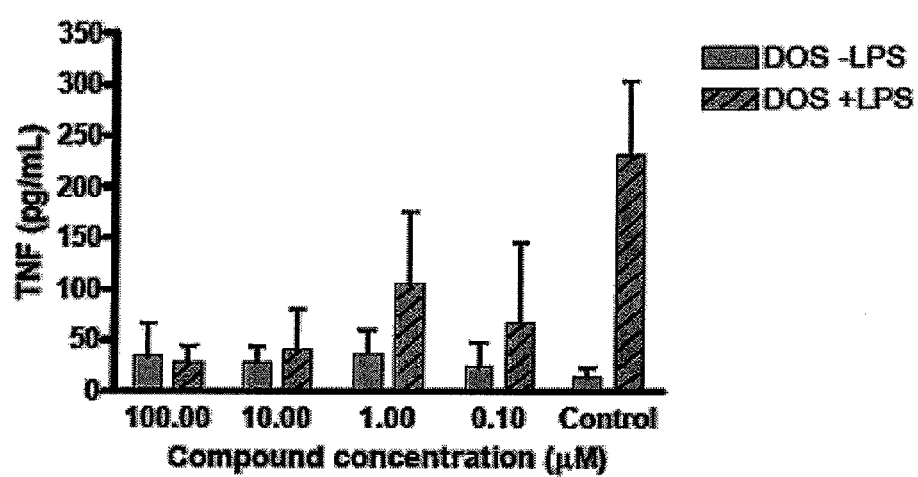
FIG. 24 shows the inhibition of differentiated U937 human macrophage TNFα synthesis by N-acetyl-β,β-diglucosylamine octasulphate (DOS) over a range of concentrations.

U937 human monocytes were incubated with 5 µg/ml PMA (phorbol myristate acetate) for 5 days in order to induce differentiation. N-acetyl-β,β-diglucosylamine octasulphate (DOS) was added to the macrophages produced at concentrations of 0 (control), 0.10, 1.00, 10.00 and 100.00 µM. TNFα synthesis was then optionally induced by 80 nM lps (lipopolysaccharide) treatment for 72 hours. The results are shown in FIG. 24. It can be seen that N-acetyl-β,β-diglucosylamine octasulphate (DOS) inhibited TNFα synthesis at all concentrations down to 0.1 µM.

It will be understood that the present invention has been described above by way of example only. The examples are not intended to limit the scope of the invention. Various modifications and embodiments can be made without departing from the scope and spirit of the invention, which is defined by the following claims only.

What is claimed is:

1. A compound comprising:
(i) a sequence of at least two monosaccharide subunits directly linked by a glycosidic —NR— group or a glycosidic —NR$_2^+$— group, wherein the glycosidic —NR— group or the glycosidic —NR$_2^+$— group is linked to both of the monosaccharide subunits by a glycosidic bond, and wherein each R is independently hydrogen, a —SO$_2$—OR' or —SO$_2$—N(R')$_2$ group, a further monosaccharide subunit, or a hydrocarbyl group, or two R groups and the nitrogen atom to which they are attached, together form a further monosaccharide subunit or a cyclic hydrocarbyl group; and
(ii) at least one sulphate group, wherein a sulphate group is a —O—SO$_2$—OR', —NR'—SO$_2$—OR', —O—SO$_2$—N(R')$_2$ or —NR'—SO$_2$—N(R')$_2$ group;

wherein each R' is independently hydrogen, a metal, a further monosaccharide subunit, or a hydrocarbyl group;
wherein each monosaccharide subunit independently is optionally substituted and/or optionally modified; and
wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;
or a salt thereof.

2. A compound as claimed in claim 1, wherein
each R is independently hydrogen, a further monosaccharide subunit, or a hydrocarbyl group, or two R groups and the nitrogen atom to which they are attached, together form a further monosaccharide subunit or a cyclic hydrocarbyl group.

3. A compound as claimed in claim 1:
(a) wherein all monosaccharide subunits are independently ring-closed or open-chain or a mixture of ring-closed and open-chain; and/or
(b) wherein one or more monosaccharide subunit is substituted and/or modified; and/or
(c) wherein in a substituted monosaccharide subunit:
 (i) independently one or more of the hydroxyl groups of the monosaccharide subunit is replaced with —H, —F, —Cl, —Br, —I, —CF$_3$, —CCl$_3$, —CBr$_3$, —CI$_3$, —SH, —NH$_2$, —N$_3$, —NH=NH$_2$, —CN, —NO$_2$, —COOH, —R$^a$—O—R$^b$, —R$^a$—S—R$^b$, —R$^a$—SO—R$^b$, —R$^a$—SO$_2$—R$^b$, —R$^a$—SO$_2$—OR$^b$, —R$^a$O—SO$_2$—R$^b$, —R$^a$—SO$_2$—N(R$^b$)$_2$, —R$^a$—NR$^b$—SO$_2$—R$^b$, —R$^a$O—SO$_2$—OR$^b$, —R$^a$O—SO$_2$—N(R$^b$)$_2$, —R$^a$—NR$^b$—SO$_2$—OR$^b$, —R$^a$—NR$^b$—SO$_2$—N(R$^b$)$_2$, —R$^a$—N(R$^b$)$_2$, —R$^a$—N(R$^b$)$_3^+$, —R$^a$—B(R$^b$)$_2$, —R$^a$—P(R$^b$)$_2$, —R$^a$—PO(R$^b$)$_2$, —R$^a$—Si(R$^b$)$_3$, —R$^a$—CO—R$^b$, —R$^a$—CO—OR$^b$, —R$^a$O—CO—R$^b$, —R$^a$—CO—N(R$^b$)$_2$, —R$^a$—NR$^b$—CO—R$^b$, —R$^a$O—CO—OR$^b$, —R$^a$O—CO—N(R$^b$)$_2$, —R$^a$—NR$^b$—CO—OR$^b$, —R$^a$—NR$^b$—CO—N(R$^b$)$_2$, —R$^a$—CS—R$^b$, —R$^a$—CS—OR$^b$, —R$^a$O—CS—R$^b$, —R$^a$—CS—N(R$^b$)$_2$, —R$^a$—NR$^b$—CS—R$^b$, —R$^a$O—CS—OR$^b$, —R$^a$O—CS—N(R$^b$)$_2$, —R$^a$—NR$^b$—CS—OR$^b$, —R$^a$—NR$^b$—CS—N(R$^b$)$_2$, or —R$^b$; and/or
 (ii) independently one, two or three of the hydrogens of the monosaccharide subunit is replaced with —F, —Cl, —Br, —I, —CF$_3$, —CCl$_3$, —CBr$_3$, —CI$_3$, —OH, —SH, —NH$_2$, —N$_3$, —NH=NH$_2$, —CN, —NO$_2$, —COOH, —R$^a$—O—R$^b$, —R$^a$—S—R$^b$, —R$^a$—SO—R$^b$, —R$^a$—SO$_2$—R$^b$, —R$^a$—SO$_2$—OR$^b$, —R$^a$O—SO$_2$—R$^b$, —R$^a$—SO$_2$—N(R$^b$)$_2$, —$R^a$—$NR^b$—$SO_2$—$R^b$, —$R^aO$—$SO_2$—$OR^b$, —$R^aO$—$SO_2$—$N(R^b)_2$, —$R^a$—$NR^b$—$SO_2$—$OR^b$, —$R^a$—$NR^b$—$SO_2$—$N(R^b)_2$, —$R^a$—$N(R^b)_2$, —$R^a$—$N(R^b)_3^+$, —$R^a$—$B(R^b)_2$, —$R^a$—$P(R^b)_2$, —$R^a$—$PO(R^b)_2$, —$R^a$—$Si(R^b)_3$, —$R^a$—$CO$—$R^b$, —$R^a$—$CO$—$OR^b$, —$R^aO$—$CO$—$R^b$, —$R^a$—$CO$—$N(R^b)_2$, —$R^a$—$NR^b$—$CO$—$R^b$, —$R^aO$—$CO$—$OR^b$, —$R^aO$—$CO$—$N(R^b)_2$, —$R^a$—$NR^b$—$CO$—$OR^b$, —$R^a$—$NR^b$—$CO$—$N(R^b)_2$, —$R^a$—$CS$—$R^b$, —$R^a$—$CS$—$OR^b$, —$R^aO$—$CS$—$R^b$, —$R^a$—$CS$—$N(R^b)_2$, —$R^a$—$NR^b$—$CS$—$R^b$, —$R^aO$—$CS$—$OR^b$, —$R^aO$—$CS$—$N(R^b)_2$, —$R^a$—$NR^b$—$CS$—$OR^b$, —$R^a$—$NR^b$—$CS$—$N(R^b)_2$, or —$R^b$; and/or (iii) independently one or more of the hydroxyl groups of the monosaccharide subunit, together with the hydrogen attached to the same carbon atom as the hydroxyl group, is replaced with =O, =S, =$NR^b$, or =$N(R^b)_2^+$; and/or (iv) independently two hydroxyl groups of the monosaccharide subunit are together replaced with —O—$R^c$—, —S—$R^c$—, —SO—$R^c$—, —$SO_2$—$R^c$—, or —$NR^b$—$R^c$—;

wherein:

—$R^a$— is independently a chemical bond, or a substituted or unsubstituted alkylene, alkenylene or alkynylene group which optionally includes one or more heteroatoms in its carbon skeleton;

—$R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton;

—$R^c$— is independently a chemical bond, or a substituted or unsubstituted alkylene, alkenylene or alkynylene group which optionally includes one or more heteroatoms in its carbon skeleton; and M is a metal;

provided that the monosaccharide subunit comprises at least one —$OR^b$, —$OSOR^b$, —$OSO_2R^b$, —$OSO_3R^b$, —$OSi(R^b)_3$, —$OCOR^b$, —$OCO_2R^b$, or —OM; and/or (d) wherein in a modified monosaccharide subunit the ring of the modified monosaccharide subunit, or what would be the ring in the ring-closed form of the modified monosaccharide subunit, is partially unsaturated; and/or (e) wherein in a modified monosaccharide subunit the ring oxygen of the modified monosaccharide subunit, or what would be the ring oxygen in the ring-closed form of the modified monosaccharide subunit, is replaced with —S— or —$NR^b$—, wherein —$R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton; and/or (f) wherein each hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton; and/or (g) wherein each hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton, and wherein a substituted hydrocarbyl group is substituted with one or more of —F, —Cl, —Br, —I, —$CF_3$, —$CCl_3$, —$CBr_3$, —$CI_3$, —OH, —SH, —$NH_2$, —$N_3$, —NH=$NH_2$, —CN, —$NO_2$, —COOH, —$R^a$—O—$R^b$, —$R^a$—S—$R^b$, —$R^a$—SO—$R^b$, —$R^a$—$SO_2$—$R^b$, —$R^a$—$SO_2$—$OR^b$, —$R^aO$—$SO_2$—$R^b$, —$R^a$—$SO_2$—$N(R^b)_2$, —$R^a$—$NR^b$—$SO_2$—$R^b$, —$R^aO$—$SO_2$—$OR^b$, —$R^aO$—$SO_2$—$N(R^b)_2$, —$R^a$—$NR^b$—$SO_2$—$OR^b$, —$R^a$—$NR^b$—$SO_2$—$N(R^b)_2$, —$R^a$—$N(R^b)_2$, —$R^a$—$N(R^b)_3^+$, —$R^a$—$B(R^b)_2$, —$R^a$—$P(R^b)_2$, —$R^a$—$PO(R^b)_2$, —$R^a$—$Si(R^b)_3$, —$R^a$—$CO$—$R^b$, —$R^a$—$CO$—$OR^b$, —$R^aO$—$CO$—$R^b$, —$R^a$—$CO$—$N(R^b)_2$, —$R^a$—$NR^b$—$CO$—$R^b$, —$R^aO$—$CO$—$OR^b$, —$R^aO$—$CO$—$N(R^b)_2$, —$R^a$—$NR^b$—$CO$—$OR^b$, —$R^a$—$NR^b$—$CO$—$N(R^b)_2$, —$R^a$—$CS$—$R^b$, —$R^a$—$CS$—$OR^b$, —$R^aO$—$CS$—$R^b$, —$R^a$—$CS$—$N(R^b)_2$, —$R^a$—$NR^b$—$CS$—$R^b$, —$R^aO$—$CS$—$OR^b$, —$R^aO$—$CS$—$N(R^b)_2$, —$R^a$—$NR^b$—$CS$—$OR^b$, —$R^a$—$NR^b$—$CS$—$N(R^b)_2$, —$R^b$, or a monosaccharide subunit;

wherein:

—$R^a$— is independently a chemical bond, or a substituted or unsubstituted alkylene, alkenylene or alkynylene group which optionally includes one or more heteroatoms in its carbon skeleton; and —$R^b$ is independently hydrogen, an optionally substituted monosaccharide subunit, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton; and/or (h) wherein the compound is a pharmaceutically acceptable salt; and/or (i) wherein the compound comprises a sequence of at least two monosaccharide subunits linked by a glycosidic —NR— group; and/or (j) wherein one R group is not hydrogen; and/or (k) wherein two R groups are not hydrogen; and/or (l) wherein one R group is a monosaccharide subunit and one R group is a hydrocarbyl group; and/or (m) wherein one R group is a monosaccharide subunit and one R group is hydrogen; and/or (n) wherein one R group is a hydrocarbyl group and one R group is hydrogen; and/or (o) wherein two R groups are independently monosaccharide subunits; and/or (p) wherein two R groups are independently hydrocarbyl groups; and/or (q) wherein one or two R groups are independently hydrogen, or an alkyl, acyl or alkoxycarbonyl group; and/or (r) wherein one or two R groups are independently hydrogen, or a $C_1$-$C_6$ alkyl, $C_2$-$C_6$ acyl, $C_2$-$C_6$ halo-acyl, or $C_{1-20}$ alkoxycarbonyl group; and/or (s) wherein one or two R groups are independently a methyl, ethyl, acetyl, trifluoroacetyl, Boc, Fmoc, or Zervas group; and/or (t) comprising at least two or at least three sulphate groups; and/or (u) comprising at least one —O—$SO_2$—OR', —NR'—$SO_2$—OR', or —O—$SO_2$—$N(R')_2$ group; and/or (v) comprising at least one —$OSO_3R'$ group; and/or (w) comprising at least two monosaccharide subunits, each of which is substituted with at least one sulphate group; and/or (x) comprising at least one pyranosyl subunit, which is substituted with one, two or three sulphate groups in the 2-, 3- and/or 6-position relative to the anomeric carbon of the pyranosyl subunit, optionally wherein the pyranosyl subunit is part of a disaccharide; and/or (y) comprising at least one pyranosyl subunit, which is substituted with two or three sulphate groups in the 2-, 3- and/or 6-position relative to the anomeric carbon of the pyranosyl subunit, optionally wherein the pyranosyl subunit is part of a disaccharide; and/or (z) comprising a first pyranosyl subunit, which is substituted with one sulphate group in the 2- or 6-position relative to the anomeric carbon of the pyranosyl subunit, and a second pyranosyl subunit, which is substituted with one sulphate group in the 2- or 3-position relative to the anomeric carbon of the pyranosyl subunit and one sulphate group in the 6-position relative to the anomeric carbon of the pyranosyl subunit, optionally wherein the first and second pyranosyl subunits form a disaccharide; and/or (aa) comprising at least one pyranosyl subunit, which is substituted with one or two sulphate groups in the 4- and/or 6-position relative to the anomeric carbon of the pyranosyl subunit, optionally wherein the pyranosyl subunit is part of an oligosaccharide or a polysaccharide; and/or (bb) comprising at least one, two or three sulphate groups, located on primary hydroxyl positions; and/or (cc) wherein a sulphate group is provided on a monosaccharide subunit comprising a glycosidic amine group; and/or (dd) wherein 1-50, or 2-30, or 3-15, or 6-12, or all the hydroxyl groups on the monosaccharide subunits independently have been replaced with a sulphate group; and/or (ee) wherein 1-9, or 2-8, or 3-4 hydroxyl groups on each of 1, 2, 3, 4, 5, 6, 7, 8, or all monosaccharide subunits independently have been replaced with a sulphate group; and/or (ff) wherein the compound is a partially or fully sulphated saccharide; and/or (gg) wherein R' is independently hydrogen, a metal, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton; and/or (hh) wherein R' is independently hydrogen, an alkali metal, an earth alkali metal, copper, silver, zinc, or a $C_1$-$C_6$ alkyl group; and/or (ii) comprising 2-100, 2-20, 2-10, or 2-4 monosaccharide subunits; and/or (jj) comprising 2, 3, 4, 5, 6, 7, 8, 9, 10 or more monosaccharide subunits; and/or (kk) comprising a sequence of 2, 3, 4, 5, 6, 7, 8, 9, 10 or more monosaccharide subunits; and/or (ll) wherein all monosaccharide subunits are independently aldosyl or ketosyl monosaccharides; and/or (mm) wherein all monosaccharide subunits are independently aldosyl or ketosyl monosaccharides, and wherein 1, 2, 3, 4, or all monosaccharide subunits are independently triosyl, tetrosyl, pentosyl, hexosyl, heptosyl, octosyl or nonosyl monosaccharides; and/or (nn) wherein all monosaccharide subunits are independently aldosyl or ketosyl monosaccharides, wherein 1, 2, 3, 4, or all monosaccharide subunits are independently triosyl, tetrosyl, pentosyl, hexosyl, heptosyl, octosyl or nonosyl monosaccharides, and wherein 1, 2, 3, 4, or all monosaccharide subunits are independently glycerosyl, erythrosyl, threosyl, ribosyl, arabinosyl, xylosyl, lyxosyl, allosyl, altrosyl, glucosyl, mannosyl, gulosyl, idosyl, galactosyl, talosyl, rhamnosyl or fucosyl monosaccharides; and/or (oo) wherein all monosaccharide subunits are independently in the D- or L-configuration; and/or (pp) wherein 1, 2, 3, 4, or all monosaccharide subunits are independently tetrosyl monosaccharides or higher, and the ring of those monosaccharides is furanosyl; and/or (qq) wherein 1, 2, 3, 4, or all monosaccharide subunits are independently pentosyl monosaccharides or higher, and the ring of those monosaccharides is pyranosyl; and/or (rr) wherein the stereochemistry of each glycosidic bond is independently α or β; and/or (ss) wherein the compound is:
  (i) a sulphated glucosylamine; or
  (ii) a sulphated β,β-di-glucosylamine; or
  (iii) a mono-, di-, tri-, tetra-, penta-, hexa-, hepta- or octasulphated β,β-di-glucosylamine, or a mixture thereof; or
  (iv) a mono-, di-, tri-, tetra-, penta-, hexa-, hepta- or octasulphated N-acetyl-β,β-di-glucosylamine, or a mixture thereof; or
  (v) a mono-, di-, tri-, tetra-, penta-, hexa-, hepta- or octasulphated N-ethyl-β,β-di-glucosylamine, or a mixture thereof; or
  (vi) a sulphated di-(4,4'-glucosylglucosyl)amine;

(tt) wherein the atom connectivity S—O—P is not present in any monosaccharide subunit and/or in the entire compound; and/or (uu) wherein the compound does not contain the group —O—P(=O)(OH)—O—SO$_2$OH; and/or (vv) wherein the compound does not comprise a ribose subunit comprising a glycosidic tertiary amine.

4. A compound having
(a) the formula (I):

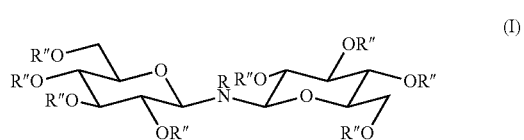

wherein:
R is Ac, Me, Et, COCF₃, or COPh;
each R″ is SO₃R' or H with at least one R″ being SO₃R'; and
each R' is H, Li, Na or K;
   or a tautomer, a stereoisomer or a salt thereof; or
(b) the formula (II):

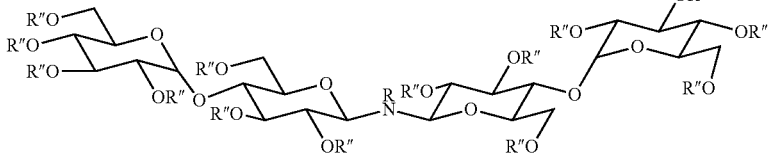

wherein:
R is Ac, Me, Et, COCF₃, or COPh;
each R″ is SO₃R' or H with at least one R″ being SO₃R'; and
each R' is H, Li, Na or K;
   or a tautomer, a stereoisomer or a salt thereof.

5. A polysaccharide, oligosaccharide, peptide or protein derivative comprising a polysaccharide, oligosaccharide, peptide or protein covalently linked to a compound as claimed in claim 1.

6. A method of synthesising a compound as claimed in claim 1, comprising the sulphation of a compound comprising:
   a sequence of at least two monosaccharide subunits directly linked by a glycosidic —NR— group or a glycosidic —NR₂⁺— group, wherein the glycosidic —NR— group or the glycosidic —NR₂⁺— group is linked to both of the monosaccharide subunits by a glycosidic bond, and wherein each R is independently hydrogen, a —SO₂—OR' or —SO₂—N(R')₂ group, a further monosaccharide subunit, or a hydrocarbyl group, or two R groups and the nitrogen atom to which they are attached, together form a further monosaccharide subunit or a cyclic hydrocarbyl group; or a salt thereof;
wherein each R' is independently hydrogen, a metal, a further monosaccharide subunit, or a hydrocarbyl group;
wherein each monosaccharide subunit independently is optionally substituted and/or optionally modified; and
wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

7. A method as claimed in claim 6, wherein:
(a) the compound is O- and/or N-protected prior to sulphation; and/or
(b) the compound is O- and/or N-protected prior to sulphation, and wherein O-silyl, O-acetyl, O-acyl, O-acetal, O-ketal, O-benzyl, O-benzoyl or O-THP protection is used; and/or
(c) the compound is O- and/or N-protected prior to sulphation, and wherein N-Boc, N-Fmoc, N-Zervas, N-acetyl, N-acyl, N-alkyl or N-trifluoroacetyl protection is used; and/or
(d) the sulphation is performed using sulphur trioxide complexed to a nitrogen-containing base; and/or
(e) the sulphation is performed using sulphur trioxide complexed to a nitrogen-containing base, and wherein the nitrogen-containing base is pyridine; and/or
(f) the sulphation is performed using sulphur trioxide complexed to a nitrogen-containing base, wherein the nitrogen-containing base is pyridine, and wherein pyridine is used as solvent; and/or
(g) the sulphation is performed using a halosulphonic acid or a silyl-protected halosulphonic acid; and/or
(h) the sulphation is performed using a halosulphonic acid or a silyl-protected halosulphonic acid, and wherein the halosulphonic acid or silyl-protected halosulphonic acid is chlorosulphonic acid or trimethylsilylchlorosulphonate respectively.

8. A product produced by a method as claimed in claim 6.

9. A pharmaceutical composition comprising a compound as claimed in claim 1, and a pharmaceutically acceptable excipient, carrier or diluent.

10. A method of binding, inhibiting, activating, modifying, destroying, re-folding, denaturising, aggregating, or oligomerising a macromolecule, wherein the macromolecule is a protein, peptide, nucleic acid, lipid, polysaccharide, oligosaccharide, glycosaminoglycan, or proteoglycan, comprising:
(a) contacting a compound as claimed in claim 1 with the macromolecule; and/or
(b) administering an effective amount of a compound as claimed in claim 1 to a patient in need thereof.

11. A method as claimed in claim 10, wherein:
(a) the binding, inhibiting, activating, modifying, destroying, re-folding, denaturising, aggregating, or oligomerising occurs in vitro, ex vivo or in vivo; and/or
(b) the macromolecule is a member of the lectin family of proteins; and/or
(c) the macromolecule is a transmembrane glycoprotein; and/or
(d) the macromolecule is a protein, and wherein the protein is a member of the selectin sub-class, optionally wherein the selectin is an E-, L- or P-selectin; and/or
(e) the macromolecule is a protein, and wherein the protein is a member of the siglecs sub-class; and/or
(f) the macromolecule is a mannose binding protein or a mannose receptor; and/or
(g) the macromolecule is a glycosidase, optionally wherein the glycosidase is a glucosidase, optionally wherein the glucosidase is a β-glucosidase; and/or
(h) the macromolecule is a growth factor, optionally wherein the growth factor is a granulocyte colony stimulating factor (G-CSF), a granulocyte macrophage colony stimulating factor (GM-CSF), a nerve growth factor (NGF), a neurotrophin, a platelet-derived growth factor (PDGF), erythropoietin (EPO), thrombopoietin (TPO), myostatin (GDF-8), growth differentiation factor-9 (GDF9), a hepatocyte growth factor, or a fibroblast growth factor (FGF); and/or
(i) the macromolecule is follistatin; and/or
(j) the macromolecule is a phosphorylase, optionally wherein the phosphorylase is glycogen, starch or maltodextrin phosphorylase and/or optionally wherein the phosphorylase is hepatic and/or optionally wherein the phosphorylase is phosphorylase a or phosphorylase b; and/or (k) the macromolecule is a cytokine receptor or a cytokine, optionally wherein the cytokine receptor or cytokine is a chemokine receptor or a chemokine and/or optionally wherein the chemokine is MCP-1 or MCP-3.

12. A method of modifying the level of a cytokine in vivo, ex vivo or in vitro, said method comprising contacting a compound as claimed in claim 1 with a cell.

13. A method of testing for an increase or decrease in the level of a cytokine in vivo, ex vivo or in vitro, said method comprising contacting a compound as claimed in claim 1 with a cell.

14. A method as claimed in claim 12, wherein:
(a) the cytokine is selected from GM-CSF, IL-1α, IL-1β, IL-2, IL-4, IL-5, IL-6, IL-7, IL-8, IL-10, IL-12, IL-13, IL-17, GCSF, VEGF, TNFα, RANTES, MCP-1 or IFNγ; and/or
(b) the cytokine is selected from GM-CSF, IL-1α, IL-1β, IL-2, IL-4, IL-5, IL-6, IL-10, IL-13, IL-17, GCSF, TNFα, or IFNγ, and wherein the method is a method of testing for a decrease in the level of GM-CSF, IL-1α, IL-1β, IL-2, IL-4, IL-5, IL-6, IL-10, IL-13, IL-17, GCSF, TNFα or IFNγ; and/or
(c) the cytokine is selected from IL-7 or VEGF, and wherein the method is a method of testing for an increase in the level of IL-7 or VEGF; and/or
(d) the method comprises contacting the compound or pharmaceutically acceptable salt thereof with a blood cell and/or a human cell; and/or
(e) the method is performed in vitro or in vivo; and/or
(f) the method is a method of treating or preventing a disease or condition.

15. A method as claimed in claim 12, wherein the method is a method of treating or preventing a disease or condition, and wherein:
(a) the disease or condition is inflammation; and/or
(b) the disease or condition is an inflammatory disorder, a proliferative disorder, an immune disorder, an angiogenesis-dependent disorder, a sensitivity disorder, an adverse endocrine reaction or a degenerative disorder; and/or
(c) the disease or condition is an inflammatory bowel disease, Crohn's disease, ulcerative colitis, collagenous colitis, lymphocytic colitis, ischaemic colitis, diversion colitis, infective colitis, indeterminate colitis, psoriasis, sarcoidosis, arthritis, rheumatoid arthritis, osteoarthritis, Behçet's syndrome, asthma, chronic obstructive pulmonary disease, atherosclerosis, cancer, inflammation, restenosis, papilloma, polyposis, fibrosis, proliferative bronchiolitis, tumour growth, proliferative periostitis, proliferative pulpitis, proliferative verrucous leukoplakia, macular degeneration, an autoimmune disorder, an immunodeficiency disorder, a transplant rejection disorder, a disorder related to a transplant, a disorder related to a renal, hepatic, corneal, cartilage, stem cell, chondrocyte, pulmonary, cardiac, vascular or myeloid transplant, HIV infection, AIDS, multiple sclerosis, systemic lupus erythematosus, septic shock, an allergy, a hyposensitivity, a hypersensitivity, hypersensitivity following the reactivation of herpes, diabetes, a degenerative disease or disorder, a degenerative joint disease, a neurodegenerative disease, an inflammatory degenerative disease, osteochondral defects, keratitis, herpes simplex or shingles; and/or
(d) the disease or condition is an autoimmune disease; and/or
(e) the disease or condition is a wound; and/or
(f) the disease or condition is depression; and/or
(g) the method is a method of aiding cartilage repair or cartilage regeneration.

16. A method of treating or preventing a disease or condition, comprising administering a therapeutically or prophylactically effective amount of a compound as claimed in claim 1 to a patient in need thereof, wherein:
(a) the disease or condition is inflammation; and/or
(b) the disease or condition is an inflammatory disorder, a proliferative disorder, an immune disorder, an angiogenesis-dependent disorder, a sensitivity disorder, an adverse endocrine reaction or a degenerative disorder; and/or
(c) the disease or condition is an inflammatory bowel disease, Crohn's disease, ulcerative colitis, collagenous colitis, lymphocytic colitis, ischaemic colitis, diversion colitis, infective colitis, indeterminate colitis, psoriasis, sarcoidosis, arthritis, rheumatoid arthritis, osteoarthritis, Behçet's syndrome, asthma, chronic obstructive pulmonary disease, atherosclerosis, cancer, inflammation, restenosis, papilloma, polyposis, fibrosis, proliferative bronchiolitis, tumour growth, proliferative periostitis, proliferative pulpitis, proliferative verrucous leukoplakia, macular degeneration, an autoimmune disorder, an immunodeficiency disorder, a transplant rejection disorder, a disorder related to a transplant, a disorder related to a renal, hepatic, corneal, cartilage, stem cell, chondrocyte, pulmonary, cardiac, vascular or myeloid transplant, HIV infection, AIDS, multiple sclerosis, systemic lupus erythematosus, septic shock, an allergy, a hyposensitivity, a hypersensitivity, hypersensitivity following the reactivation of herpes, diabetes, a degenerative disease or disorder, a degenerative joint disease, a neurodegenerative disease, an inflammatory degenerative disease, osteochondral defects, keratitis, herpes simplex or shingles; and/or
(d) the disease or condition is an autoimmune disease; and/or
(e) the disease or condition is a wound; and/or
(f) the disease or condition is depression; and/or
(g) the method is a method of aiding cartilage repair or cartilage regeneration.

17. A method as claimed in claim 12, wherein the method is a method of treating or preventing a disease or condition, and wherein:
(a) the patient to be treated is a mammal; and/or
(b) the patient to be treated is a human; and/or
(c) the patient to be treated is a non-human mammal; and/or
(d) the patient to be treated is a non-human mammal, and wherein the non-human mammal is mutilated or sacrificed as a result of the test.

18. A mixture of compounds as claimed in claim 1, wherein the compounds differ only in their stereochemistry at the anomeric centre and/or in their degree of sulphation and/or their position of sulphation.

19. A mixture of polysaccharide, oligosaccharide, peptide or protein derivatives as claimed in claim 5, wherein the derivatives differ only in their stereochemistry at the anomeric centre and/or in their degree of sulphation and/or their position of sulphation.

* * * * *